US007217812B2

(12) United States Patent
Hooper et al.

(10) Patent No.: US 7,217,812 B2
(45) Date of Patent: May 15, 2007

(54) EXTRANEOUS DNA SEQUENCE THAT FACILITATES HANTAVIRUS GENE EXPRESSION

(75) Inventors: Jay W. Hooper, New Market, MD (US); Connie S. Schmaljohn, Frederick, MD (US); Max Custer, Durham, NC (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 614 days.

(21) Appl. No.: 10/394,388

(22) Filed: Mar. 21, 2003

(65) Prior Publication Data

US 2004/0053216 A1 Mar. 18, 2004

Related U.S. Application Data

(63) Continuation-in-part of application No. 09/491,974, filed on Jan. 27, 2000, now abandoned.

(60) Provisional application No. 60/398,985, filed on Jul. 26, 2002, provisional application No. 60/367,128, filed on Mar. 22, 2002, provisional application No. 60/117,680, filed on Jan. 29, 1999.

(51) Int. Cl.
*C07H 21/04* (2006.01)
(52) U.S. Cl. ................ 536/24.1; 536/23.72; 424/204.1
(58) Field of Classification Search ............... 536/24.1, 536/23.72
See application file for complete search history.

(56) References Cited

U.S. PATENT DOCUMENTS

| 5,614,193 A | 3/1997 | Schmaljohn et al. .... 424/186.1 |
| 5,665,590 A | 9/1997 | Yang .............................. 435/6 |
| 2004/0053216 A1 | 3/2004 | Hooper et al. ................. 435/5 |

OTHER PUBLICATIONS

Montgomery et al., "DNA Vaccines", Pharmacol. Ther., vol. 74, No. 2, pp. 195-205 (1997).
Yong-K et al., "A Vaccinia Virus-Vectored Hantaan Virus Vaccine Protects Hamsters from Challenge with Hantaan and Seoul Viruses but Not Puumala Virus", J. Virology, Oct. 1995, vol. 69, No. 10, pp. 6417-6423.
Schmaljohn, "Prospects for Vaccines to Control Viruses in the Family Bunyaviridae", Reviews in Medical Virology, vol. 4, pp. 185-196 (1994).
McCluskie et al., "Route and Method of Delivery of DNA Vaccine Influence Immune Responses in Mice and Non-Human Primates", Molecular Medicine, 5:287-300 (1999).
Lanzacecchia, "Identifying Strategies for Immune Intervention", Science, vol. 260, May 1993, pp. 937-944.
McClain et al, "Clinical Evaluation of a VAccinia-Vectored Hantaan Virus Vaccine", J. Medical Virology, 60:77-85 (2000).
Young Kyu Chu et al., "Serological Relationships amoung Viruses in the Hantavirus Genus, Family Bunyaviridae", Virology 198, pp. 196-204 (1994).
Yong Kyu-Chu et al., "Cross-Neutralization of Hantaviruses with Immune Sera from Experimentally Infected Animals and from Hemorrhagic Fever with Renal Syndrome and Hantavirus Pulmonary Syndrome Patients", J. Infectious Dis., 172:1581-4 (1995).
Xiao et al., "Phylogenetic Analyses of Virus Isolates in the Genus Hantavirus, Family Bunyaviridae", Virology 198, pp. 205-217 (1994).
Losordo et al., "Use of the rabbit ear artery to serially assess foreign protein secretion after site-specific arterial gene transer in vivo. Evidence that anatomic identification of successful gene transfer may underestimate the potential magnitude of transgene expression", PubMed, National Library of Medicine, NCBI, 2 pages, from Circulation 1994, Feb. 1989, 2:785-792.
Anderson, "Human gene therapy", Nature, vol. 392, Suppl Apr. 30, 1998, pp. 25-30.
Verma et al., Gene therapy—promises, problems and prospects', Nature, vol. 389, Sep. 18, 1997, pp. 239-242.
Hooper et al., DNA Vaccination with Hantavirus M Segment Elicits Neutralizing Antibodies and Protects against Seoul Virus Infection, Virology 255, pp. 269-278 (1999).
Schmaljohn et al., "Antigenic Subunits of Hantaan Virus Expresed by Baculovirus and Vaccinia Virus Recombinants", J. Virology, vol. 64, pp. 3162-3170 (1990).
Schmaljohn et al., "Hantaviruses: A Global Disease Problem", Emerging Infectious Diseases, vol. 3, No. 2, pp. 95-103 (1997).
Custer et al., "Active and Passive Vaccination against Hantavirus Pulmonary Syndrome with Andes Virus M Genome Segment-Based DNA Vaccine", J. Virology, vol. 77, No. 18, Sep. 2003, pp. 9894-9905.
Hooper et al., "DNA Vaccination with the Hantaan Virus M Gene Protects Hamsters against Three of Four HFRS Hantaviruses and Elicits a High-Titer Neutralizing Antibody Response in Rhesus Monkeys", J. Virology, vol. 75, No. 18, Sep. 2001, pp. 8469-8477.
Donnelly et al., "DNA Vaccines", Annu. Rev. Immunol., 15:617-648 (1997).
Arikawa et al., "Coding Properties of the S and the M Genome Segments of Sapporo Rat Virus: Comparison to Other Causative Agents of Hemorrhagic Fever with Renal Syndrome", Virology 176, pp. 114-125 (1990).
Zhang et al., "Experimental study on specific cytotoxic T lymphocyte induded by nucleocapsid protein of Hantaan virus", ABSTRACT, Zhonghua Weishengwuxue He Mianyixue (2000), 20(1), 23-25, 2000:219664.

(Continued)

*Primary Examiner*—Jeffrey S. Parkin
(74) *Attorney, Agent, or Firm*—Elizabeth Arwine

(57) ABSTRACT

In this application is described a protective DNA vaccines against infection with HFRS- and HPS-associated hantaviruses. The vaccines were constructed by subcloning cDNA representing the medium (M) (encoding the G1 and G2 glycoproteins) into the DNA expression vector pWRG7077. Animals vaccinated with the M construct developed a neutralizing antibody response. Passive transfer experiments show that serum from vaccinated animals, when injected on days 4 or 5 after challenge, protected animals from lethal disease.

11 Claims, 26 Drawing Sheets

OTHER PUBLICATIONS

PCT International Search Report for corresponding PCT application PCT/US03/08810, mailed Jan. 24, 2005, 8 pates.

Schmaljohn and Hooper, pWRG/SEO-M vaccine construct, XP-002296289, 2 pages, Nov. 8, 2000.

PCT international application WO 00/44406 (PCT/US00/01999).

Hooper and Li,"Vaccines Against Hantaviruses", from Current Topics in Microbiology and Immunology, vol. 256, Hantaviruses, eds. Schmaljohn and Nichol, 2001, pp. 171-191.

Yoshimatsu et al., "Protective immunity of Hantaan virus nucleocapsid and envelope protein studies using baculovirus-expressed proteins", Arch. Virol. (1993), 130:365-376.

Stingl, "The Skin Initiation and Target Site of Immune Responses", from Skin Carcinogenesis in Man and in Experimental Models, eds. Hecker et al., 1993, pp. 45-57.

Gregoriadis, "Genetic Vaccines: Strategies for Optimization", Pharmaceutical Research, vol. 15, No. 5, 1998, pp. 661-670.

Kennedy et al., "Protein-Protein Coupling REactions and the Applications of Protein Conjugates", Clinica Chimica Acta, 70 (1976), pp. 1-31.

Schuurs et al., "Enzyme-Immunoassay", Clinica Chimica Acta, 81 (1977) pp. 1-40.

Yongxin et al., "Inactivated cell-culture Hanatavirus vaccine developed in China", Factors in the Emergence and Control of Rodent-borne Viral Diseases, 1999, pp. 157-161.

Kitamura et al., "Isolation of Virus Causing Hemorrhagic Fever with Renal Syndrome (HFRS) Through a Cell Culture System", Japan J. Med. Sci, Biol., 36, pp. 17-25 (1983).

Schmaljohn et al., "Expression of the envelope glycoproteins of Hantaan virus with vaccinia and baculovirus recombinants", Genetics and Pathogenicity of Negative Strand Viruses, Chap. 7, 1989, pp. 58-66.

Schmaljohn et al., "Isolation and Initial Characterization of a Newfound Hantavirus from California", Virology 206, pp. 963-972 (1995).

Lundkvist et al., "Characterization of Puumala Virus Nucleocapsid Protein: Identification of B-Cell Epitopes and Domains Involved in Protective Immunity", Virology 216, pp. 397-406 (1996).

Hooper et al., "A Lethal Disease Model for Hantavirus Pulmonary Syndrome", Virology, 289, pp. 6-14 (2001).

Konishi et al., "Mice Immunized with a Subviral Particle Containing the Japanese Encephalitis Virus prM/M and E proteins Are Protected from Lethal JEV Infection", Virology 188, pp. 714-720 (1992).

Arikawa et al., "Coding Properties of the S and the M Genome Segments of Sapporo Rat Virus: Comparison to Other Causative Agents of Hemorrhagic Fever with Renal Syndrome", Virology 176, pp. 114-125 (1990).

Kamrud et al., "Comparison of the Protective Efficacy of Naked DNA, DNA-based Sindbis Replicon, and Packaged Sindbis Replicon Vectors Expressing Hantavirus Structural Genes in Hamsters", Virology 263, pp. 209-219 (1999).

Liang et al., "Bacterial Expression of Neutralizing Mouse Monoclonal Antibody Fab Fragemetns to Hantaan Virus", Virology 217, pp. 262-271 (1996).

Dantas et al., Short Communications, "Characterization of Glycoprotein of Viruses Causing Hemorrhagic Fever with Renal Syndrome (HFRS) Using Monoclonal Antibodies", Virology 151, pp. 379-384 (1986).

Padula et al, "Hantavirus Pulmonary Syndrome Outbreak in Argentina: Molecular Evidence for Person-to-Person Transmission of Andes Virus", Virology 241, pp. 323-330 (1998).

Labuda et al., "Importance of Localized Skin Infection in Tick-Borne Encephalitis Virus Transmission", Virology 219, pp. 357-366 (1996).

Arikawa et al., "Characterization of Hantaan Virus Envelope Glycoprotein Antigenic Determinants Defined by Monoclonal Antibodies", J. Gen. Virol. (1989), 70, pp. 615-624.

Bharadwaj et al., "Genetic vaccines protect against Sin Nombre hantavirus challenge in the deer mouse (*Peromyscus maniculatus*)", J. of Gen. Virol. (2002), 83, pp. 1745-1751.

Asada et al., "Cross-reactive Immunity among Different Serotypes of Virus Causing Haemorrhagic Fever with Renal Syndrome", J. Gen. Virol., (1989), 70, pp. 819-825.

Ho Wang Lee et al., "Isolation of the Etiologic Agent of Korean Hemorrhagic Fever", J. Inf. Diseases, Voo. 137, No. 3, Mar. 1978, pp. 298-308.

Pertmer et al., "Gene gun-based nucleic acid immunization: elicitation of humoral and cytotoxic T lymphocyte responses following epidermal delivery of nanogram quantities of DNA", Vaccine 1995, No. 13, No. 15, pp. 1427-1430.

Bharadwaj et al., "Intramuscular inoculation of Sin Nombre hantavirus cDNAs induces cellular and humoral immune responses in BALB/c mice", Vaccine 17 (1999), pp. 2836-2843.

Schmaljohn et al., "Preparation of candidate vaccinia-vectored vaccines for haemorrhagic fever with renal syndrome", Vaccine, vol. 10, Issue 1, 1992, pp. 10-13.

Song et al., Papers, "Preliminary human trial of inactivated golden hamster kidney cell (GHKC) vaccine against haemorrhagic fever with renal syndrome (HFRS)", Vaccine, vol. 10, Issue 4, 1992, pp. 214-216.

Ulrich et al., "Chimaeric HBV core particles carrying a defined segment of Puumala hantavirus nucleocapsid protein evoke protective immunity in an animal model", Vaccine, vol. 16, No. 2/3, pp. 272-280 (1998).

Elgh et al., "Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes", J. Clinical Microbiology, May 1997, vol. 35, No. 5, pp. 1122-1130.

Pyung-Woo Lee, et al., "Serotypic Classification of Hantarviruses by Indirect Immunofluorescent Antibody and Plaque Reduction Neutralization Tests", J. Clinical Microbiology, Dec. 1985, vol. 22, No. 6, pp. 940-944.

Rollin et al., "Isolation of Black Creek Canal Virus, a New Hantavirus from Sigmodon hispidus in Florida", J. Medical Virology, 46:35-39 (1995).

Lundkvist et al., "Puumala and Dobrava Viruses Cause Hemorrhagic Fever with Renal Syndrome in Bosnia-Herzegovina" Evidence of Highly Cross-Neutralizing Antibody Responses in Early Patient Sera, J. Medical Virology, 53:51-59 (1997).

Qunying et al., "Immune Response to Inactivated Vaccine in People Naturally Infected with Hantaviruses", J. Medical Virology, 49:333-335 (1996).

Feltquate et al, "Different T Helper Cell Types and Antibody Isotypes Generated by Saline and Gene Gun DNA Immunization", J. Immunology, 1997, 158:2278-2284.

Wells and Estani, "An unusual hantavirus outbreak in southern Argentina" Person-to-person transmission?, Emerging Infectious Diseases, Apr.-Jun. 1997, vol. 3, Issue 2, pp. 171-174.

Toro et al., "An Outbreak of Hantavirus Pulmonary Syndrome, Chile 1997", Emerging Infectious Diseases, vol. 4, No. 4, Oct.-Dec. 1998, pp. 687-694.

Eisenbraun et al., "Examination of Parameters Affecting the Elicitation of Humoral Immune Responses by Particle Bombardment-Mediated Genetic Immunization", DNA and Cell Biology, vol. 12, No. 9, 1993, pp. 791-797.

Fynan et al., "DNA vaccines: Protective immunizations by parenteral, mucosal, and gene-gun inoculations", Proc. Natl. Acad. Sci, USA, vol. 90. pp. 11478-11482, Dec. 1993.

Lee et al., "Field trial of an inactivated vaccine against hemorrhagic fever with renal syndrome in humans", Arch Virol (1990), Suppl. 1: 35, pp. 35-47.

Zhang et al., "Characteristics of passive immunity against hantavirus infection in rats", Arch Virol, (1989) 105: 235-246.

Takenaka et al., "Antiviral Neutralizing Antibody to Hantaan Virus as Determined by Plaque Reduction Technique", Archives of Virology, 84, pp. 197-206 (1985).

Chapman et al, "Effect of intron A from human cytomegalovirus (Towne) immediate-early gene on heterologous expression in mammalian cells", Nucleic Acids Research, vol. 19, No. 14, pp. 3979-3986 (1991).

Robinson and Torres, "DNA vaccines", Seminars in Immunology, vol. 9 (1997), pp. 271-283.

Stenberg et al., "Structural Analysis of the Major Immediate Early Gene of Human Cytomegalovirus", J. Virology, Jan. 1984, vol. 49, No. 1, pp. 190-199.

Pensiero et al., "Expression of the Hantaan Virus M. Genome Segment by Using a Vaccinia Virus Recombinant", J. Virology, Mar. 1988, vol. 62, No. 3, pp. 696-702.

Ravkov et al., "Role of Actin Microfilaments in Black Creek Canal Virus Morphogenesis", J. Virology, Apr. 1988, vol. 72, No. 4, pp. 2865-2870.

Schmaljohn et al., "Naked DNA Vaccines Expressing the prM and E Genes of Russian Spring Summer Encephalitis Virus and Central European Encephalitis Virus Protect Mice from Homologous and Heterologous Challenge", J. Virology, vol. 71, No. 12, Dec. 1997, pp. 9563-9569.

Xu et al., "Immunity to Hantavirus Challenge in Meriones Unguiculatus Induced by Vaccinia-Vectored Viral Proteins", Am. J. Trop. Med. Hyg., 47(4), 1992, pp. 397-404.

Niklasson et al., "Comparison of European Isolates of Viruses Causing Hemorrhagic Fever with Renal Syndrome by a Neutralization Test", Am. J. Trop. Med. Hyg., 45(6), 1991, pp. 660-665.

Bharadwaj et al., "Humoral Immune Responses in the Hantavirus Cardiopulmonary Syndrome", J. Infectious Diseases, 182:43-48 (2000).

Meissner et al., "Complete nucleotide sequence of a Chilean hantavirus", Virus Research, 89 (2002), pp. 131-143.

Ma et al., "Murine leukemia virus pseudotypes of La Crosse and Hantaan Bunyaviruses: a system for analysis of cell tropism", Virus Research 64 (1999), pp. 23-32.

Kamrud et al., "Expression strategy of the M genome segment of Hantaan virus", Virus Research, 31 (1994), pp. 109-121.

FIG. 1 pWRG/SEO-M or pWRG/SEO-S

- CMV IE promoter
- Intron A
- SEOV M or SEOV S
- BGH pA
- KAN

FIG. 2A
pWRG/SEO-S
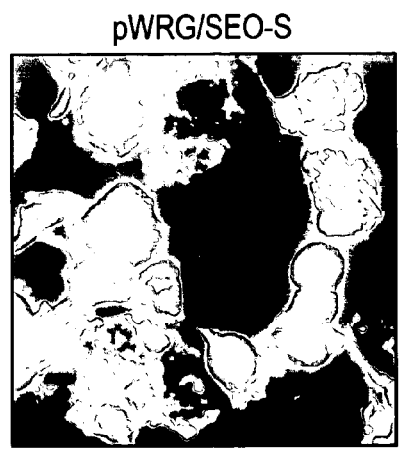
pWRG/SEO-M
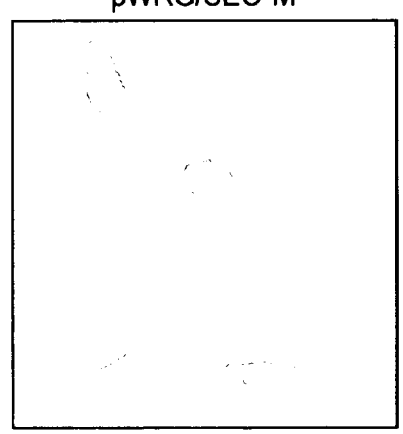
pWRG7077
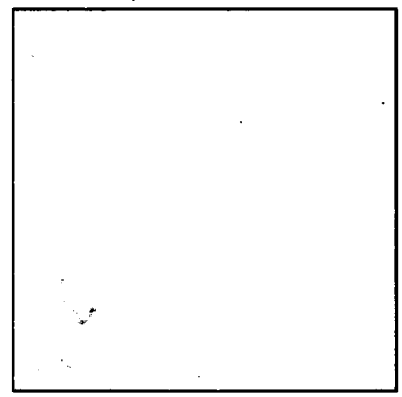
FIG. 2B
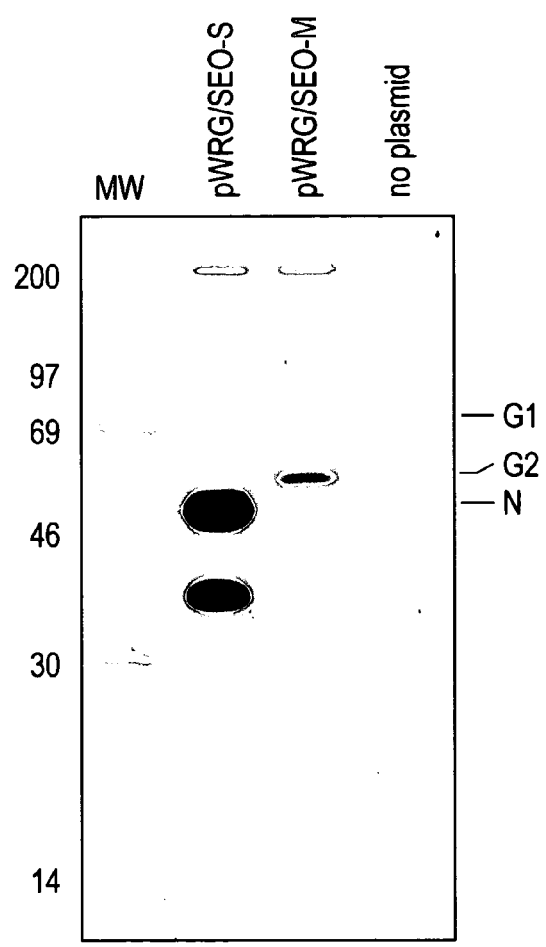

SEO-M

SEO-S

FIG. 6

Vaccination with pWRG/SEO-M protects against Dobrava virus

FIG. 7

Vaccination with pWRG/SEO-M fails to protect against Puumala virus

FIG. 10 pWRG/HTN-M(x)
7807 bp

- CMV Promoter
- Exon1
- IntronA
- Exon2
- Extraneous sequence
- Hantaan M 5'-UTR
- Hantaan virus M ORF
- Hantaan M 3'-UTR
- BGH polyA
- pUC19
- KanR

FIG. 16 pWRG/AND-M
7913 bp

CMV Promoter, Exon1, IntronA, Exon2, Extraneous sequence, Andes M 5'-UTR, Andes virus M ORF, Andes M 3'-UTR, BGH polyA, pUC19, KanR

SEQUENCE LISTING

<160> NUMBER OF SEQ ID NOS: 22

<210> SEQ ID NO 1
<211> LENGTH: 3651
<212> TYPE: DNA
<213> ORGANISM: Seoul hantavirus
<220> FEATURE:

<400> SEQUENCE: 1

| | |
|---|---:|
| tagtagtaga ctccgcaaga aacagcagtt aaagaacaat | 40 |
| aggatcatgt ggagtttgct attactggcc gctttagttg | 80 |
| gccaaggctt tgcattaaaa aatgtatttg acatgagaat | 120 |
| tcagttgccc cactcagtca actttgggga aacaagtgtg | 160 |
| tcaggctata cagaatttcc cccactctca ttacaggagg | 200 |
| cagaacagct agtgccagag agctcatgca acatggacaa | 240 |
| ccaccagtca ctctcaacaa taaataaatt aaccaaggtc | 280 |
| atatggcgga aaaagcaaa tcaggaatca gcaaaccaga | 320 |
| attcatttga agttgtggaa agtgaagtca gctttaaagg | 360 |
| gttgtgtatg ttaaagcata gaatggttga agaatcatat | 400 |
| agaaatagga gatcagtaat ctgttatgat ctagcctgta | 440 |
| atagtacatt ctgtaaacca actgtttata tgattgttcc | 480 |
| tatacatgct tgcaacatga tgaaaagctg tttgattggc | 520 |
| cttggcccct acagaatcca ggttgtctat gaaaggacat | 560 |
| actgcactac gggtatattg acagaaggaa atgctttgt | 600 |
| ccctgacaag gctgttgtca gtgcattgaa agaggcatg | 640 |
| tatgctatag caagcataga gacaatctgc ttttttattc | 680 |
| atcagaaagg gaatacatat aagatagtga ctgccattac | 720 |
| atcagcaatg ggctccaaat gtaataatac agatactaaa | 760 |
| gttcaaggat attatatctg tattattggt ggaaactccg | 800 |
| cccctgtata tgcccctgct ggtgaagact tcagagcaat | 840 |
| ggaggttttt tctgggatta ttacatcacc acatggagaa | 880 |
| gaccatgacc tacccggcga agaaatcgca acgtaccaga | 920 |
| tttcagggca gatagaggca aaaatccctc atacagtgag | 960 |
| ctccaaaaac ttaaaattga ctgcttttgc aggtattcca | 1000 |
| tcatactcat caactagtat attggctgct tcagaagatg | 1040 |
| gtcgtttcat atttagtcct ggtttatttc ctaacctaaa | 1080 |
| tcagtcagtc tgtgacaaca atgcactccc tttaatctgg | 1120 |
| aggggcctaa ttgatttaac gggatactat gaggcagtcc | 1160 |
| acccttgcaa tgtgttctgt gtcttatcag gaccaggtgc | 1200 |
| ttcatgtgag gcttttcag aaggaggtag gggcaatatt | 1240 |
| acttctccaa tgtgtctggt gtctaagcaa aatagattta | 1280 |
| gagcagctga gcagcagatt agctttgtct gccaaagagt | 1320 |

| | |
|---|---|
| tgatatggat attatagtgt actgtaatgg tcagaaaaaa | 1360 |
| acaatcctaa caaaaacatt agttataggc caatgtattt | 1400 |
| atactattac aagtctcttt tcactgttac caggggttgc | 1440 |
| ccattctatt gctattgagt tgtgtgttcc agggtttcat | 1480 |
| ggctgggcca cagctgcact tttgattaca ttctgcttcg | 1520 |
| gctgggtatt gattcctgca tgtacattag ctattctttt | 1560 |
| agtccttaag ttctttgcaa atatccttca tacaagcaat | 1600 |
| caagagaacc gattcaaagc cattctacgg aaaataaagg | 1640 |
| aggagtttga aaaaacaaag ggttccatgg tttgtgagat | 1680 |
| ctgtaagtat gagtgtgaaa cattaaagga attgaaggca | 1720 |
| cataacctat catgtgttca aggagagtgc ccatattgct | 1760 |
| ttacccactg tgaaccgaca gaaactgcaa ttcaggcaca | 1800 |
| ttacaaagtt tgtcaagcca cccaccgatt cagagaagat | 1840 |
| ttaaaaaga ctgtaactcc tcaaaatatt gggccaggct | 1880 |
| gttaccgaac actaaatctt tttaggtata aagtaggtg | 1920 |
| ttatattctg acaatgtgga ctcttcttct cattattgaa | 1960 |
| tccatcctct gggcagcaag tgcagcagaa atccccccttg | 2000 |
| tccctctctg gacagataat gctcatggcg ttgggagtgt | 2040 |
| tcctatgcat acggatcttg aattagactt ctctttgcca | 2080 |
| tccagttcta agtacacata caaaagacat ctcacaaacc | 2120 |
| cagttaatga ccaacagagt gtctcattgc atatagaaat | 2160 |
| tgaaagtcaa ggcattggtg ctgctgttca tcatcttgga | 2200 |
| cattggtatg atgcaagatt gaatctaaaa acctcatttc | 2240 |
| attgttatgg tgcctgcaca aaatatcaat acccatggca | 2280 |
| cactgcaaaa tgccattttg agaaagatta tgagtatgaa | 2320 |
| aatagctggg cttgcaaccc cccagattgc ccaggggttg | 2360 |
| gtacaggttg tactgcttgt ggattatatc tagatcaatt | 2400 |
| gaagccggta ggaacagcct ttaaaattat aagtgtaaga | 2440 |
| tacagtagaa aagtgtgcgt gcagtttggt gaagaacacc | 2480 |
| tttgtaaaac aattgatatg aatgattgct ttgtgactag | 2520 |
| gcatgccaaa atatgtataa ttgggactgt atctaagttt | 2560 |
| tctcaaggtg acactctact atttctgggg cccatggaag | 2600 |
| gaggtggtat aatctttaaa cactggtgta catctacctg | 2640 |
| tcactttgga gaccctggtg atgtcatggg tccaaaagat | 2680 |
| aaaccattta tttgccctga atttccaggg caatttagga | 2720 |
| aaaaatgtaa ctttgccaca actccagttt gtgaatatga | 2760 |
| tggaaacatt atatcaggct ataagaaagt acttgcaaca | 2800 |
| attgattctt tccaatcatt taacacaagc aatatacact | 2840 |
| tcactgatga gagaattgaa tggagagacc ctgatggcat | 2880 |
| gcttcgggat catattaata ttgttatttc taaagatatt | 2920 |

-continued

```
gattttgaaa atttggctga gaatccttgt aaagtagggc              2960
tccaggcagc aaacatagaa ggtgcctggg gttcaggtgt              3000
cgggtttaca ctcacatgca aggtgtctct cacagaatgc              3040
ccaacatttc ttacatcaat aaaggcctgt gacatggcaa              3080
tttgttatgg tgcagaaagt gtgacactct cacgaggaca              3120
aaatactgtc aaaattaccg ggaaaggtgg ccatagtggt              3160
tcttcattca aatgctgtca tgggaaagaa tgttcatcaa              3200
ctggcctcca agccagtgca ccacatctgg ataaggtaaa              3240
tggtatctct gagttagaaa acgagaaagt ttatgatgac              3280
ggtgcacctg aatgtggcat tacttgttgg tttaaaaaat              3320
caggtgaatg ggttatgggt ataatcaatg ggaactgggt              3360
tgtcctaatt gtcttgtgtg tactgctgct cttttctctt              3400
atcctgttga gcatcttgtg tcctgttaga aagcataaaa              3440
aatcataaat cccacctaac aatcttcaca tcatgtatcg              3480
attttcaaac actttatcat ttagaactta acttggcact              3520
actatctgat aactgacttt cattttatt tttatatgga               3560 ttaattacta aaaaaatac tctcttctat ctcccaatct               3600
tttattgatt caccggggtg ctgtcttgac atctggcggc              3640
gtctactact a                                             3651
```

<210> SEQ ID NO 2
<211> LENGTH: 1769
<212> TYPE: DNA
<213> ORGANISM: Seoul hantavirus
<220> FEATURE:

<400> SEQUENCE: 2

```
tagtagtaga ctccctaaag agctactaca ctaacaagaa              40
aaatggcaac tatggaagaa atccagagag aaatcactgc              80
tcacgagggg cagcttgtga tagcacgcca gaaggtcaag              120
gatgcagaaa agcagtatga gaaggatcct gatgacttaa              160
acaagagggc actgcatgat cgggagagtg tcgcagcttc              200
aatacaatca aaaattgatg aattgaagcg ccaacttgcc              240
gacagattgc agcagggaag aacatccggg caggaccggg              280
atcctacagg ggtagagcca ggtgatcatc ttaaggaaag              320
atcagcacta agctacggga atacactgga cctgaatagt              360
cttgacattg atgaacctac aggacagaca gctgattggc              400
tgaccataat tgtctatctg acatcattcg tggtcccgat              440
catcttgaag gcactgtaca tgttaacaac acgaggtagg              480
cagacttcaa aggacaacaa ggggatgagg atcagattca              520
aggatgacag ctcatatgag gatgtcaatg gaatcagaaa              560
gcccaaacat ctgtatgtgt caatgccaaa cgcccaatcc              600
agcatgaagg ctgaagagat aacaccagga agattccgca              640
```

-continued

| | |
|---|---|
| ctgcagtatg tggactatat cctgcacaga taaaggcaag | 680 |
| gaatatggta agccctgtca tgagtgtagt tgggttcttg | 720 |
| gcactggcaa aagactggac atcgagaatt gaagaatggc | 760 |
| tcggtgcacc ctgcaaattc atggcggagt ctcttattgc | 800 |
| cgggagttta tctgggaatc ctgtgaatcg tgactatatc | 840 |
| agacagagac aaggtgcact tgcagggatg gagccaaagg | 880 |
| aatttcaagc cctcaggcaa cattcaaagg atgctggatg | 920 |
| tacactagtt gaacatattg agtcaccatc atcaatatgg | 960 |
| gtgtttgctg gggcccctga taggtgtcca ccaacatgct | 1000 |
| tgtttgtcgg agggatggct gaattaggtg ccttcttttc | 1040 |
| tatacttcag gatatgagga acacaatcat ggcttcaaaa | 1080 |
| actgtgggca cagctgatga aaagcttcga agaaatcat | 1120 |
| cattctatca atcataccct agacgcacac aatcaatggg | 1160 |
| aatacaactg gaccagagga taattgttat gtttatggtt | 1200 |
| gcctggggaa aggaggcagt ggacaacttt catctcggtg | 1240 |
| atgacatgga tccagagctt cgtagcctgg ctcagatctt | 1280 |
| gattgaccag aaagtgaagg aaatctcaaa ccaggaacct | 1320 |
| atgaaattat aagtacataa atatataatc aatactaact | 1360 |
| ataggttaag aaatactaat cattagttaa taagaatata | 1400 |
| gatttattga ataatcatat taaataatta ggtaagttaa | 1440 |
| ctagtattta gttaagttag ctaattgatt tatatgattg | 1480 |
| tcacaattaa atgtaatcat aagcacaatc actgccatgt | 1520 |
| ataatcacgg gtatacgggt ggttttcata tggggaacag | 1560 |
| ggtgggctta gggccaggtc accttaagtg accttttttt | 1600 |
| gtatatatgg atgtagattt caattgatcg aatactaatc | 1640 |
| ctactgtcct cttttctttt cctttctcct tctttactaa | 1680 |
| caacaacaaa ctacctcaca ccttaatata tactacttta | 1720 |
| ttaagttgtt aagttgtgtc tttttgggga gtaagggagt | 1760 |
| ctactacta | 1769 |

<210> SEQ ID NO 3
<211> LENGTH: 8001
<212> TYPE: DNA
<213> ORGANISM: Artificial sequence
<220> FEATURE:
<223> OTHER INFORMATION: pWRG-SEO-M = Seoul hantavirus M segment, strain SR-11, subcloned into DNA vector pWRG7077

<400> SEQUENCE: 3

| | |
|---|---|
| gggggggggg ggcgctgagg tctgcctcgt gaagaaggtg | 40 |
| ttgctgactc ataccaggcc tgaatcgccc catcatccag | 80 |
| ccagaaagtg agggagccac ggttgatgag agctttgttg | 120 |
| taggtggacc agttggtgat tttgaacttt tgctttgcca | 160 |
| cggaacggtc tgcgttgtcg ggaagatgcg tgatctgatc | 200 |

```
cttcaactca gcaaaagttc gatttattca acaaagccga          240
cgtcccgtca agtcagcgta atgctctgcc agtgttacaa          280
ccaattaacc aattctgatt agaaaaactc atcgagcatc          320
aaatgaaact gcaatttatt catatcagga ttatcaatac          360
catattttg aaaaagccgt ttctgtaatg aaggagaaaa           400
ctcaccgagg cagttccata ggatggcaag atcctggtat          440
cggtctgcga ttccgactcg tccaacatca atacaaccta          480
ttaatttccc ctcgtcaaaa ataaggttat caagtgagaa          520
atcaccatga gtgacgactg aatccggtga aatggcaaa           560
agcttatgca tttcttcca gacttgttca acaggccagc           600
cattacgctc gtcatcaaaa tcactcgcat caaccaaacc          640
gttattcatt cgtgattgcg cctgagcgag acgaaatacg          680
cgatcgctgt taaaggaca attacaaaca ggaatcgaat           720
gcaaccggcg caggaacact gccagcgcat caacaatatt          760
ttcacctgaa tcaggatatt cttctaatac ctggaatgct          800
gttttcccgg ggatcgcagt ggtgagtaac catgcatcat          840
caggagtacg gataaaatgc ttgatggtcg gaagaggcat          880
aaattccgtc agccagttta gtctgaccat ctcatctgta          920
acatcattgg caacgctacc tttgccatgt ttcagaaaca          960
actctggcgc atcgggcttc ccatacaatc gatagattgt          1000
cgcacctgat tgccccacat tatcgcgagc ccatttatac          1040
ccatataaat cagcatccat gttggaattt aatcgcggcc          1080
tcgagcaaga cgtttcccgt tgaatatggc tcataacacc          1120
ccttgtatta ctgtttatgt aagcagacag ttttattgtt          1160
catgatgata tattttatc ttgtgcaatg taacatcaga            1200
gattttgaga cacaacgtgg cttcccccc ccccccggca            1240
tgcctgcagg tcgacataaa tcaatattgg ctattggcca          1280
ttgcatacgt tgtatctata tcataatatg tacatttata          1320
ttggctcatg tccaatatga ccgccatgtt gacattgatt          1360
attgactagt tattaatagt aatcaattac ggggtcatta          1400
gttcatagcc catatatgga gttccgcgtt acataactta          1440
cggtaaatgg cccgcctcgt gaccgcccaa cgaccccgc            1480
ccattgacgt caataatgac gtatgttccc atagtaacgc          1520
caatagggac tttccattga cgtcaatggg tggagtattt          1560
acggtaaact gcccacttgg cagtacatca agtgtatcat          1600
atgccaagtc cggcccccta ttgacgtcaa tgacggtaaa          1640
tggcccgcct ggcattatgc ccagtacatg accttacggg          1680
actttcctac ttggcagtac atctacgtat tagtcatcgc          1720
tattaccatg gtgatgcggt tttggcagta caccaatggg          1760
```

```
cgtggatagc ggtttgactc acggggattt ccaagtctcc               1800
accccattga cgtcaatggg agtttgtttt ggcaccaaaa               1840
tcaacgggac tttccaaaat gtcgtaataa ccccgccccg               1880
ttgacgcaaa tgggcggtag gcgtgtacgg tgggaggtct               1920
atataagcag agctcgttta gtgaaccgtc agatcgcctg               1960
gagacgccat ccacgctgtt ttgacctcca tagaagacac               2000
cgggaccgat ccagcctccg cggccgggaa cggtgcattg               2040
gaacgcggat tccccgtgcc aagagtgacg taagtaccgc               2080
ctatagactc tataggcaca ccccttttggc tcttatgcat              2120 gctatactgt ttttggcttg gggcctatac accccccgctc              2160 cttatgctat aggtgatggt atagcttagc ctataggtgt               2200
gggttattga ccattattga ccactcccct attggtgacg               2240
atactttcca ttactaatcc ataacatggc tctttgccac               2280
aactatctct attggctata tgccaatact ctgtccttca               2320
gagactgaca cggactctgt attttttacag gatggggtcc              2360 catttattat ttacaaattc acatatacaa caacgccgtc               2400
ccccgtgccc gcagttttta ttaaacatag cgtgggatct               2440
ccacgcgaat ctcgggtacg tgttccggac atgggctctt               2480
ctccggtagc ggcggagctt ccacatccga gccctggtcc               2520
catgcctcca gcggctcatg gtcgctcggc agctccttgc               2560
tcctaacagt ggaggccaga cttaggcaca gcacaatgcc                2600
caccaccacc agtgtgccgc acaaggccgt ggcggtaggg                2640
tatgtgtctg aaaatgagct cggagattgg gctcgcaccg                2680
tgacgcagat ggaagactta aggcagcggc agaagaagat                2720
gcaggcagct gagttgttgt attctgataa gagtcagagg                2760
taactcccgt tgcggtgctg ttaacggtgg agggcagtgt                2800
agtctgagca gtactcgttg ctgccgcgcg cgccaccaga                2840
cataatagct gacagactaa cagactgttc cttttccatgg              2880 gtcttttctg cagtcaccgt ccaagcttgc ggccgcggat                2920
ctgcaggaat tcggcacgag agtagtagac tccgcaagaa                2960
acagcagtta aagaacaata ggatcatgtg gagtttgcta                3000
ttactggccg ctttagttgg ccaaggcttt gcattaaaaa                3040
atgtatttga catgagaatt cagttgcccc actcagtcaa                3080
ctttggggaa acaagtgtgt caggctatac agaatttccc                3120
ccactctcat tacaggaggc agaacagcta gtgccagaga                3160
gctcatgcaa catggacaac caccagtcac tctcaacaat                3200
aaataaatta accaaggtca tatggcggaa aaaagcaaat                3240
caggaatcag caaaccagaa ttcatttgaa gttgtggaaa                3280
gtgaagtcag ctttaaaggg ttgtgtatgt taaagcatag                3320
aatggttgaa gaatcatata gaaataggag atcagtaatc                3360
```

| | |
|---|---|
| tgttatgatc tagcctgtaa tagtacattc tgtaaaccaa | 3400 |
| ctgtttatat gattgttcct atacatgctt gcaacatgat | 3440 |
| gaaaagctgt ttgattggcc ttggcccta cagaatccag | 3480 |
| gttgtctatg aaaggacata ctgcactacg ggtatattga | 3520 |
| cagaaggaaa atgctttgtc cctgacaagg ctgttgtcag | 3560 |
| tgcattgaaa agaggcatgt atgctatagc aagcatagag | 3600 |
| acaatctgct tttttattca tcagaaaggg aatacatata | 3640 |
| agatagtgac tgccattaca tcagcaatgg gctccaaatg | 3680 |
| taataataca gatactaaag ttcaaggata ttatatctgt | 3720 |
| attattggtg gaaactccgc ccctgtatat gcccctgctg | 3760 |
| gtgaagactt cagagcaatg gaggtttttt ctgggattat | 3800 |
| tacatcacca catggagaag accatgacct acccggcgaa | 3840 |
| gaaatcgcaa cgtaccagat ttcagggcag atagaggcaa | 3880 |
| aaatccctca tacagtgagc tccaaaaact taaaattgac | 3920 |
| tgcttttgca ggtattccat catactcatc aactagtata | 3960 |
| ttggctgctt cagaagatgg tcgtttcata tttagtcctg | 4000 |
| gtttatttcc taacctaaat cagtcagtct gtgacaacaa | 4040 |
| tgcactccct ttaatctgga ggggcctaat tgatttaacg | 4080 |
| ggatactatg aggcagtcca cccttgcaat gtgttctgtg | 4120 |
| tcttatcagg accaggtgct tcatgtgagg ccttttcaga | 4160 |
| aggaggtatt ttcaatatta cttctccaat gtgtctggtg | 4200 |
| tctaagcaaa atagatttag agcagctgag cagcagatta | 4240 |
| gctttgtctg ccaaagagtt gatatggata ttatagtgta | 4280 |
| ctgtaatggt cagaaaaaaa caatcctaac aaaaacatta | 4320 |
| gttataggcc aatgtattta ctattaca agtctctttt | 4360 |
| cactgttacc aggggttgcc cattctattg ctattgagtt | 4400 |
| gtgtgttcca gggtttcatg gctgggccac agctgcactt | 4440 |
| ttgattacat tctgcttcgg ctgggtattg attcctgcat | 4480 |
| gtacattagc tattctttta gtccttaagt tctttgcaaa | 4520 |
| tatccttcat acaagcaatc aagagaaccg attcaaagcc | 4560 |
| attctacgga aaataaagga ggagtttgaa aaaacaaagg | 4600 |
| gttccatggt ttgtgagatc tgtaagtatg agtgtgaaac | 4640 |
| attaaaggaa ttgaaggcac ataacctatc atgtgttcaa | 4680 |
| ggagagtgcc catattgctt tacccactgt gaaccgacag | 4720 |
| aaactgcaat tcaggcacat tacaaagttt gtcaagccac | 4760 |
| ccaccgattc agagaagatt taaaaaagac tgtaactcct | 4800 |
| caaaatattg ggccaggctg ttaccgaaca ctaaatcttt | 4840 |
| ttaggtataa aagtaggtgt tatattctga caatgtggac | 4880 |
| tcttcttctc attattgaat ccatcctctg ggcagcaagt | 4920 |

-continued

| | |
|---|---|
| gcagcagaaa tccccettgt ccctctctgg acagataatg | 4960 |
| ctcatggcgt tgggagtgtt cctatgcata cggatcttga | 5000 |
| attagacttc tctttgccat ccagttctaa gtacacatac | 5040 |
| aaaagacatc tcacaaaccc agttaatgac caacagagtg | 5080 |
| tctcattgca tatagaaatt gaaagtcaag gcattggtgc | 5120 |
| tgctgttcat catcttggac attggtatga tgcaagattg | 5160 |
| aatctaaaaa cctcatttca ttgttatggt gcctgcacaa | 5200 |
| aatatcaata cccatggcac actgcaaaat gccattttga | 5240 |
| gaaagattat gagtatgaaa atagctgggc ttgcaacccc | 5280 |
| ccagattgcc caggggttgg tacaggttgt actgcttgtg | 5320 |
| gattatatct agatcaattg aagccggtag gaacagcctt | 5360 |
| taaaattata agtgtaagat acagtagaaa agtgtgcgtg | 5400 |
| cagtttggtg aagaacacct ttgtaaaaca attgatatga | 5440 |
| atgattgctt tgtgactagg catgccaaaa tatgtataat | 5480 |
| tgggactgta tctaagtttt ctcaaggtga cactctacta | 5520 |
| tttctggggc ccatggaagg aggtggtata atctttaaac | 5560 |
| actggtgtac atctacctgt cactttggag accctggtga | 5600 |
| tgtcatgggt ccaaaagata aaccatttat ttgccctgaa | 5640 |
| ttcccagggc aatttaggaa aaaatgtaac tttgccacaa | 5680 |
| ctccagtttg tgaatatgat ggaaacatta tatcaggcta | 5720 |
| taagaaagta cttgcaacaa ttgattcttt ccaatcattt | 5760 |
| aacacaagca atatacactt cactgatgag agaattgaat | 5800 |
| ggagagaccc tgatggcatg cttcgggatc atattaatat | 5840 |
| tgttatttct aaagatattg attttgaaaa tttggctgag | 5880 |
| aatccttgta agtagggct ccaggcagca aacatagaag | 5920 |
| gtgcctgggg ttcaggtgtc gggtttacac tcacatgcaa | 5960 |
| ggtgtctctc acagaatgcc caacatttct tacatcaata | 6000 |
| aaggcctgtg acatggcaat ttgttatggt gcagaaagtg | 6040 |
| tgacactctc acgaggacaa aatactgtca aaattaccgg | 6080 |
| gaaaggtggc catagtggtt cttcattcaa atgctgtcat | 6120 |
| gggaaagaat gttcatcaac tggcctccaa gccagtgcac | 6160 |
| cacatctgga taaggtaaat ggtatctctg agttagaaaa | 6200 |
| cgagaaagtt tatgatgacg gtgcacctga atgtggcatt | 6240 |
| acttgttggt ttaaaaaatc aggtgaatgg gttatgggta | 6280 |
| taatcaatgg gaactgggtt gtcctaattg tcttgtgtgt | 6320 |
| actgctgctc ttttctctta tcctgttgag catcttgtgt | 6360 |
| cctgttagaa agcataaaaa atcataaatc ccacctaaca | 6400 |
| atcttcacat catgtatcga ttttcaaaca ctttatcatt | 6440 |
| tagaacttaa cttggcacta ctatctgata actgactttc | 6480 |
| attttttattt ttatatggat taattactaa aaaaaatact | 6520 |

| | |
|---|---|
| ctctcgtgcc gaattcgata tcaagcttat cgataccgtc | 6560 |
| gacctcgagg gggggcccgg tacccgggat cctcgcaatc | 6600 |
| cctaggagga ttaggcaagg gcttgagctc acgctcttgt | 6640 |
| gagggacaga aatacaatca ggggcagtat atgaatactc | 6680 |
| catggagaaa cccagatcta cgtatgatca gcctcgactg | 6720 |
| tgccttctag ttgccagcca tctgttgttt gcccctcccc | 6760 |
| cgtgccttcc ttgaccctgg aaggtgccac tcccactgtc | 6800 |
| cttcctaat aaaatgagga aattgcatcg cattgtctga | 6840 |
| gtaggtgtca ttctattctg gggggtgggg tggggcagga | 6880 |
| cagcaagggg gaggattggg aagacaatag caggcatgct | 6920 |
| ggggatgcgg tgggctctat ggcttctgag gcggaaagaa | 6960 |
| ccagctgggg ctcgacagct cgactctaga attgcttcct | 7000 |
| cgctcactga ctcgctgcgc tcggtcgttc ggctgcggcg | 7040 |
| agcggtatca gctcactcaa aggcggtaat acggttatcc | 7080 |
| acagaatcag gggataacgc aggaaagaac atgtgagcaa | 7120 |
| aaggccagca aaaggccagg aaccgtaaaa aggccgcgtt | 7160 |
| gctggcgttt ttccataggc tccgcccccc tgacgagcat | 7200 |
| cacaaaaatc gacgctcaag tcagaggtgg cgaaacccga | 7240 |
| caggactata aagataccag gcgtttcccc ctggaagctc | 7280 |
| cctcgtgcgc tctcctgttc cgaccctgcc gcttaccgga | 7320 |
| tacctgtccg cctttctccc ttcgggaagc gtggcgcttt | 7360 |
| ctcaatgctc acgctgtagg tatctcagtt cggtgtaggt | 7400 |
| cgttcgctcc aagctgggct gtgtgcacga accccccgtt | 7440 |
| cagcccgacc gctgcgcctt atccggtaac tatcgtcttg | 7480 |
| agtccaaccc ggtaagacac gacttatcgc cactggcagc | 7520 |
| agccactggt aacaggatta gcagagcgag gtatgtaggc | 7560 |
| ggtgctacag agttcttgaa gtggtggcct aactacggct | 7600 |
| acactagaag gacagtattt ggtatctgcg ctctgctgaa | 7640 |
| gccagttacc ttcggaaaaa gagttggtag ctcttgatcc | 7680 |
| ggcaaacaaa ccaccgctgg tagcggtggt ttttttgttt | 7720 |
| gcaagcagca gattacgcgc agaaaaaaag gatctcaaga | 7760 |
| agatcctttg atcttttcta cggggtctga cgctcagtgg | 7800 |
| aacgaaaact cacgttaagg gattttggtc atcagattat | 7840 |
| caaaaggat cttcacctag atccttttaa attaaaaatg | 7880 |
| aagttttaaa tcaatctaaa gtatatatga gtaaacttgg | 7920 |
| tctgacagtt accaatgctt aatcagtgag gcacctatct | 7960 |
| cagcgatctg tctatttcgt tcatccatag ttgcctgact | 8000 |
| c | 8001 |

<210> SEQ ID NO 4

<211> LENGTH: 6050
<212> TYPE: DNA
<213> ORGANISM: Artificial sequence
<220> FEATURE:
<223> OTHER INFORMATION: pWRG-SEO-S = Seoul hantavirus S segment, strain SR-11, subcloned into DNA vector pWRG7077

<400> SEQUENCE: 4

| | |
|---|---|
| gggggggggg ggcgctgagg tctgcctcgt gaagaaggtg | 40 |
| ttgctgactc ataccaggcc tgaatcgccc catcatccag | 80 |
| ccagaaagtg agggagccac ggttgatgag agctttgttg | 120 |
| taggtggacc agttggtgat tttgaacttt tgctttgcca | 160 |
| cggaacggtc tgcgttgtcg ggaagatgcg tgatctgatc | 200 |
| cttcaactca gcaaaagttc gatttattca acaaagccgc | 240 |
| cgtcccgtca agtcagcgta atgctctgcc agtgttacaa | 280 |
| ccaattaacc aattctgatt agaaaaactc atcgagcatc | 320 |
| aaatgaaact gcaatttatt catatcagga ttatcaatac | 360 |
| catatttttg aaaaagccgt ttctgtaatg aaggagaaaa | 400 |
| ctcaccgagg cagttccata ggatggcaag atcctggtat | 440 |
| cggtctgcga ttccgactcg tccaacatca atacaaccta | 480 |
| ttaatttccc ctcgtcaaaa ataaggttat caagtgagaa | 520 |
| atcaccatga gtgacgactg aatccggtga gaatggcaaa | 560 |
| agcttatgca tttctttcca gacttgttca acaggccagc | 600 |
| cattacgctc gtcatcaaaa tcactcgcat caaccaaacc | 640 |
| gttattcatt cgtgattgcg cctgagcgag acgaaatacg | 680 |
| cgatcgctgt taaaggaca attacaaaca ggaatcgaat | 720 |
| gcaaccggcg caggaacact gccagcgcat caacaatatt | 760 |
| ttcacctgaa tcaggatatt cttctaatac ctggaatgct | 800 |
| gttttcccgg ggatcgcagt ggtgagtaac catgcatcat | 840 |
| caggagtacg gataaaatgc ttgatggtcg aagaggcat | 880 |
| aaattccgtc agccagttta gtctgaccat ctcatctgta | 920 |
| acatcattgg caacgctacc tttgccatgt ttcagaaaca | 960 |
| actctggcgc atcgggcttc ccatacaatc gatagattgt | 1000 |
| cgcacctgat tgcccgacat tatcgcgagc ccatttatac | 1040 |
| ccatataaat cagcatccat gttggaattt aatcgcggcc | 1080 |
| tcgagcaaga cgtttcccgt tgaatatggc tcataacacc | 1120 |
| ccttgtatta ctgtttatgt aagcagacag ttttattgtt | 1160 |
| catgatgata tatttttatc ttgtgcaatg taacatcaga | 1200 |
| gattttgaga cacaacgtgg ctttcccccc cccccggca | 1240 |
| tgcctgcagg tcgacataaa tcaatattgg ctattggcca | 1280 |
| ttgcatacgt tgtatctata tcataatatg tacatttata | 1320 |
| ttggctcatg tccaatatga ccgccatgtt gacattgatt | 1360 |
| attgactagt tattaatagt aatcaattac ggggtcatta | 1400 |

| | |
|---|---|
| gttcatagcc catatatgga gttccgcgtt acataactta | 1440 |
| cggtaaatgg cccgcctcgt gaccgcccaa cgacccccgc | 1480 |
| ccattgacgt caataatgac gtatgttccc atagtaacgc | 1520 |
| caatagggac tttccattga cgtcaatggg tggagtattt | 1560 |
| acggtaaact gcccacttgg cagtacatca agtgtatcat | 1600 |
| atgccaagtc cggcccccta ttgacgtcaa tgacggtaaa | 1640 |
| tggcccgcct ggcattatgc ccagtacatg accttacggg | 1680 |
| actttcctac ttggcagtac atctacgtat tagtcatcgc | 1720 |
| tattaccatg gtgatgcggt tttggcagta caccaatggg | 1760 |
| cgtggatagc ggtttgactc acggggattt ccaagtctcc | 1800 |
| accccattga cgtcaatggg agtttgtttt ggcaccaaaa | 1840 |
| tcaacgggac tttccaaaat gtcgtaataa ccccgcccg | 1880 |
| ttgacgcaaa tgggcggtag gcgtctacgg tgggaggtct | 1920 |
| atataagcag agctcgttta gtgaaccgtc agatcgcctg | 1960 |
| gagacgccat ccacgctgtt ttgacctcca tagaagacac | 2000 |
| cgggaccgat ccagcctccg cggccgggaa cggtgcattg | 2040 |
| gaacgcggat tccccgtgcc aagagtgacgt aagtaccgc | 2080 |
| ctatagactc tataggcaca ccctttggc tcttatgcat | 2120 |
| gctatactgt ttttggcttg ggcctatac accccgctc | 2160 |
| cttatgctat aggtgatggt atagcttagc ctataggtgt | 2200 |
| gggttattga ccattattga ccactcccct attggtgacg | 2240 |
| atactttcca ttactaatcc ataacatggc tctttgccac | 2280 |
| aactatctct attggctata tgccaatact ctgtccttca | 2320 |
| gagactgaca cggactctgt attttttacag gatggggtcc | 2360 |
| catttattat ttacaaattc acatatacaa caacgccgtc | 2400 |
| ccccgtgccc gcagttttta ttaaacatag cgtgggatct | 2440 |
| ccacgcgaat ctcgggtacg tgttccggac atgggctctt | 2480 |
| ctccggtagc ggcggagctt ccacatccga gccctggtcc | 2520 |
| catgcctcca gcggctcatg gtcgctcggc agctccttgc | 2560 |
| tcctaacagt ggaggccaga cttaggcaca gcacaatgcc | 2600 |
| caccaccacc agtgtgccgc acaaggccgt ggcggtaggg | 2640 |
| tatgtgtctg aaaatgagct cggagattgg gctcgcaccg | 2680 |
| tgacgcagat ggaagactta aggcagcggc agaagaagat | 2720 |
| gcaggcagct gagttgttgt attctgataa gagtcagagg | 2760 |
| taactcccgt tgcggtgctg ttaacggtgg agggcagtgt | 2800 |
| agtctgagca gtactcgttg ctgccgcgcg cgccaccaga | 2840 |
| cataatagct gacagactaa cagactgttc ctttccatgg | 2880 |
| gtcttttctg cagtcaccgt ccaagcttgc ggccaattcg | 2920 |
| gcacgagaga gtagtagact ccctaaagag ctactacact | 2960 |
| aacaagaaaa atggcaacta tggaagaaat ccagagagaa | 3000 |

|  |  |
|---|---|
| atcagtgctc acgaggggca gcttgtgata gcacgccaga | 3040 |
| aggtcaagga tgcagaaaag cagtatgaga aggatcctga | 3080 |
| tgacttaaac aagagggcac tgcatgatcg ggagagtgtc | 3120 |
| gcagcttcaa tacaatcaaa aattgatgaa ttgaagcgcc | 3160 |
| aacttgccga cagattgcag cagggaagaa catccgggca | 3200 |
| ggaccgggat cctacagggg tagagccagg tgatcatctt | 3240 |
| aaggaaagat cagcactaag ctacgggaat acactggacc | 3280 |
| tgaatagtct tgacattgat gaacctacag gacagacagc | 3320 |
| tgattggctg accataattg tctatctgac atcattcgtg | 3360 |
| gtcccgatca tcttgaaggc actgtacatg ttaacaacac | 3400 |
| gaggtaggca gacttcaaag gacaacaagg ggatgaggat | 3440 |
| cagattcaag gatgacagct catatgagga tgtcaatgga | 3480 |
| atcagaaagc ccaaacatct gtatgtgtca atgccaaacg | 3520 |
| cccaatccag catgaaggct gaagagataa caccaggaag | 3560 |
| attccgcact gcagtatgtg gactatatcc tgcacagata | 3600 |
| aaggcaagga atatggtaag ccctgtcatg agtgtagttg | 3640 |
| ggttcttggc actggcaaaa gactggacat cgagaattga | 3680 |
| agaatggctc ggtgcaccct gcaaattcat ggcggagtct | 3720 |
| cttattgccg ggagtttatc tgggaatcct gtgaatcgtg | 3760 |
| actatatcag acagagacaa ggtgcacttg cagggatgga | 3800 |
| gccaaaggaa tttcaagccc tcaggcaaca ttcaaaggat | 3840 |
| gctggatgta cactagttga acatattgag tcaccatcat | 3880 |
| caatatgggt gtttgctggg gcccctgata ggtgtccacc | 3920 |
| aacatgcttg tttgtcggag ggatggctga attaggtgcc | 3960 |
| ttcttttcta tacttcagga tatgaggaac acaatcatgg | 4000 |
| cttcaaaaac tgtgggcaca gctgatgaaa agcttcgaaa | 4040 |
| gaaatcatca ttctatcaat catacctcag acgcacacaa | 4080 |
| tcaatgggaa tacaactgga ccagaggata attgttatgt | 4120 |
| ttatggttgc ctggggaaag gaggcagtgg acaacttcca | 4160 |
| tctcggtgat gacatggatc cagagcttcg tagcctggct | 4200 |
| cagatcttga ttgaccagaa agtgaaggaa atctcaaacc | 4240 |
| aggaacctat gaaattataa gtacataaat atataatcaa | 4280 |
| tactaactat aggttaagaa atactaatca ttagttaata | 4320 |
| agaatataga tttattgaat aatcatatta aataattagg | 4360 |
| taagttaact agtatttagt taagttagct aattgattta | 4400 |
| tatgattgtc acaattaaat gtaatcataa gcacaatcac | 4440 |
| tgccatgtat aatcacgggt atacgggtgg ttttcatatg | 4480 |
| gggaacaggg tgggcttagg gccaggtcac cttaagtgac | 4520 |
| cttttttttgt atatatggat gtagatttca attgatcgaa | 4560 |

| | |
|---|---|
| tactaatcct actgtcctct tttcttttcc tttctccttc | 4600 |
| tttactaaca aactacctcg tgccgaattg gccgcggatc | 4640 |
| ctcgcaatcc ctaggaggat taggcaaggg cttgagctca | 4680 |
| cgctcttgtg agggacagaa atacaatcag gggcagtata | 4720 |
| tgaatactcc atggagaaac ccagatctac gtatgatcag | 4760 |
| cctcgactgt gccttctagt tgccagccat ctgttgtttg | 4800 |
| cccctccccc gtgccttcct tgaccctgga aggtgccact | 4840 |
| cccactgtcc tttcctaata aaatgaggaa attgcatcgc | 4880 |
| attgtctgag taggtgtcat tctattctgg ggggtggggt | 4920 |
| ggggcaggac agcaagggggg aggattggga agacaatagc | 4960 |
| aggcatgctg gggatgcggt gggctctatg gcttctgagg | 5000 |
| cggaaagaac cagctggggc tcgacagctc gactctagaa | 5040 |
| ttgcttcctc gctcactgac tcgctgcgct cggtcgttcg | 5080 |
| gctgcggcga gcggtatcag ctcactcaaa ggcggtaata | 5120 |
| cggttatcca cagaatcagg ggataacgca ggaaagaaca | 5160 |
| tgtgagcaaa aggccagcaa aaggccagga accgtaaaaa | 5200 |
| ggccgcgttg ctggcgtttt tccataggct ccgcccccct | 5240 |
| gacgagcatc acaaaaatcg acgctcaagt cagaggtggc | 5280 |
| gaaacccgac aggactataa agataccagg cgtttccccc | 5320 |
| tggaagctcc ctcgtgcgct ctcctgttcc gaccctgccg | 5360 |
| cttaccggat acctgtccgc ctttctccct tcgggaagcg | 5400 |
| tggcgctttc tcaatgctca cgctgtaggt atctcagttc | 5440 |
| ggtgtaggtc gttcgctcca agctgggctg tgtgcacgaa | 5480 |
| ccccccgttc agcccgaccg ctgcgcctta tccggtaact | 5520 |
| atcgtcttga gtccaacccg gtaagacacg acttatcgcc | 5560 |
| actggcagca gccactggta acaggattag cagagcgagg | 5600 |
| tatgtaggcg gtgctacaga gttcttgaag tggtggccta | 5640 |
| actacggcta cactagaagg acagtatttg gtatctgcgc | 5680 |
| tctgctgaag ccagttacct tcggaaaaag agttggtagc | 5720 |
| tcttgatccg gcaaacaaac caccgctggt agcggtggtt | 5760 |
| tttttgtttg caagcagcag attacgcgca gaaaaaaagg | 5800 |
| atctcaagaa gatcctttga tcttttctac ggggtctgac | 5840 |
| gctcagtgga acgaaaactc acgttaaggg attttggtca | 5880 |
| tgagattatc aaaaaggatc ttcacctaga tccttttaaa | 5920 |
| ttaaaaatga agttttaaat caatctaaag tatatatgag | 5960 |
| taaacttggt ctgacagtta ccaatgctta atcagtgagg | 6000 |
| cacctatctc agcgatctgt ctatttcgtt catccatagt | 6040 |
| tgcctgactc | 6050 |

<210> SEQ ID NO 5
<211> LENGTH: 80

```
<212> TYPE: DNA
<213> ORGANISM: Artificial sequence
<220> FEATURE:
<223> OTHER INFORMATION: Sequence from plasmid pWRG/SEO-M in Figure 9A

<400> SEQUENCE: 5
gcggccgcgg atctgcagga attcggcacg agagtagtag                              40
actccgcaag aaacagcagt taaagaacaa taggatcatg                              80

<210> SEQ ID NO 6
<211> LENGTH: 24
<212> TYPE: DNA
<213> ORGANISM: Artificial sequence
<220> FEATURE:
<223> OTHER INFORMATION: Sequence of 24 bp extraneous sequence

<400> SEQUENCE: 6
ggatctgcag gaattcggca cgag                                               24

<210> SEQ ID NO 7
<211> LENGTH: 7807
<212> TYPE: DNA
<213> ORGANISM: Artificial sequence
<220> FEATURE:
<223> OTHER INFORMATION: Sequence of plasmid pWRG/HTN-M(x)

<400> SEQUENCE: 7
gggggggggg ggcgctgagg tctgcctcgt gaagaaggtg                              40
ttgctgactc ataccaggcc tgaatcgccc catcatccag                              80
ccagaaagtg agggagccac ggttgatgag agctttgttg                             120
taggtggacc agttggtgat tttgaacttt tgctttgcca                             160
cggaacggtc tgcgttgtcg ggaagatgcg tgatctgatc                             200
cttcaactca gcaaaagttc gatttattca acaaagccgc                             240
cgtcccgtca agtcagcgta atgctctgcc agtgttacaa                             280
ccaattaacc aattctgatt agaaaaactc atcgagcatc                             320
aaatgaaact gcaatttatt catatcagga ttatcaatac                             360
catatttttg aaaaagccgt ttctgtaatg aaggagaaaa                             400
ctcaccgagg cagttccata ggatggcaag atcctggtat                             440
cggtctgcga ttccgactcg tccaacatca atacaaccta                             480
ttaatttccc ctcgtcaaaa ataaggttat caagtgagaa                             520
atcaccatga gtgacgactg aatccggtga gaatggcaaa                             560
agcttatgca tttctttcca gacttgttca acaggccagc                             600
cattacgctc gtcatcaaaa tcactcgcat caaccaaacc                             640
gttattcatt cgtgattgcg cctgagcgag acgaaatacg                             680
cgatcgctgt taaaggaca attacaaaca ggaatcgaat                              720
gcaaccggcg caggaacact gccagcgcat caacaatatt                             760
ttcacctgaa tcaggatatt cttctaatac ctggaatgct                             800
gttttcccgg ggatcgcagt ggtgagtaac catgcatcat                             840
caggagtacg gataaaatgc ttgatggtcg aagaggcat                              880 aaattccgtc agccagttta gtctgaccat ctcatctgta                             920
```

| | |
|---|---|
| acatcattgg caacgctacc tttgccatgt ttcagaaaca | 960 |
| actctggcgc atcgggcttc ccatacaatc gatagattgt | 1000 |
| cgcacctgat tgcccgacat tatcgcgagc ccatttatac | 1040 |
| ccatataaat cagcatccat gttggaattt aatcgcggcc | 1080 |
| tcgagcaaga cgtttcccgt tgaatatggc tcataacacc | 1120 |
| ccttgtatta ctgtttatgt aagcagacag ttttattgtt | 1160 |
| catgatgata tattttatc ttgtgcaatg taacatcaga | 1200 |
| gattttgaga cacaacgtgg ctttcccccc cccccggca | 1240 |
| tgcctgcagg tcgacaatat tggctattgg ccattgcata | 1280 |
| cgttgtatct atatcataat atgtacattt atattggctc | 1320 |
| atgtccaata tgaccgccat gttgacattg attattgact | 1360 |
| agttattaat agtaatcaat tacggggtca ttagttcata | 1400 |
| gcccatatat ggagttccgc gttacataac ttacggtaaa | 1440 |
| tggcccgcct ggctgaccgc ccaacgaccc ccgcccattg | 1480 |
| acgtcaataa tgacgtatgt tcccatagta acgccaatag | 1520 |
| ggactttcca ttgacgtcaa tgggtggagt atttacggta | 1560 |
| aactgcccac ttggcagtac atcaagtgta tcatatgcca | 1600 |
| agtccgcccc ctattgacgt caatgacggt aaatggcccg | 1640 |
| cctggcatta tgcccagtac atgaccttac gggactttcc | 1680 |
| tacttggcag tacatctacg tattagtcat cgctattacc | 1720 |
| atggtgatgc ggttttggca gtacaccaat gggcgtggat | 1760 |
| agcggtttga ctcacgggga tttccaagtc tccaccccat | 1800 |
| tgacgtcaat gggagtttgt tttggcacca aaatcaacgg | 1840 |
| gactttccaa aatgtcgtaa taaccccgcc ccgttgacgc | 1880 |
| aaatgggcgg taggcgtgta cggtgggagg tctatataag | 1920 |
| cagagctcgt ttagtgaacc gtcagatcgc ctggagacgc | 1960 |
| catccacgct gttttgacct gcatcgaaga caccgggacc | 2000 |
| gatccagcct ccgcggccgg gaacggtgca ttggaacgcg | 2040 |
| gattccccgt gccaagagtg acgtaagtac cgcctataga | 2080 |
| ctctataggc acaccccttt ggctcttatg catgctatac | 2120 |
| tgtttttggc ttggggccta tacacccccg cttccttatg | 2160 |
| ctataggtga tggtatagct tagcctatag gtgtgggtta | 2200 |
| ttgaccatta ttgaccactc ccctattggt gacgatactt | 2240 |
| tccattacta atccataaca tggctctttg ccacaactat | 2280 |
| ctctattggc tatatgccaa tactctgtcc ttcagagact | 2320 |
| gacacggact ctgtattttt acaggatggg gtcccattta | 2360 |
| ttatttacaa attcacatat acaacaacgc cgtcccccgt | 2400 |
| gcccgcagtt tttattaaac atagcgtggg atctccacgc | 2440 |
| gaatctcggg tacgtgttcc ggacatgggc tcttctccgg | 2480 |
| tagcggcgga gcttccacat ccgagccctg gtcccatgcc | 2520 |

|  |  |
|---|---|
| tccagcggct catggtcgct cggcagctcc ttgctcctaa | 2560 |
| cagtggaggc cagacttagg cacagcacaa tgcccaccac | 2600 |
| caccagtgtg ccgcacaagg ccgtggcggt agggtatgtg | 2640 |
| tctgaaaatg agctcggaga ttgggctcgc accgctgacg | 2680 |
| cagatggaag acttaaggca gcggcagaag aagatgcagg | 2720 |
| cagctgagtt gttgtattct gataagagtc agaggtaact | 2760 |
| cccgttgcgg tgctgttaac ggtggagggc agtgtagtct | 2800 |
| gagcagtact cgttgctgcc gcgcgcgcca ccagacataa | 2840 |
| tagctgacag actaacagac tgttcctttc catgggtctt | 2880 |
| ttctgcagtc accgtccaag cttgcggccg cggatctgca | 2920 |
| ggaattcggc acgagagtag tagactccgc aagaaacagc | 2960 |
| agtcaatcag caacatgggg atatggaagt ggctagtgat | 3000 |
| ggccagttta gtatggcctg ttttgacact gagaaatgtc | 3040 |
| tatgacatga aaattgagtg cccccataca gtaagttttg | 3080 |
| gggaaaacag tgtgataggt tatgtagaat taccccccgt | 3120 |
| gccattggcc gacacagcac agatggtgcc tgagagttct | 3160 |
| tgtagcatgg ataatcacca atcgttgaat acaataacaa | 3200 |
| aatataccca agtaagttgg agaggaaagg ctgatcagtc | 3240 |
| acagtctagt caaaattcat ttgagacagt gtccactgaa | 3280 |
| gttgacttga aggaacatg tgctctaaaa cacaaaatgg | 3320 |
| tggaagaatc ataccgtagt aggaaatcag taacctgtta | 3360 |
| cgacctgtct tgcaatagca cttactgcaa gccaacacta | 3400 |
| tacatgattg taccaattca tgcatgcaat atgatgaaaa | 3440 |
| gctgtttgat tgcattggga ccatacagag tacaggtggt | 3480 |
| ttatgagaga tcttattgca tgacaggagt cctgattgaa | 3520 |
| gggaaatgct ttgtcccaga tcaaagtgtg gtcagtatta | 3560 |
| tcaagcatgg gatctttgat attgcaagtg ttcatattgt | 3600 |
| atgtttcttt gttgcagtta aagggaatac ttataaaatt | 3640 |
| tttgaacagg ttaagaaatc cttttgaatca acatgcaatg | 3680 |
| atacagagaa taaagtgcaa ggatattata tttgtattgt | 3720 |
| aggggggaaac tctgcaccaa tatatgttcc aacacttgat | 3760 |
| gatttcagat ccatggaagc atttacagga atcttcagat | 3800 |
| caccacatgg ggaagatcat gatctggctg gagaagaaat | 3840 |
| tgcatcttat tctatagtcg gacctgccaa tgcaaaagtt | 3880 |
| cctcatagtg ctagctcaga tacattgagc ttgattgcct | 3920 |
| attcaggtat accatcttat tcttccctta gcatcctaac | 3960 |
| aagttcaaca gaagctaagc atgtattcag ccctgggttg | 4000 |
| ttcccaaaac ttaatcacac aaattgtgat aaaagtgcca | 4040 |
| taccactcat atggactggg atgattgatt tacctggata | 4080 |

| | |
|---|---|
| ctacgaagct gtccacccctt gtacagtttt ttgcgtatta | 4120 |
| tcaggtcctg gggcatcatg tgaagccttt tctgaaggcg | 4160 |
| ggattttcaa cataacctct cccatgtgct tagtgtcaaa | 4200 |
| acaaaatcga ttccggttaa cagaacagca agtgaatttt | 4240 |
| gtgtgtcagc gagtggacat ggacattgtt gtgtactgca | 4280 |
| acgggcagag gaaagtaata ttaacaaaaa ctctagttat | 4320 |
| tggacagtgt atatatacta taacaagctt attctcatta | 4360 |
| ctacctggag tagcacattc tattgctgtt gaattgtgtg | 4400 |
| tacctgggtt ccatggttgg gccacagctg ctctgcttgt | 4440 |
| tacattctgt ttcggatggg ttcttatacc agcaattaca | 4480 |
| tttatcatac taacagtcct aaagttcatt gctaatattt | 4520 |
| ttcacacaag taatcaagag aataggctaa atcagtact | 4560 |
| tagaaagata aggaagagt ttgaaaaaac aaaaggctca | 4600 |
| atggtatgtg atgtctgcaa gtatgagtgt gaaacctata | 4640 |
| aagaattaaa ggcacacggg gtatcatgcc cccaatctca | 4680 |
| atgtccttac tgttttactc attgtgaacc cacagaagca | 4720 |
| gcattccaag ctcattacaa ggtatgccaa gttactcaca | 4760 |
| gattcaggga tgatctaaag aaaactgtta ctccctcaaaa | 4800 |
| ttttacacca ggatgttacc ggacactaaa tttatttaga | 4840 |
| tacaaaagca ggtgctacat ctttacaatg tggatatttc | 4880 |
| ttcttgtctt agaatccata ctgtgggctg caagtgcatc | 4920 |
| agagacacca ttaactcctg tctggaatga caatgcccat | 4960 |
| ggggtaggtt ctgttcctat gcatacagat ttagagcttg | 5000 |
| atttctcttt aacatccagt tccaagtata cataccgtag | 5040 |
| gaggttaaca aacccacttg aggaagcaca atccattgac | 5080 |
| ctacatattg aaatagaaga acagacaatt ggtgttgatg | 5120 |
| tgcatgctct aggacactgg tttgatggtc gtcttaacct | 5160 |
| taaaacatcc tttcactgtt atggtgcttg tacaaagtat | 5200 |
| gaatacccttt ggcatactgc aaagtgccac tatgaaagag | 5240 |
| attaccaata tgagacgagc tggggttgta atccatcaga | 5280 |
| ttgtcctggg gtgggcacag gctgtacagc atgtggttta | 5320 |
| tacctagatc aactgaaacc agttggtagt gcttataaaa | 5360 |
| ttatcacaat aaggtacagc aggagagtct gtgttcagtt | 5400 |
| tgggaggaa aacctttgta agataataga catgaatgat | 5440 |
| tgttttgtat ctaggcatgt taaggtctgc ataattggta | 5480 |
| cagtatctaa attctctcag ggtgataccct tattgttttt | 5520 |
| tggaccgctt gaaggtggtg gtctaatatt taaacactgg | 5560 |
| tgtacatcca catgtcaatt tggtgaccca ggagatatca | 5600 |
| tgagtccaag agacaaaggt ttttttatgcc ctgagtttcc | 5640 |
| aggtagtttc aggaagaaat gcaactttgc tactaccccct | 5680 |

```
atttgtgagt atgatggaaa tatggtctca ggttacaaga              5720
aagtgatggc cacaattgat tccttccaat cttttaatac              5760
aagcactatg cacttcactg atgaaaggat agagtggaaa              5800
gaccctgatg gaatgctaag ggaccatata aacattttag              5840
taacgaagga cattgacttt gataaccttg gtgaaaatcc              5880
ttgcaaaatt ggcctacaaa catcttctat tgagggggcc              5920
tggggttctg gtgtggggtt cacattaaca tgtctggtat              5960
cactaacaga atgtcctacc tttttgacct caataaaggc              6000
ttgtgataag gctatctgtt atggtgcaga gagtgtaaca              6040
ttgacaagag gacaaaatac agtcaaggta tcagggaaag              6080
gtggccatag tggttcaaca tttaggtgtt gccatgggga              6120
ggactgttca caaattggac tccatgctgc tgcacctcac              6160
cttgacaagg taaatgggat ttctgagata gaaaatagta              6200
aagtatatga tgatggggca ccgcaatgtg ggataaaatg              6240
ttggtttgtt aaatcagggg aatggatttc agggatattc              6280
agtggtaatt ggattgtact cattgtcctc tgtgtatttc              6320
tattgttctc cttggtttta ctaagcattc tctgtcccgt              6360
aaggaagcat aaaaaatcat agctaaattc tgtgactatc              6400
ctgttcttat gtatagcttt aacatatata ctaatttttta             6440
tattccagta tactctatct aacacactaa aaaaaatagt              6480
agctttctaa ccacaaaacg gatctacgta tgatcagcct              6520
cgactgtgcc ttctagttgc cagccatctg ttgtttgccc              6560
ctcccccgtg ccttccttga ccctggaagg tgccactccc              6600
actgtccttt cctaataaaa tgaggaaatt gcatcgcatt              6640
gtctgagtag gtgtcattct attctggggg gtggggtggg              6680
gcaggacagc aaggggagg attgggaaga caatagcagg               6720
catgctgggg atgcggtggg ctctatggct tctgaggcgg              6760
aaagaaccag ctggggctcg acagctcgac tctagaattg              6800
cttcctcgct cactgactcg ctgcgctcgg tcgttcggct              6840
gcggcgagcg gtatcagctc actcaaaggc ggtaatacgg              6880
ttatccacag aatcagggga taacgcagga agaacatgt               6920
gagcaaaagg ccagcaaaag gccaggaacc gtaaaaaggc              6960
cgcgttgctg gcgtttttcc ataggctccg ccccccctgac             7000
gagcatcaca aaaatcgacg ctcaagtcag aggtggcgaa              7040
acccgacagg actataaaga taccaggcgt ttccccctgg              7080
aagctccctc gtgcgctctc ctgttccgac cctgccgctt              7120
accggatacc tgtccgcctt tctcccttcg ggaagcgtgg              7160
cgctttctca tagctcacgc tgtaggtatc tcagttcggt              7200
gtaggtcgtt cgctccaagc tgggctgtgt gcacgaaccc              7240
```

-continued

```
cccgttcagc cgaccgctg cgccttatcc ggtaactatc            7280
gtcttgagtc caacccggta agacacgact tatcgccact            7320
ggcagcagcc actggtaaca ggattagcag agcgaggtat            7360
gtaggcggtg ctacagagtt cttgaagtgg tggcctaact            7400
acggctacac tagaagaaca gtatttggta tctgcgctct            7440
gctgaagcca gttaccttcg gaaaaagagt tggtagctct            7480
tgatccggca aacaaaccac cgctggtagc ggtggttttt            7520
ttgtttgcaa gcagcagatt acgcgcagaa aaaaaggatc            7560
tcaagaagat cctttgatct tttctacggg gtctgacgct            7600
cagtggaacg aaaactcacg ttaagggatt ttggtcatga            7640
gattatcaaa aaggatcttc acctagatcc ttttaaatta            7680
aaaatgaagt tttaaatcaa tctaaagtat atatgagtaa            7720
acttggtctg acagttacca atgcttaatc agtgaggcac            7760
ctatctcagc gatctgtcta tttcgttcat ccatagttgc            7800
ctgactc                                                 7807
```

<210> SEQ ID NO 8
<211> LENGTH: 7913
<212> TYPE: DNA
<213> ORGANISM: Artificial sequence
<220> FEATURE:
<223> OTHER INFORMATION: Sequence of plasmid pWRG/AND-M(x)

<400> SEQUENCE: 8

```
gggggggggg ggcgctgagg tctgcctcgt gaagaaggtg            40
ttgctgactc ataccaggcc tgaatcgccc catcatccag            80
ccagaaagtg agggagccac ggttgatgag agctttgttg            120
taggtggacc agttggtgat tttgaacttt tgctttgcca            160
cggaacggtc tgcgttgtcg ggaagatgcg tgatctgatc            200
cttcaactca gcaaaagttc gatttattca acaaagccgc            240
cgtcccgtca agtcagcgta atgctctgcc agtgttacaa            280
ccaattaacc aattctgatt agaaaaactc atcgagcatc            320
aaatgaaact gcaatttatt catatcagga ttatcaatac            360 catattttg aaaaagccgt ttctgtaatg aaggagaaaa            400
ctcaccgagg cagttccata ggatggcaag atcctggtat            440
cggtctgcga ttccgactcg tccaacatca atacaaccta            480
ttaatttccc ctcgtcaaaa ataaggttat caagtgagaa            520
atcaccatga gtgacgactg aatccggtga gaatggcaaa            560
agcttatgca tttctttcca gacttgttca acaggccagc            600
cattacgctc gtcatcaaaa tcactcgcat caaccaaacc            640
gttattcatt cgtgattgcg cctgagcgag acgaaatacg            680
cgatcgctgt taaaaggaca attacaaaca ggaatcgaat            720
gcaaccggcg caggaacact gccagcgcat caacaatatt            760
ttcacctgaa tcaggatatt cttctaatac ctggaatgct            800
```

-continued

| | |
|---|---|
| gttttcccgg ggatcgcagt ggtgagtaac catgcatcat | 840 |
| caggagtacg gataaaatgc ttgatggtcg gaagaggcat | 880 |
| aaattccgtc agccagttta gtctgaccat ctcatctgta | 920 |
| acatcattgg caacgctacc tttgccatgt ttcagaaaca | 960 |
| actctggcgc atcgggcttc ccatacaatc gatagattgt | 1000 |
| cgcacctgat tgcccgacat tatcgcgagc ccatttatac | 1040 |
| ccatataaat cagcatccat gttggaattt aatcgcggcc | 1080 |
| tcgagcaaga cgtttcccgt tgaatatggc tcataacacc | 1120 |
| ccttgtatta ctgtttatgt aagcagacag ttttattgtt | 1160 |
| catgatgata tatttttatc ttgtgcaatg taacatcaga | 1200 |
| gattttgaga cacaacgtgg ctttcccccc ccccccggca | 1240 |
| tgcctgcagg tcgacaatat ggctattgg ccattgcata | 1280 |
| cgttgtatct atatcataat atgtacattt atattggctc | 1320 |
| atgtccaata tgaccgccat gttgacattg attattgact | 1360 |
| agttattaat agtaatcaat tacggggtca ttagttcata | 1400 |
| gcccatatat ggagttccgc gttacataac ttacggtaaa | 1440 |
| tggcccgcct ggctgaccgc ccaacgaccc ccgcccattg | 1480 |
| acgtcaataa tgacgtatgt tcccatagta acgccaatag | 1520 |
| ggactttcca ttgacgtcaa tgggtggagt atttacggta | 1560 |
| aactgcccac ttggcagtac atcaagtgta tcatatgcca | 1600 |
| agtccgcccc ctattgacgt caatgacggt aaatggcccg | 1640 |
| cctggcatta tgcccagtac atgaccttac gggactttcc | 1680 |
| tacttggcag tacatctacg tattagtcat cgctattacc | 1720 |
| atggtgatgc ggttttggca gtacaccaat gggcgtggat | 1760 |
| agcggtttga ctcacgggga tttccaagtc tccaccccat | 1800 |
| tgacgtcaat gggagtttgt tttggcacca aaatcaacgg | 1840 |
| gactttccaa aatgtcgtaa taaccccgcc ccgttgacgc | 1880 |
| aaatgggcgg taggcgtgta cggtgggagg tctatataag | 1920 |
| cagagctcgt ttagtgaacc gtcagatcgc ctggagacgc | 1960 |
| catccacgct gttttgacct ccatagaaga caccgggacc | 2000 |
| gatccagcct ccgcggccgg gaacggtgca ttggaacgcg | 2040 |
| gattccccgt gccaagagtg acgtaagtac cgcctataga | 2080 |
| ctctataggc acaccccttt ggctcttatg catgctatac | 2120 |
| tgttttggc ttggggccta tacaccccg cttccttatg | 2160 |
| ctataggtga tggtatagct tagcctatag gtgtgggtta | 2200 |
| ttgaccatta ttgaccactc ccctattggt gacgatactt | 2240 |
| tccattacta atccataaca tggctctttg ccacaactat | 2280 |
| ctctattggc tatatgccaa tactctgtcc ttcagagact | 2320 |
| gacacggact ctgtattttt acaggatggg gtcccattta | 2360 |

| | |
|---|---|
| ttatttacaa attcacatat acaacaacgc cgtcccccgt | 2400 |
| gcccgcagtt tttattaaac atagcgtggg atctccacgc | 2440 |
| gaatctcggg tacgtgttcc ggacatgggc tcttctccgg | 2480 |
| tagcggcgga gcttccacat ccgagccctg gtcccatgcc | 2520 |
| tccagcggct catggtcgct cggcagctcc ttgctcctaa | 2560 |
| cagtggaggc cagacttagg cacagcacaa tgcccaccac | 2600 |
| caccagtgtg ccgcacaagg ccgtggcggt agggtatgtg | 2640 |
| tctgaaaatg agctcggaga ttgggctcgc accgctgacg | 2680 |
| cagatggaag acttaaggca gcggcagaag aagatgcagg | 2720 |
| cagctgagtt gttgtattct gataagagtc agaggtaact | 2760 |
| cccgttgcgg tgctgttaac ggtggagggc agtgtagtct | 2800 |
| gagcagtact cgttgctgcc gcgcgcgcca ccagacataa | 2840 |
| tagctgacag actaacagac tgttcctttc catgggtctt | 2880 |
| ttctgcagtc agggtccaag cttgcggccg cggatctgca | 2920 |
| ggaattcggc acgagagtag tagactccgc acgaagaagc | 2960 |
| aaaaaattaa agaagtgagt ttaaaatgga agggtggtat | 3000 |
| ctggttgttc ttggagtctg ctatacgctg acactggcaa | 3040 |
| tgcccaagac catttatgag cttaaaatgg aatgcccgca | 3080 |
| cactgtgggt ctcggtcaag gttacatcat tggctcaaca | 3120 |
| gaactaggtt tgatctcaat tgaggctgca tctgatataa | 3160 |
| agctcgagag ctcttgcaat tttgatcttc atacaacatc | 3200 |
| tatggcccag aagagtttca cccaagttga atggagaaag | 3240 |
| aaaagtgaca caactgatac cacaaatgct gcgtccacta | 3280 |
| cctttgaagc acaaactaaa actgttaacc ttagagggac | 3320 |
| ttgtatactg gcacctgaac tctatgatac attgaagaaa | 3360 |
| gtaaaaaaga cagtcctgtg ctatgatcta acatgtaatc | 3400 |
| aaacacattg tcagccaact gtctatctga ttgcacctgt | 3440 |
| attgacatgc atgtcaataa gaagttgtat ggctagtgtg | 3480 |
| tttacaagca ggattcaggt gatttatgaa aagacacatt | 3520 |
| gtgtaacagg tcagctgatt gagggtcagt gtttcaaccc | 3560 |
| agcacacaca ttgacattat ctcagcctgc tcacacttat | 3600 |
| gatactgtca cccttcctat ctcttgtttt ttcacaccaa | 3640 |
| agaagtcgga gcaactaaaa gttataaaaa catttgaagg | 3680 |
| aattctgacg aagacaggtt gcacggagaa tgcattgcag | 3720 |
| ggttattatg tgtgtttttt agggagtcat tcagaacctt | 3760 |
| taattgttcc gagtttggag gacatacggt ctgctgaagt | 3800 |
| tgttagtagg atgcttgtac acccctagggg agaagaccat | 3840 |
| gatgccatac agaattcaca aagtcactta agaatagtgg | 3880 |
| gacctatcac agcaaaagtg ccatcaacta gttccacaga | 3920 |
| taccctaaag gggacagcct ttgcaggcgt cccaatgtat | 3960 |

```
agctctttat ctacactagt cagaaatgca gacccagaat      4000
ttgtattttc tccaggtata gtacctgaat ctaatcacag      4040
tacatgtgat aagaagacag tacctatcac atggacaggc      4080
tacctaccaa tatcaggtga gatggaaaaa gtgactggat      4120
gtacagtttt ttgtacacta gcaggacctg gtgctagttg      4160
tgaggcctat tctgaaaatg gtatatttaa catcagttct      4200
ccaacatgtc ttgtaaacaa agtccaaaga tttcgtggat      4240
ctgaacagaa aataaatttt atctgtcagc gggtagatca      4280
ggatgttgtt gtatactgca atgggcaaaa gaaagtcata      4320
ttaaccaaaa ctttggttat tgggcagtgt atttatacat      4360
tcacaagcct attttcattg atgcctgatg tagcccactc      4400
attggctgta gaattatgtg tcccgggatt acatgggtgg      4440
gccactgtca tgcttctatc aacattctgc tttgggtggg      4480
tcttgattcc tgcggtcaca ttaataatat taaagtgtct      4520
aagggttttg acgttttctt gttcccatta cactaatgag      4560
tcaaaattta aattcatcct ggaaaaagtt aaaattgaat      4600
accaaaagac tatgggatca atggtgtgcg atgtatgtca      4640
tcatgagtgt gaaacagcaa aagaacttga atcacataga      4680
cagagttgta tcaatggaca atgtccttat tgcatgacaa      4720
taactgaagc aactgaaagt gccttgcaag cccattattc      4760
catttgtaaa ttggcaggaa gatttcagga ggcactgaaa      4800
aagtcactta aaaagccaga ggtaaaaaaa ggttgttaca      4840
gaacactcgg ggtatttaga tataaaagta gatgttatgt      4880
gggtttggta tggtgcctat tgttgacatg tgaaattgtt      4920
atttgggccg caagtgcaga gactccacta atggagtcag      4960
gctggtcaga tacggctcat ggtgttggtg agattccaat      5000
gaagacagac ctcgagctgg acttttcact gccttcttca      5040
tcctcttaca gttataggag aaagctcaca acccagcca       5080
ataaagaaga gtctattccc ttccacttcc agatggaaaa      5120
acaagtaatt catgctgaaa tccaacccct gggtcattgg      5160
atggatgcga catttaatat taagactgca tttcattgtt      5200
atggtgcatg ccagaaatac tcttatccat ggcagacatc      5240
taagtgcttc tttgaaaagg actaccagta tgaaacaggc      5280
tggggctgta atcctggtga ctgcccaggg gttgggactg      5320
gatgcactgc ttgtggtgtt tatctcgata aactaaaatc      5360
tgttgggaag gcctataaga taatttcttt aaaatatacc      5400
agaaaggttt gtattcagtt aggaacagaa caaacttgca      5440
agcatattga tgcaaatgat tgtttagtga caccatctgt      5480
gaaagtttgc atagtgggca cagtttcaaa acttcaacca      5520
```

| | |
|---|---|
| tctgatactc tttttgttctt aggtccacta gaacaagggg | 5560 |
| gaatcattct taagcaatgg tgcacaacat catgtgcatt | 5600 |
| tggggaccct ggtgatatca tgtccactcc cagtggtatg | 5640 |
| aggtgtccag agcacactgg atcatttagg aaaatttgcg | 5680 |
| gttttgctac tacaccagtt tgtgaatatc aaggaaatac | 5720 |
| catttctgga tataaaagaa tgatggcaac aaaagattca | 5760 |
| ttccaatcat ttaacttaac agaacctcac atcacaacaa | 5800 |
| acaagcttga atggatcgac ccagatggga atacaagaga | 5840 |
| ccacgtaaac cttgtcttaa atagagatgt ctcatttcag | 5880 |
| gatttaagtg ataaccccctg taaagtagac ctacacacac | 5920 |
| aagcaataga aggggcatgg ggttctggtg tagggtttac | 5960 |
| actcacatgt actgtcggat taacagagtg cccaagtttt | 6000 |
| atgacatcaa ttaaggcatg tgacctagct atgtgttatg | 6040 |
| gatcaacagt aacaaacctt gccagggggct ctaatacagt | 6080 |
| gaaagtagtt ggtaaaggag gccattcagg gtcctcattt | 6120 |
| aaatgctgtc atgatacaga ttgctcctct gaaggtttac | 6160 |
| ttgcatcagc ccctcatctt gagagggtaa caggattcaa | 6200 |
| tcaaattgat tcagataagg tttatgatga tggtgcacca | 6240 |
| ccttgcacat tcaaatgctg gttcactaag tcaggtgagt | 6280 |
| ggcttcttgg gatcttaaac gggaattgga ttgttgttgt | 6320 |
| agtgcttgtt gtgatactca ttctctctat cataatgttc | 6360 |
| agtgttttgt gtcccaggag agggcacaag aaaactgtct | 6400 |
| aagcattgac ctcaactcct acattagatc atatacattt | 6440 |
| atgcacttcc tcatatttag ctgcactaag atattaataa | 6480 |
| actctagtta ttgactttat aagattatta tggaactaac | 6520 |
| ctcacttaaa aaaacaaat actttactca tatataactc | 6560 |
| catattctct taccgaggat tttgttcctg cggagcatac | 6600 |
| tactaggatc tacgtatgat cagcctcgac tgtgccttct | 6640 |
| agttgccagc catctgttgt ttgcccctcc cccgtgcctt | 6680 |
| ccttgacccct ggaaggtgcc actcccactg tcctttccta | 6720 |
| ataaaatgag gaaattgcat cgcattgtct gagtaggtgt | 6760 |
| cattctattc tgggggggtgg ggtggggcag gacagcaagg | 6800 |
| gggaggattg ggaagacaat agcaggcatg ctggggatgc | 6840 |
| ggtgggctct atggcttctg aggcggaaag aaccagctgg | 6880 |
| ggctcgacag ctcgactcta gaattgcttc ctcgctcact | 6920 |
| gactcgctgc gctcggtcgt tcggctgcgg cgagcggtat | 6960 |
| cagctcactc aaaggcggta atacggttat ccacagaatc | 7000 |
| aggggataac gcaggaaaga acatgtgagc aaaaggccag | 7040 |
| caaaaggcca ggaaccgtaa aaaggccgcg ttgctggcgt | 7080 |
| ttttccatag gctccgcccc cctgacgagc atcacaaaaa | 7120 |

-continued

| | |
|---|---|
| tcgacgctca agtcagaggt ggcgaaaccc gacaggacta | 7160 |
| taaagatacc aggcgtttcc ccctggaagc tccctcgtgc | 7200 |
| gctctcctgt tccgaccctg ccgcttaccg gatacctgtc | 7240 |
| cgccttctc ccttcgggaa gcgtggcgct ttctcatagc | 7280 |
| tcacgctgta ggtatctcag ttcggtgtag gtcgttcgct | 7320 |
| ccaagctggg ctgtgtgcac gaaccccccg ttcagcccga | 7360 |
| ccgctgcgcc ttatccggta actatcgtct tgagtccaac | 7400 |
| ccggtaagac acgacttatc gccactggca gcagccactg | 7440 |
| gtaacaggat tagcagagcg aggtatgtag gcggtgctac | 7480 |
| agagttcttg aagtggtggc ctaactacgg ctacactaga | 7520 |
| agaacagtat ttggtatctg cgctctgctg aagccagtta | 7560 |
| ccttcgaaaa aagagttggt agctcttgat ccggcaaaca | 7600 |
| aaccaccgct ggtagcggtg ttttttttgt ttgcaagcag | 7640 |
| cagattacgc gcagaaaaaa aggatctcaa gaagatcctt | 7680 |
| tgatcttttc tacggggtct gacgctcagt ggaacgaaaa | 7720 |
| ctcacgttaa gggattttgg tcatgagatt atcaaaaagg | 7760 |
| atcttcacct agatcctttt aaattaaaaa tgaagtttta | 7800 |
| aatcaatcta agtatatat gagtaaactt ggtctgacag | 7840 |
| ttaccaatgc ttaatcagtg aggcacctat ctcagcgatc | 7880 |
| tgtctatttc gttcatccat agttgcctga ctc | 7913 |

<210> SEQ ID NO 9
<211> LENGTH: 13464
<212> TYPE: DNA
<213> ORGANISM: Artificial sequence
<220> FEATURE:
<223> OTHER INFORMATION: Sequence of plasmid pWRG/HA-M

<400> SEQUENCE: 9

| | |
|---|---|
| gggggggggg ggcgctgagg tctgcctcgt gaagaaggtg | 40 |
| ttgctgactc ataccaggcc tgaatcgccc catcatccag | 80 |
| ccagaaagtg agggagccac ggttgatgag agctttgttg | 120 |
| taggtggacc agttggtgat tttgaactt tgctttgcca | 160 |
| cggaacggtc tgcgttgtcg ggaagatgcg tgatctgatc | 200 |
| cttcaactca gcaaaagttc gatttattca acaaagccgc | 240 |
| cgtcccgtca agtcagcgta atgctctgcc agtgttacaa | 280 |
| ccaattaacc aattctgatt agaaaaactc atcgagcatc | 320 |
| aaatgaaact gcaatttatt catatcagga ttatcaatac | 360 |
| catattttg aaaaagccgt ttctgtaatg aaggagaaaa | 400 |
| ctcaccgagg cagttccata ggatggcaag atcctggtat | 440 |
| cggtctgcga ttccgactcg tccaacatca atacaaccta | 480 |
| ttaatttccc ctcgtcaaaa ataaggttat caagtgagaa | 520 |
| atcaccatga gtgacgactg aatccggtga gaatggcaaa | 560 |

|   |   |
|---|---|
| agcttatgca tttctttcca gacttgttca acaggccagc | 600 |
| cattacgctc gtcatcaaaa tcactcgcat caaccaaacc | 640 |
| gttattcatt cgtgattgcg cctgagcgag acgaaatacg | 680 |
| cgatcgctgt taaaaggaca attacaaaca ggaatcgaat | 720 |
| gcaaccggcg caggaacact gccagcgcat caacaatatt | 760 |
| ttcacctgaa tcaggatatt cttctaatac ctggaatgct | 800 |
| gttttcccgg ggatcgcagt ggtgagtaac catgcatcat | 840 |
| caggagtacg gataaaatgc ttgatggtcg gaagaggcat | 880 |
| aaattccgtc agccagttta gtctgaccat ctcatctgta | 920 |
| acatcattgg caacgctacc tttgccatgt ttcagaaaca | 960 |
| actctggcgc atcgggcttc ccatacaatc gatagattgt | 1000 |
| cgcacctgat tgcccgacat tatcgcgagc ccatttatac | 1040 |
| ccatataaat cagcatccat gttggaattt aatcgcggcc | 1080 |
| tcgagcaaga cgtttcccgt tgaatatggc tcataacacc | 1120 |
| ccttgtatta ctgtttatgt aagcagacag ttttattgtt | 1160 |
| catgatgata tatttttatc ttgtgcaatg taacatcaga | 1200 |
| gattttgaga cacaacgtgg cttttccccc ccccccggca | 1240 |
| tgcctgcagg tcgacaatat tggctattgg ccattgcata | 1280 |
| cgttgtatct atatcataat atgtacattt atattggctc | 1320 |
| atgtccaata tgaccgccat gttgacattg attattgact | 1360 |
| agttattaat agtaatcaat tacggggtca ttagttcata | 1400 |
| gcccatatat ggagttccgc gttacataac ttacggtaaa | 1440 |
| tggcccgcct ggctgaccgc ccaacgaccc ccgcccattg | 1480 |
| acgtcaataa tgacgtatgt tcccatagta acgccaatag | 1520 |
| ggactttcca ttgacgtcaa tgggtggagt atttacggta | 1560 |
| aactgcccac ttggcagtac atcaagtgta tcatatgcca | 1600 |
| agtccgcccc ctattgacgt caatgacggt aaatggcccg | 1640 |
| cctggcatta tgcccagtac atgaccttac gggactttcc | 1680 |
| tacttggcag tacatctacg tattagtcat cgctattacc | 1720 |
| atggtgatgc ggttttggca gtacaccaat gggcgtggat | 1760 |
| agcggtttga ctcacgggga tttccaagtc tccaccccat | 1800 |
| tgacgtcaat gggagtttgt tttggcacca aaatcaacgg | 1840 |
| gactttccaa aatgtcgtaa taaccccgcc ccgttgacgc | 1880 |
| aaatgggcgg taggcgtgta cggtgggagg tctatataag | 1920 |
| cagagctcgt ttagtgaacc gtcagatcgc ctggagacgc | 1960 |
| catccacgct gttttgacct ccatagaaga caccgggacc | 2000 |
| gatccagcct ccgcggccgg gaacggtgca ttggaacgcg | 2040 |
| gattccccgt gccaagagtg acgtaagtac cgcctataga | 2080 |
| ctctataggc acacccttt ggctcttatg catgctatac | 2120 |
| tgtttttggc ttggggccta tacacccccg cttccttatg | 2160 |

```
ctataggtga tggtatagct tagcctatag gtgtgggtta        2200
ttgaccatta ttgaccactc ccctattggt gacgatactt        2240
tccattacta atccataaca tggctctttg ccacaactat        2280
ctctattggc tatatgccaa tactctgtcc ttcagagact        2320
gacacggact ctgtattttt acaggatggg gtcccattta        2360
ttatttacaa attcacatat acaacaacgc cgtcccccgt        2400
gcccgcagtt tttattaaac atagcgtggg atctccacgc        2440
gaatctcggg tacgtgttcc ggacatgggc tcttctccgg        2480
tagcggcgga gcttccacat ccgagccctg gtcccatgcc        2520
tccagcggct catggtcgct cggcagctcc ttgctcctaa        2560
cagtggaggc cagacttagg cacagcacaa tgcccaccac        2600
caccagtgtg ccgcacaagg ccgtggcggt agggtatgtg        2640
tctgaaaatg agctcggaga ttgggctcgc accgctgacg        2680
cagatggaag acttaaggca gcggcagaag aagatgcagg        2720
cagctgagtt gttgtattct gataagagtc agaggtaact        2760
cccgttgcgg tgctgttaac ggtggagggc agtgtagtct        2800
gagcagtact cgttgctgcc gcgcgcgcca ccagacataa        2840
tagctgacag actaacagac tgttcctttc catgggtctt        2880
ttctgcagtc accgtccaag cttgcggccg cggatctgca        2920
ggaattcggc acgagagtag tagactccgc aagaaacagc        2960
agtcaatcag caccatgggg atatggaagt ggctagtgat        3000
ggccagttta gtatggcctg ttttgacact gagaaatgtc        3040
tatgacatga aaattgagtg ccccccataca gtaagttttg       3080
gggaaaacag tgtgataggt tatgtagaat tacccccccgt       3120
gccattggcc gacacagcac agatggtgcc tgagagttct       3160
tgtagcatgg ataatcacca atcgttgaat acaataacaa        3200
aatatacccca agtaagttgg agaggaaagg ctgatcagtc       3240
acagtctagt caaaattcat ttgagacagt gtccactgaa        3280
gttgacttga aggaacatg tgctctaaaa cacaaaatgg         3320
tggaagaatc ataccgtagt aggaaatcag taacctgtta        3360
cgacctgtct tgcaatagca cttactgcaa gccaacacta        3400
tacatgattg taccaattca tgcatgcaat atgatgaaaa        3440
gctgtttgat tgcattggga ccatacagag tacaggtggt        3480
ttatgagaga tcttattgca tgacaggagt cctgattgaa        3520
gggaaatgct ttgtcccaga tcaaagtgtg gtcagtatta        3560
tcaagcatgg gatctttgat attgcaagtg ttcatattgt        3600
atgtttcttt gttgcagtta aagggaatac ttataaaatt        3640
tttgaacagg ttaagaaatc ctttgaatca acatgcaatg        3680
atacagagaa taaagtgcaa ggatattata tttgtattgt        3720
```

-continued

| | |
|---|---|
| aggggggaaac tctgcaccaa tatatgttcc aacacttgat | 3760 |
| gatttcagat ccatggaagc atttacagga atcttcagat | 3800 |
| caccacatgg ggaagatcat gatctggctg gagaagaaat | 3840 |
| tgcatcttat tctatagtcg gacctgccaa tgcaaaagtt | 3880 |
| cctcatagtg ctagctcaga tacattgagc ttgattgcct | 3920 |
| attcaggtat accatcttat tcttcccctta gcatcctaac | 3960 |
| aagttcaaca gaagctaagc atgtattcag ccctgggttg | 4000 |
| ttcccaaaac ttaatcacac aaattgtgat aaaagtgcca | 4040 |
| taccactcat atggactggg atgattgatt tacctggata | 4080 |
| ctacgaagct gtccacccttt gtacagttttt ttgcgtatta | 4120 |
| tcaggtcctg gggcatcatg tgaagccttt tctgaaggcg | 4160 |
| ggattttcaa cataacctct cccatgtgct tagtgtcaaa | 4200 |
| acaaaatcga ttccggttaa cagaacagca agtgaatttt | 4240 |
| gtgtgtcagc gagtggacat ggacattgtt gtgtactgca | 4280 |
| acgggcagag gaaagtaata ttaacaaaaa ctctagttat | 4320 |
| tggacagtgt atatatacta taacaagctt attctcatta | 4360 |
| ctacctggag tagcacattc tattgctgtt gaattgtgtg | 4400 |
| tacctgggtt ccatggttgg gccacagctg ctctgcttgt | 4440 |
| tacattctgt ttcggatggg ttcttatacc agcaattaca | 4480 |
| tttatcatac taacagtcct aaagttcatt gctaatattt | 4520 |
| ttcacacaag taatcaagag aataggctaa atcagtact | 4560 |
| tagaaagata aggaagagt ttgaaaaaac aaaaggctca | 4600 |
| atggtatgtg atgtctgcaa gtatgagtgt gaaacctata | 4640 |
| aagaattaaa ggcacacggg gtatcatgcc cccaatctca | 4680 |
| atgtccttac tgtttttactc attgtgaacc cacagaagca | 4720 |
| gcattccaag ctcattacaa ggtatgccaa gttactcaca | 4760 |
| gattcaggga tgatctaaag aaaactgtta ctcctcaaaa | 4800 |
| ttttacacca ggatgttacc ggacactaaa tttatttaga | 4840 |
| tacaaaagca ggtgctacat ctttacaatg tggatatttc | 4880 |
| ttcttgtctt agaatccata ctgtgggctg caagtgcatc | 4920 |
| agagacacca ttaactcctg tctggaatga caatgcccat | 4960 |
| ggggtaggtt ctgttcctat gcatacagat ttagagcttg | 5000 |
| atttctcttt aacatccagt tccaagtata cataccgtag | 5040 |
| gaagttaaca aacccacttg aggaagcaca atccattgac | 5080 |
| ctacatattg aaatagaaga acagacaatt ggtgttgatg | 5120 |
| tgcatgctct aggacactgg tttgatggtc gtcttaacct | 5160 |
| taaaacatcc tttcactgtt atggtgcttg tacaaagtat | 5200 |
| gaatacccctt ggcatactgc aaagtgccac tatgaaagag | 5240 |
| attaccaata tgagacgagc tggggttgta atccatcaga | 5280 |
| ttgtcctggg gtgggcacag gctgtacagc atgtggttta | 5320 |

-continued

| | |
|---|---|
| tacctagatc aactgaaacc agttggtagt gcttataaaa | 5360 |
| ttatcacaat aaggtacagc aggagagtct gtgttcagtt | 5400 |
| tggggaggaa aacctttgta agataataga catgaatgat | 5440 |
| tgttttgtat ctaggcatgt taaggtctgc ataattggta | 5480 |
| cagtatctaa attctctcag ggtgatacct tattgttttt | 5520 |
| tggaccgctt gaaggtggtg gtctaatatt taaacactgg | 5560 |
| tgtacatcca catgtcaatt tggtgaccca ggagatatca | 5600 |
| tgagtccaag agacaaaggt tttttatgcc ctgagtttcc | 5640 |
| aggtagtttc aggaagaaat gcaactttgc tactacccct | 5680 |
| atttgtgagt atgatggaaa tatggtctca ggttacaaga | 5720 |
| aagtgatggc gacaattgat tccttccaat cttttaatac | 5760 |
| aagcactatg cacttcactg atgaaaggat agagtggaaa | 5800 |
| gacccctgatg aatgctaag ggaccatata acattttag | 5840 |
| taacgaagga cattgacttt gataaccttg gtgaaaatcc | 5880 |
| ttgcaaaatt ggcctacaaa catcttctat tgagggggcc | 5920 |
| tggggttctg gtgtggggtt cacattaaca tgtctggtat | 5960 |
| cactaacaga atgtcctacc ttttttgacct caataaaggc | 6000 |
| ttgtgataag gctatctgtt atggtgcaga gagtgtaaca | 6040 |
| ttgacaagag gacaaaatac agtcaaggta tcagggaaag | 6080 |
| gtggccatag tggttcaaca tttaggtgtt gccatgggga | 6120 |
| ggactgttca caaattggac tccatgctgc tgcacctcac | 6160 |
| cttgacaagg taaatgggat ttctgagata gaaaatagta | 6200 |
| aagtatatga tgatggggca ccgcaatgtg ggataaaatg | 6240 |
| ttggtttgtt aaatcagggg aatggatttc agggatattc | 6280 |
| agtggtaatt ggattgtact cattgtcctc tgtgtatttc | 6320 |
| tattgttctc cttggtttta ctaagcattc tctgtcccgt | 6360 |
| aaggaagcat aaaaaatcat agctaaattc tgtgactatc | 6400 |
| ctgttcttat gtatagcttt aacatatata ctaatttta | 6440 |
| tattccagta tactctatct aacacactaa aaaaaatagt | 6480 |
| agctttctaa ccacaaaacg gatctacgta tgatcagcct | 6520 |
| cgactgtgcc ttctagttgc cagccatctg ttgtttgccc | 6560 |
| ctcccccgtg ccttccttga ccctggaagg tgccactccc | 6600 |
| actgtccttt cctaataaaa tgaggaaatt gcatcgcatt | 6640 |
| gtctgagtag gtgtcattct attctggggg gtggggtggg | 6680 |
| gcaggacagc aagggggagg attgggaaga caatagcagg | 6720 |
| catgctgggg atgcggtggg ctctatggct tctgaggcgg | 6760 |
| aaagaaccag ctggggctcg acagctcgac tctagagcag | 6800 |
| gtcgacaata ttggctattg gccattgcat acgttgtatc | 6840 |
| tatatcataa tatgtacatt tatattggct catgtccaat | 6880 |

| | |
|---|---|
| atgaccgcca tgttgacatt gattattgac tagttattaa | 6920 |
| tagtaatcaa ttacggggtc attagttcat agcccatata | 6960 |
| tggagttccg cgttacataa cttacggtaa atggcccgcc | 7000 |
| tggctgaccg cccaacgacc cccgcccatt gacgtcaata | 7040 |
| atgacgtatg ttcccatagt aacgccaata gggactttcc | 7080 |
| attgacgtca atgggtggag tatttacggt aaactgccca | 7120 |
| cttggcagta catcaagtgt atcatatgcc aagtccgccc | 7160 |
| cctattgacg tcaatgacgg taaatggccc gcctggcatt | 7200 |
| atgcccagta catgacctta cgggactttc ctacttggca | 7240 |
| gtacatctac gtattagtca tcgctattac catggtgatg | 7280 |
| cggttttggc agtacaccaa tgggcgtgga tagcggtttg | 7320 |
| actcacgggg atttccaagt ctccaccccc ttgacgtcaa | 7360 |
| tgggagtttg ttttggcacc aaaatcaacg ggactttcca | 7400 |
| aaatgtcgta ataaccccgc cccgttgacg caaatgggcg | 7440 |
| gtaggcgtgt acggtgggag gtctatataa gcagagctcg | 7480 |
| tttagtgaac cgtcagatcg cctggagacg ccatccacgc | 7520 |
| tgttttgacc tccatagaag acaccgggac cgatccagcc | 7560 |
| tccgcggccg ggaacggtgc attggaacgc ggattccccg | 7600 |
| tgccaagagt gacgtaagta ccgcctatag actctatagg | 7640 |
| cacaccccatt tggctcttat gcatgctata ctgttttttgg | 7680 |
| cttggggcct atacaccccc gcttccttat gctataggtg | 7720 |
| atggtatagc ttagcctata ggtgtgggtt attgaccatt | 7760 |
| attgaccact cccctattgg tgacgatact ttccattact | 7800 |
| aatccataac atggctcttt gccacaacta tctctattgg | 7840 |
| ctatatgcca atactctgtc cttcagagac tgacacggac | 7880 |
| tctgtatttt tacaggatgg ggtcccattt attatttaca | 7920 |
| aattcacata tacaacaacg ccgtcccccg tgcccgcagt | 7960 |
| ttttattaaa catagcgtgg gatctccacg cgaatctcgg | 8000 |
| gtacgtgttc cggacatggg ctcttctccg gtagcggcgg | 8040 |
| agcttccaca tccgagcccct ggtcccatgc ctccagcggc | 8080 |
| tcatggtcgc tcggcagctc cttgctccta acagtggagg | 8120 |
| ccagacttag gcacagcaca atgcccacca ccaccagtgt | 8160 |
| gccgcacaag gccgtggcgg tagggtatgt gtctgaaaat | 8200 |
| gagctcggag attgggctcg caccgctgac gcagatggaa | 8240 |
| gacttaaggc agcggcagaa gaagatgcag gcagctgagt | 8280 |
| tgttgtattc tgataagagt cagaggtaac tcccgttgcg | 8320 |
| gtgctgttaa cggtggaggg cagtgtagtc tgagcagtac | 8360 |
| tcgttgctgc cgcgcgcgcc accagacata atagctgaca | 8400 |
| gactaacaga ctgttccttt ccatgggtct tttctgcagt | 8440 |
| caccgtccaa gcttgcggcc gcggatctgc aggaattcgg | 8480 |

```
cacgagagta gtagactccg cacgaagaag caaaaaatta              8520
aagaagtgag tttaaaatgg aagggtggta tctggttgtt              8560
cttggagtct gctatacgct gacactggca atgcccaaga              8600
ccatttatga gcttaaaatg gaatgcccgc acactgtggg              8640
tctcggtcaa ggttacatca ttggctcaac agaactaggt              8680
ttgatctcaa ttgaggctgc atctgatata aagctcgaga              8720
gctcttgcaa ttttgatctt catacaacat ctatggccca              8760
gaagagtttc acccaagttg aatggagaaa gaaaagtgac              8800
acaactgata ccacaaatgc tgcgtccact acctttgaag              8840
cacaaactaa aactgttaac cttagaggga cttgtatact              8880
ggcacctgaa ctctatgata cattgaagaa agtaaaaaag              8920
acagtcctgt gctatgatct aacatgtaat caaacacatt              8960
gtcagccaac tgtctatctg attgcacctg tattgacatg              9000
catgtcaata agaagttgta tggctagtgt gtttacaagc              9040
aggattcagg tgatttatga aaagacacat tgtgtaacag              9080
gtcagctgat tgagggtcag tgtttcaacc cagcacacac              9120
attgacatta tctcagcctg ctcacactta tgatactgtc              9160
acccttccta tctcttgttt tttcacacca aagaagtcgg              9200
agcaactaaa agttataaaa acatttgaag gaattctgac              9240
gaagacaggt tgcacggaga atgcattgca gggttattat              9280
gtgtgttttt taggaagtca ttcagaacct ttaattgttc              9320
cgagtttgga ggacatacgg tctgctgaag ttgttagtag              9360
gatgcttgta caccctaggg gagaagacca tgatgccata              9400
cagaattcac aaagtcactt aagaatagtg ggacctatca              9440
cagcaaaagt gccatcaact agttccacag atacccctaaa            9480 ggggacagcc tttgcaggcg tcccaatgta tagctctta              9520 tctacactag tcagaaatgc agacccagaa tttgtatttt              9560
ctccaggtat agtacctgaa tctaatcaca gtacatgtga              9600
taagaagaca gtacctatca catggacagg ctacctacca              9640
atatcaggtg agatggaaaa agtgactgga tgtacagttt              9680
tttgtacact agcaggacct ggtgctagtt gtgaggccta              9720
ttctgaaaat ggtatatttta acatcagttc tccaacatgt              9760
cttgtaaaca agtccaaag atttcgtgga tctgaacaga              9800
aaataaattt tatctgtcag cgggtagatc aggatgttgt              9840
tgtatactgc aatgggcaaa agaaagtcat attaaccaaa              9880
actttggtta ttgggcagtg tatttataca ttcacaagcc              9920 tatttcatt gatgcctgat gtagcccact cattggctgt               9960
agaattatgt gtcccgggat tacatgggtg ggccactgtc              10000
atgcttctat caacattctg ctttgggtgg gtcttgattc              10040
```

| | |
|---|---|
| ctgcggtcac attaataata ttaaagtgtc taagggtttt | 10080 |
| gacgttttct tgttcccatt acactaatga gtcaaaattt | 10120 |
| aaattcatcc tggaaaaagt taaaattgaa taccaaaaga | 10160 |
| ctatgggatc aatggtgtgc gatgtatgtc atcatgagtg | 10200 |
| tgaaacagca aaagaacttg aatcacatag acagagttgt | 10240 |
| atcaatggac aatgtcctta ttgcatgaca ataactgaag | 10280 |
| caactgaaag tgccttgcaa gcccattatt ccatttgtaa | 10320 |
| attggcagga agatttcagg aggcactgaa aaagtcactt | 10360 |
| aaaaagccag aggtaaaaaa aggttgttac agaacactcg | 10400 |
| gggtatttag atataaaagt agatgttatg tgggtttggt | 10440 |
| atggtgccta ttgttgacat gtgaaattgt tatttgggcc | 10480 |
| gcaagtgcag agactccact aatggagtca ggctggtcag | 10520 |
| atacggctca tggtgttggt gagattccaa tgaagacaga | 10560 |
| cctcgagctg gacttttcac tgccttcttc atcctcttac | 10600 |
| agttatagga gaaagctcac aaacccagcc aataaagaag | 10640 |
| agtctattcc cttccacttc cagatggaaa aacaagtaat | 10680 |
| tcatgctgaa atccaacccc tgggtcattg gatggatgcg | 10720 |
| acatttaata ttaagactgc atttcattgt tatggtgcat | 10760 |
| gccagaaata ctcttatcca tggcagacat ctaagtgctt | 10800 |
| ctttgaaaag gactaccagt atgaaacagg ctggggctgt | 10840 |
| aatcctggtg actgcccagg ggttgggact ggatgcactg | 10880 |
| cttgtggtgt ttatctcgat aaactaaaat ctgttgggaa | 10920 |
| ggcctataag ataatttctt taaaatatac cagaaaggtt | 10960 |
| tgtattcagt taggaacaga acaaacttgc aagcatattg | 11000 |
| atgcaaatga ttgtttagtg acaccatctg tgaaagtttg | 11040 |
| catagtgggc acagtttcaa aacttcaacc atctgatact | 11080 |
| cttttgttct taggtccact agaacaaggg ggaatcattc | 11120 |
| ttaagcaatg gtgcacaaca tcatgtgcat ttggggaccc | 11160 |
| tggtgatatc atgtccactc ccagtggtat gaggtgtcca | 11200 |
| gagcacactg gatcatttag gaaaatttgc ggttttgcta | 11240 |
| ctacaccagt ttgtgaatat caaggaaata ccatttctgg | 11280 |
| atataaaaga atgatggcaa caaaagattc attccaatca | 11320 |
| tttaacttaa cagaacctca catcacaaca aacaagcttg | 11360 |
| aatggatcga cccagatggg aatacaagag accacgtaaa | 11400 |
| ccttgtctta aatagagatg tctcatttca ggatttaagt | 11440 |
| gataacccct gtaaagtaga cctacacaca caagcaatag | 11480 |
| aaggggcatg gggttctggt gtagggttta cactcacatg | 11520 |
| tactgtcgga ttaacagagt gcccaagttt tatgacatca | 11560 |
| attaaggcat gtgacctagc tatgtgttat ggatcaacag | 11600 |
| taacaaacct tgccagggc tctaatacag tgaaagtagt | 11640 |

-continued

| | |
|---|---|
| tggtaaagga ggccattcag ggtcctcatt taaatgctgt | 11680 |
| catgatacag attgctcctc tgaaggttta cttgcatcag | 11720 |
| cccctcatct tgagagggta acaggattca atcaaattga | 11760 |
| ttcagataag gtttatgatg atggtgcacc accttgcaca | 11800 |
| ttcaaatgct ggttcactaa gtcaggtgag tggcttcttg | 11840 |
| ggatcttaaa cgggaattgg attgttgttg tagtgcttgt | 11880 |
| tgtgatactc attctctcta tcataatgtt cagtgttttg | 11920 |
| tgtcccagga gagggcacaa gaaaactgtc taagcattga | 11960 |
| cctcaactcc tacattagat catatacatt tatgcacttc | 12000 |
| ctcatattta gctgcactaa gatattaata aactctagtt | 12040 |
| attgacttta taagattatt atggaactaa cctcacttaa | 12080 |
| aaaaaacaaa tactttactc atatataact ccatattctc | 12120 |
| ttaccgagga ttttgttcct gcggagcata ctactaggat | 12160 |
| ctacgtatga tcagcctcga ctgtgccttc tagttgccag | 12200 |
| ccatctgttg tttgccccctc ccccgtgcct tccttgaccc | 12240 |
| tggaaggtgc cactcccact gtcctttcct aataaaatga | 12280 |
| ggaaattgca tcgcattgtc tgagtaggtg tcattctatt | 12320 |
| ctgggggtg gggtggggca ggacagcaag ggggaggatt | 12360 |
| gggaagacaa tagcaggcat gctggggatg cggtgggctc | 12400 |
| tatggcttct gaggcggaaa gaaccagctg gggctcgaca | 12440 |
| gctcgactct agaattgctt cctcgctcac tgactcgctg | 12480 |
| cgctcggtcg ttcggctgcg gccagcggta tcagctcact | 12520 |
| caaaggcggt aatacggtta tccacagaat caggggataa | 12560 |
| cgcaggaaag aacatgtgag caaaaggcca gcaaaaggcc | 12600 |
| aggaaccgta aaaaggccgc gttgctggcg ttttttccata | 12640 |
| ggctccgccc ccctgacgag catcacaaaa atcgacgctc | 12680 |
| aagtcagagg tggcgaaacc cgacaggact ataaagatac | 12720 |
| caggcgtttc ccctggaag ctccctcgtg cgctctcctg | 12760 |
| ttccgaccct gccgcttacc ggatacctgt ccgcctttct | 12800 |
| cccttcggga agcgtggcgc tttctcatag ctcacgctgt | 12840 |
| aggtatctca gttcggtgta ggtcgttcgc tccaagctgg | 12880 |
| gctgtgtgca cgaacccccc gttcagcccg accgctgcgc | 12920 |
| cttatccggt aactatcgtc ttgagtccaa cccggtaaga | 12960 |
| cacgacttat cgccactggc agcagccact ggtaacagga | 13000 |
| ttagcagagc gaggtatgta ggcggtgcta cagagttctt | 13040 |
| gaagtggtgg cctaactacg gctacactag aagaacagta | 13080 |
| tttggtatct gcgctctgct gaagccagtt accttcggaa | 13120 |
| aaagagttgg tagctcttga tccggcaaac aaaccaccgc | 13160 |
| tggtagcggt ggtttttttg tttgcaagca gcagattacg | 13200 |

| | |
|---|---|
| cgcagaaaaa aaggatctca agaagatcct ttgatctttt | 13240 |
| ctacgggtc tgacgctcag tggaacgaaa actcacgtta | 13280 |
| agggattttg gtcatgagat tatcaaaaag gatcttcacc | 13320 |
| tagatccttt taaattaaaa atgaagtttt aaatcaatct | 13360 |
| aaagtatata tgagtaaact tgttctgaca gttaccaatg | 13400 |
| cttaatcagt gaggcaccta tctcagcgat ctgtctattt | 13440 |
| cgttcatcca tagttgcctg actc | 13464 |

<210> SEQ ID NO 10
<211> LENGTH: 34
<212> TYPE: DNA
<213> ORGANISM: Artificial sequence
<220> FEATURE:
<223> OTHER INFORMATION: primer 0

<400> SEQUENCE: 10
gcgcgcggcc gcagtagtag actccgcaag aaac          34

<210> SEQ ID NO 11
<211> LENGTH: 31
<212> TYPE: DNA
<213> ORGANISM: Artificial sequence
<220> FEATURE:
<223> OTHER INFORMATION: primer

<400> SEQUENCE: 11
gcgcggatcc cgggtaccgg gcccccctg g              31

<210> SEQ ID NO 12
<211> LENGTH: 62
<212> TYPE: DNA
<213> ORGANISM: Artificial sequence
<220> FEATURE:
<223> OTHER INFORMATION: primer 1-24

<400> SEQUENCE: 12
ggccgcggcc gcggatctgc aggaattcgg cacgagagta    40
gtagactccg caagaaacag ca                       62

<210> SEQ ID NO 13
<211> LENGTH: 62
<212> TYPE: DNA
<213> ORGANISM: Artificial sequence
<220> FEATURE:
<223> OTHER INFORMATION: primer 24-1

<400> SEQUENCE: 13
ggccgcggcc gcgagcacgg cttaaggacg tctaggagta    40
gtagtctccg caagaaacag ca                       62

<210> SEQ ID NO 14
<211> LENGTH: 50
<212> TYPE: DNA
<213> ORGANISM: Artificial sequence
<220> FEATURE:
<223> OTHER INFORMATION: primer 1-12

<400> SEQUENCE: 14
ggccgcggcc gcattcggca cgagagtagt agactccgca    40
agaaacagca                                     50

<210> SEQ ID NO 15
<211> LENGTH: 50
<212> TYPE: DNA
<213> ORGANISM: Artificial sequence
<220> FEATURE:
<223> OTHER INFORMATION: primer 13-24

<400> SEQUENCE: 15
ggccgcggcc gcggatctgc aggaagtagt agactccgca          40
agaaacagca                                           50

<210> SEQ ID NO 16
<211> LENGTH: 62
<212> TYPE: DNA
<213> ORGANISM: Artificial sequence
<220> FEATURE:
<223> OTHER INFORMATION: primer 1-24*

<400> SEQUENCE: 16
ggccgcggcc gcggatctgc ccgaattcgg caccagagta          40
gtagactccg caagaaacag ca                             62

<210> SEQ ID NO 17
<211> LENGTH: 46
<212> TYPE: DNA
<213> ORGANISM: Artificial sequence
<220> FEATURE:
<223> OTHER INFORMATION: primer 1-8

<400> SEQUENCE: 17
ggccgcggcc gcggatctgc agtagtagac tccgcaagaa          40
acagca                                               46

<210> SEQ ID NO 18
<211> LENGTH: 31
<212> TYPE: DNA
<213> ORGANISM: Artificial sequence
<220> FEATURE:
<223> OTHER INFORMATION: primer SEOMX

<400> SEQUENCE: 18
gcgcggatcc agattgggag atagaagaga g                   31

<210> SEQ ID NO 19
<211> LENGTH: 29
<212> TYPE: DNA
<213> ORGANISM: Artificial sequence
<220> FEATURE:
<223> OTHER INFORMATION: primer M5B

<400> SEQUENCE: 19
tcaggactcc tgtcatgcaa taagatctc                      29

<210> SEQ ID NO 20
<211> LENGTH: 30
<212> TYPE: DNA
<213> ORGANISM: Artificial sequence
<220> FEATURE:
<223> OTHER INFORMATION: primer HTNMX

<400> SEQUENCE: 20
gcgcggatcc gtttgtggtt agaaagctac                     30

<210> SEQ ID NO 21
<211> LENGTH: 61
<212> TYPE: DNA
<213> ORGANISM: Artificial sequence
<220> FEATURE:
<223> OTHER INFORMATION: primer SN-Fj

<400> SEQUENCE: 21
ggccgcggcc gcggatctgc aggaattcgg cacgagagta          40
gtagactccg cacgaagaag c                              61

<210> SEQ ID NO 22
<211> LENGTH: 32
<212> TYPE: DNA
<213> ORGANISM: Artificial sequence
<220> FEATURE:
<223> OTHER INFORMATION: primer PUUM-R

<400> SEQUENCE: 22
gcgcggatcc tagtagtatg ctccgcagga ac                  32

EXTRANEOUS DNA SEQUENCE THAT FACILITATES HANTAVIRUS GENE EXPRESSION

This is a continuation-in-part application of U.S. Ser. No. 09/491,974 (now abandoned) filed on Jan. 27, 2000 which claims priority from U.S. Provisional Application Ser. No. 60/117,680 filed Jan. 29, 1999. This application also claims benefit from an earlier filed Provisional Application Ser. No. 60/367,128 filed on Mar. 22, 2002 and Provisional Application Ser. No. 60/398,985 filed on Jul. 26, 2002.

INTRODUCTION

Currently, there are four known hantaviruses associated with hemorrhagic fever with renal syndrome (HFRS): Hantaan virus (HTNV), Dobrava-Belgrade virus (DOBV), Puumala virus (PUUV), and Seoul virus (SEOV). Because distinct hantaviruses are usually carried by only one principal rodent host species, their distribution is generally limited to the range of that host (reviewed in Schmaljohn and Hjelle, 1997, *Emerg. Infect. Dis.* 3, 95–104). HTNV, carried by *Apodemus agrarius*, is found in Asia; DOBV, carried by *Apodemus flavicollis*, and PUUV, carried by *Clethrionomys glareolus*, are found in Europe. SEOV is more widely disseminated than any other recognized hantavirus because its host, the common urban rat (*Rattus norvegicus*), is found throughout the world.

New-World hantaviruses have been associated with outbreaks of a highly lethal disease, hantavirus pulmonary syndrome (HPS), in the Americas (reviewed in Schmaljohn and Hjelle, 1997, Emerg. Infect Dis. 3, 95–104). The disease is characterized by fever and vascular leakage resulting in non-cardiogenic pulmonary edema followed by shock. Case-fatality for HPS cuased by the most prevalent North American and South American hantaviruses, Sin Nombre virus (SNV) and Andes virus (ANDV), respectively is 30–50%.

Viruses in the Hantavirus genus (family Bunyaviridae) are enveloped and contain a genome comprised of three single-stranded RNA segments designated large (L), medium (M), and small (S) based on size (reviewed in Schmaljohn, 1996, In *The Bunyaviridae* Ed. R. M. Elliott. New York, Plenum Press p. 63–90). The hantavirus L segment encodes the RNA dependent RNA polymerase, M encodes two envelope glycoproteins (G1 and G2), and S encodes the nucleocapsid protein (N).

A number of inactivated HFRS vaccines derived from cell culture or rodent brain were developed and tested in Asia (Lee et al., 1990, *Arch. Virol.,* Suppl. 1, 35–47; Song et al., 1992, *Vaccine* 10, 214–216; Lu et al., 1996, *J. Med. Virol.* 49, 333–335). Drawbacks of these traditional killed-virus vaccines include a requirement for appropriate containment for the growth and manipulation of virus. In order to overcome these drawbacks, vaccine approaches involving recombinant DNA technology were developed including: vaccinia-vectored vaccines (Schmaljohn et al. 1990, *J. Virol.* 64, 3162–3170; Schmaljohn et al. 1992, Vaccine 10, 10–13; Xu et al. 1992, *Am. J. Trop. Med. Hyg.* 47, 397–404), protein subunit vaccines expressed in bacteria or insect cells (Schmaljohn et al. 1990, supra; Yoshimatsu et al., 1993, *Arch. Virol.* 130, 365–376; Lundkvist et al., 1996, *Virology* 216, 397–406), and a hepatitis core antigen-based recombinant vaccine (Ulrich et al., 1998, *Vaccine* 16, 272–280).

Vaccination with vaccinia recombinants expressing the M segment of either HTNV or SEOV elicited neutralizing antibodies and protected rodents against infection with both HTNV and SEOV, suggesting that an immune response to G1-G2 alone can confer protection (Schmaljohn et al. 1990, supra; Xu et al. 1992, supra; Chu et al. 1995, *J. Virol.* 69, 6417–6423). Similarly, vaccination with G1-G2 protein expressed in insect cells (baculovirus recombinant virus system) elicited neutralizing antibodies and protected hamsters from infection with HTNV (Schmaljohn et al. 1990, supra). In both the vaccinia and baculovirus systems, vaccination with G1-G2 provided more complete protection than G1 or G2 alone (Schmaljohn et al. 1990, supra). Neutralizing antibody responses to G1-G2 in the aforementioned vaccine studies correlated with protection, suggesting that neutralizing antibodies play an important role in preventing hantavirus infection. Passive transfer of neutralizing monoclonal antibodies (MAbs) specific to either G1 or G2 protected hamsters against HTNV infection (Schmaljohn et al., 1990, supra; Arikawa et al., 1992, *J. Gen. Virol.* 70, 615–624), supporting the idea that neutralizing antibodies alone can confer protection.

The N protein also plays a role in protecting against hantavirus infection. Vaccination with N expressed in bacteria, insect cells, or as chimeric hepatitis B virus (HBV) core particles protected rodents from hantavirus infection (Schmaljohn et al., 1990, supra; Yoshimatsu et al. 1993, supra; Lundkvist et al., 1996, supra; Ulrich et al., 1998, supra). Vaccination with vaccinia recombinants expressing the S segment were less conclusive. A construct expressing the HTNV S segment did not protect hamsters from HTNV infection, possibly due to low N expression levels (Schmaljohn et al. 1990, supra); and a construct expressing the S segment of SEOV protected three of four gerbils from SEOV infection (Xu et al. 1992, supra).

Similarly, basic research towards a gene-based vaccine that protects against HPS has been ongoing since the isolation of the first HPS-associated hantavirus in the mid 1990s. There are reports that candidate DNA vaccines comprised of around 500 nucleotide stretches of the SNV M gene, or the full-length S gene, are immunogenic in mice (Bharadwaj, et al., 1999, Vaccine 17, 2836, 43) and conferred some protection against infection with SNV in a deer mouse infection model (Bharadwaj, et al., 2002, J. Gen. Virol. 83, 1745–1751). The protection was surmised to be cell-mediated because there was no convincing evidence that these constructs elicited a neutralizing, or otherwise protective, antibody response.

Therefore, it remains unclear whether or not G1 alone, G2 alone, or fragments of the glycoproteins can elicit neutralizing antibody and protect against infection. Vaccination with recombinant baculovirus-infected cell lysates containing G1 or G2 alone, and recombinant vaccinia viruses expressing G1 or G2 alone, failed to elicit neutralizing antibody, and exhibited incomplete protection in a hamster infection model (Schmaljohn et al., 1990). Even though these vaccinia vaccines showed some potential, recombinant vaccinia virus vaccines and vaccinia-based vaccines present disadvantages including the potential for disseminated infection, especially in immunocompromised individuals, since the vaccines consist of live virus. Also, vaccination with these viruses can result in a lesion (pock) that contains infectious virus. Virus from these lesions can be inadvertently spread to other sites (e.g., eyes) or to other individuals. In addition, vaccinia-vectored vaccine are poorly immunogenic in persons previously vaccinated with smallpox vaccine (McClain et al., 2000, J. Med. Virol. 60, 77–85). Other drawbacks of vaccinia-based vaccines include discomfort due to swollen lymphnodes and scarring at the site of inoculation.

SUMMARY OF THE INVENTION

In this report, we describe a new recombinant DNA vaccine approach that involves vaccination with naked DNA expressing individual hantavirus genome segment cDNAs. Naked DNA vaccination involves delivery of plasmid DNA constructs with a gene(s) of interest into the tissue of the vaccinee (reviewed in Robinson and Torres, 1997, *Semin. Immunol.* 9, 271–283; and Gregoriadis, 1998, *Pharm. Res.* 15, 661–670).

This vaccine approach is advantageous over subunit vaccines which do not elicit a cytotoxic response necessary to prevent the establishment of infection or disease. DNA vaccination mimics the de novo antigen production and MHC class I-restricted antigen presentation obtainable with live vaccines, without the risks of pathogenic infection. Also, this DNA vaccine approach allows delivery to mucosal tissues which may aid in conferring resistance to viral introduction since entry of the virus may be through mucosal tissues.

The gene(s) of interest, in our case, a hantavirus genome segment, is controlled by a mammalian or virus promoter (e.g., the cytomegalovirus immediate early promoter) that facilitates expression of the naked DNA gene product(s) within the vaccinee's cells. This intracellular expression can elicit both humoral and cell-mediated immune responses (Robinson and Torres, 1997, supra; and Gregoriadis, 1998, supra). Methods of DNA delivery include needle inoculation, oral or pulmonary delivery, and inoculation by particle bombardment (i.e., gene gun). DNA vaccination by each of these methods elicits protective immunity against many different pathogens including numerous viruses (Robinson and Torres, 1997,supra; and Gregoriadis, 1998, supra). However, neither an immune response against hantaviruses nor protection against hantavirus infection have so far been demonstrated using a DNA vaccine.

In this report, we demonstrate that naked DNA vaccination with the SEOV M or S genome segment elicits SEOV-specific antibody responses in rodents. More importantly, we demonstrate that DNA vaccination with the SEOV M segment elicits neutralizing antibodies and protects hamsters against SEOV infection.

Also in this application we report the development of a HTNV M DNA vaccine. This vaccine expresses the G1 and G2 proteins of HTNV, elicits neutralizing antibodies in hamsters, and protects hamsters against infection with HTNV, SEOV, and DOBV. Furthermore, we demonstrate that the SEOV M, and HTNV M DNA vaccine elicit high-titer neutralizing antibody responses in nonhuman primates.

Additionally, we describe the development and testing of the first ANDV M gene-based DNA vaccine that elicits a neutralizing, or otherwise protective, antibody response. This was an unexpected result since the vaccine is not immunogenic nor protective in hamsters but is immunogenic and protective in rhesus monkeys. In addition, cross protection was evident against two other HPS-associated hantaviruses: Sin Nombre virus and Black Creek Canal virus.

Also described in this application is a Hantaan/Andes dual-M gene hantavirus DNA vaccine containing both the HTNV M gene and the ANDV M gene. This vaccine showed immunogenicity and protection in non-human primates. This is the first DNA vaccine designed to protect against all hantaviruses, both HPRS-associated and HPS-associated, that cause severe disease. The Hantaan/Andes dual-M gene hantavirus DNA vaccine, pWRG/HA-M, was tested for immunogenicity in rhesus macaques. The vaccine elicited an antibody response that neutralized Hantaan virus and Andes virus (see Table 8). In a single hamster experiment, we found that this plasmid was similar to the Andes virus plasmid, in that it did not elicit an antibody response in hamsters. However, the fact it elicits neutralizing antibodies in monkeys suggests it could elicit neutralizing antibodies in humans.

Furthermore, this application also describes a Hantavirus immunoglobulin composition which can be used as a prophylactic or therapeutic effective in preventing onset of hantavirus infection after exposure to hantavirus, and/or in treating hantavirus disease. There is presently no specific drug or immunotherapeutic to treat HPS or HFRS disease or to administer to people with possible hantavirus exposure, or hantavirus disease. The hantavirus immunoglobulin composition of the present invention is composed of polyclonal antiserum from a population of animals/humans vaccinated with a DNA vaccine comprised of a plasmid expressing the Andes virus M gene and/or the Hantaan virus M gene. The polyclonal serum would contain neutralizing antibodies against Andes virus and/or against Hantaan virus. Unlike conventional polyclonal immune serum products, the process used to make this invention (DNA vaccination of primate antibody producing vaccinees) does not involve live virus and does not require the identification of patients who have survived hantavirus disease.

Therefore, it is one object of the present invention to provide a hantavirus DNA vaccine comprising a hantavirus genome segment. More specifically, the present invention relates to an SEOV hantavirus DNA vaccine comprising the SEOV M genome segment specified in SEQ ID NO:1 or comprising the SEOV S segment specified in SEQ ID NO:2. The present invention also relates to a HTNV hantavirus DNA vaccine comprising the HTNV M genome segment specified in extending from 2 to 3565 of genbank sequence accession number M14627. The present invention further relates to an ANDV DNA vaccine comprising the ANDV M genome segment extending from 2 to 3671 of genbank sequence accession number AF291703. The present invention also relates to a HTNV/ANDV DNA vaccine comprising the HTNV M genome segment and the ANDV M genome segment. The hantavirus DNA segments described above can be presented to a subject as part of a DNA vaccine alone, or in combination with another Hantavirus DNA segment, whether the combination is on the same construct or on a different construct.

It is another object of the present invention to provide a method for eliciting in a subject an immune response against hantavirus, the method comprising administering to a subject a DNA fragment comprising a genome segment of hantavirus. More specifically, the present invention relates to a method for eliciting an immune response against SEOV hantavirus by providing the M or S genome segment of SEOV, a method for eliciting an immune response against HTNV hantavirus by providing the M genome segment of HTNV, a method for eliciting an immune response against ANDV hantavirus by providing the M genome segment of ANDV. Cross protection against other hantaviruses such as Hantaan virus and Dobrava or Sin Nombre and Black Creek Canal are also an object of this invention.

It is also an object of the present invention to provide a DNA vaccine which elicits an immune response against both HFRS and HFS hantavirus and protects against all the hantaviruses causing severe disease by providing to a subject a DNA vaccine comprising a Hantaan M gene DNA vaccine in combination with an Andes M gene DNA vaccine such that each M gene is expressed in the subject. The Hantaan M gene or the Andes M gene may be administered separately, i.e. on seperate vectors, or may be combined on the same vector as is described in one aspect of this invention. In addition, other M gene segments from other hantaviruses, e.g. Puumula, may be combined with the Hantaan DNA vaccine and the Andes DNA vaccine in order to produce a multivalent vaccine which can provide additional protection against hantavirus infection.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune reponses in the vaccinated individual.

The DNA vaccine according to the present invention is inherently safe, is not painful to administer, and should not result in adverse side effects to the vaccinated individual. In addition, the invention does not require growth or use of hantavirus, which may be spread by aerosol transmission.

It is further an object of the present invention to provide a composition of primate polyclonal serum containing neutralizing antibodies directed against at least one, preferably two or more, hantavirus M segments, e.g. Andes virus and/or against Hantaan virus.

It is another object of the invention to provide for antibodies that are functionally equivalent to the antibodies listed above. These functionally equivalent antibodies substantially share at least one major functional property with an antibody listed above and herein described comprising: immunoreactivity in vitro, protection against hantavirus challenge when administered prophylactically or therapeutically, competition for same binding site on G1 and/or G2. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining an Fab portion and a Fc region from different species.

It is yet another object of the present invention to treat or prevent hantavirus infection by administering a therapeutically or prophylactically effective amount of serum of the present invention or a mixture of antibodies of the present invention to a subject in need of such treatment.

It is another object of the present invention to provide passive vaccines for treating or preventing hantavirus infections comprising a therapeutically or prophylactically effective amount of the antibodies of the present invention which protect against hantavirus disease in combination with a pharmaceutically acceptable carrier or excipient.

It is yet another object of the present invention to provide a method for diagnosis of hantavirus infection by assaying for the presence of hantavirus in a sample using the antibodies of the present invention.

It is still another object of the present invention to provide novel immunoprobes and test kits for detection of hantavirus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to hantavirus to form an immunological complex and detecting the formation of the immunological complex such that presence or absence of the immunological complex correlates with presence or absence of hantavirus.

BRIEF DESCRIPTION OF THE DRAWINGS

These and other features, aspects, and advantages of the present invention will become better understood with reference to the following description, appended claims, and accompanying drawings where:

FIG. 1. SEOV naked DNA expression constructs. The SEOV M or S genome segment was amplified by RT-PCR and cloned into NotI and BamHI sites of pWRG7077 (PowderJect Vaccines, Inc., Madison, Wis., described in Schmaljohn et al., 1997, supra). Characteristics of pWRG7077 are similar to those of pWRG1602 described previously (Dimmock, N. J., 1995, *Med. Virol.* 5: 165) and include a human cytomegalovirus early promoter (CMV IE promoter) and intron A, a bovine growth hormone transcription terminator and polyadenylation signal (BGH pA), and a kanamycin resistance gene. CMV IE promoter: cytomegalovirus immediate early promoter and intron A, BGH pA: Bovine growth hormone polyadenylation signal, KAN: kanamycin antibiotic resistance gene.

FIGS. 2A and 2B. Transient expression from pWRG/SEO-M (SEQ ID NO:3) and pWRG/SEO-S (SEQ ID NO:4). A) IFAT were performed on COS cell monolayers transfected with the SEOV M or S constructs. pWRG/7077-transfected monolayers served as negative controls. Anti-SEOV polyclonal rabbit antisera was used as the primary antibody. B) COS cells were transfected with the indicated plasmid and radiolabeled expression products were immunoprecipitated with anti-SEOV polyclonal rabbit serum. Molecular size markers (MW) in kDa are shown on the left, and the position of the SEOV G1, G2, and N proteins are shown on the right.

Pre and postchallenge serum samples were evaluated by anti-N ELISA to detect antibody to nucleocapsid, and by a Hantaan plaque reduction neutralization test (PRNT) to detect Hantaan neutralizing antibodies ELISA titers represent the lowest reciprocal dilution that resulted in an O.D. value that was greater than the background O.D. plus three standard deviations. PRNT50% titers represent the lowest reciprocal dilution that resulted in a 50% reduction in plaque number in the absence of serum.

FIG. 6. Vaccination with pWRG/SEO-M cross-protects against infection with Dobrava virus. Groups of 5 hamsters were vaccinated with either pWRG/SEO-M or negative control plasmid (pWRG7077) as described in Methods. Three weeks after the final vaccination, prechallenge serum samples were obtained and the hamsters were challenged with 1,000 PFU of Dobrava virus. Twenty-eight days after challenge postchallenge serum samples were obtained. Pre and postchallenge serum samples were evaluated by anti-N ELISA to detect antibody to nucleocapsid, and by a Dobrava plaque reduction neutralization test (PRNT) to detect Dobrava neutralizing antibodies. ELISA titers represent the lowest reciprocal dilution that resulted in an O.D. value that was greater than the background O.D. plus three standard deviations. PRNT50% titers represent the lowest reciprocal dilution that resulted in a 50% reduction in plaque number in the absence of serum. The Seoul neutralizing prechallenge antibody titers (elicited by the vaccine) were also measured. The Seoul virus PRNT80% values are shown as empty circles.

FIG. 7. Vaccination with pWRG/SEO-M fails to cross-protect against infection with Puumala virus. Groups of 5 hamsters were vaccinated with either pWRG/SEO-M or negative control plasmid (pWRG7077) as described in Methods. Three weeks after the final vaccination, prechallenge serum samples were obtained and the hamsters were challenged with 1,000 PFU of Puumala virus. Twenty-eight days after challenge postchallenge serum samples were obtained. Pre and postchallenge serum samples were evaluated by anti-N ELISA to detect antibody to nucleocapsid, and by a Puumala plaque reduction neutralization test (PRNT) to detect Puumala neutralizing antibodies. ELISA titers represent the lowest reciprocal dilution that resulted in an O.D. value that was greater than the background O.D. plus three standard deviations. PRNT50% titers represent the lowest reciprocal dilution that resulted in a 50% reduction in plaque number in the absence of serum. The Seoul neutralizing prechallenge antibody titers (elicited by the vaccine) were also measured. The Seoul virus PRNT80% values are shown as empty circles.

Figure 8:
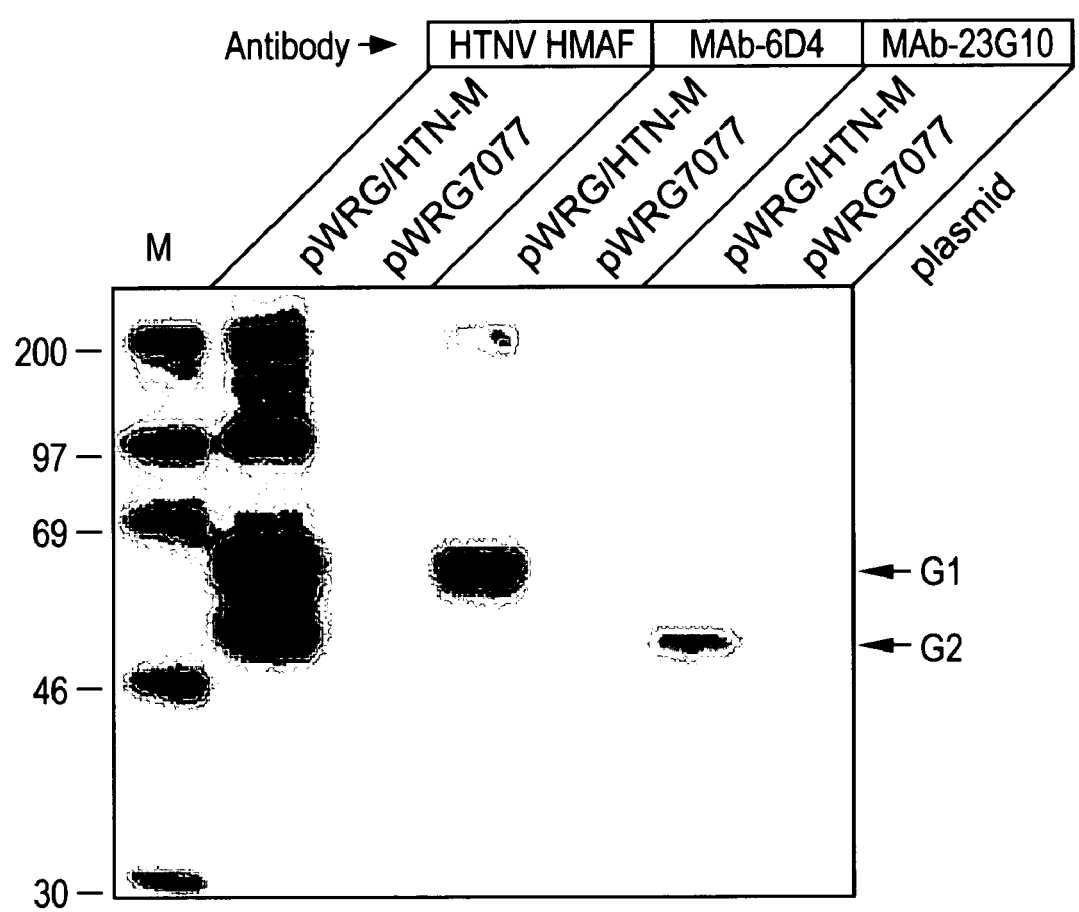

FIG. 8. Transient expression of HTNV G1 and G2. Cos cells were transfected with pWRG/HTN-M or a negative control plasmid (pWRG7077) and, after 24 hrs, radiolabeled cell lysates were prepared for analysis by RIPA. Expression products were immunoprecipitated with a polyclonal mouse hyperimmune ascitic fluid against HTNV (HTN HMAF), a G1-specific MAb (MAb 6D4), or a G2-specific MAb (Mab-23G10). Molecular sizes (M) are shown at left in kDa, and the position G1 and G2 are shown at the right.

FIGS. 9A, 9B, 9C, 9D. Efficient expression of G1 requires upstream extraneous sequence. (A) Schematic diagram of SEOV M gene DNA vaccine plasmid, pWRG/SEO-M, showing nucleotide sequence between NotI site of the vector and the SEOV G1 start codon [SEQ ID NO:5]. The NotI site is followed by 24 extraneous nucleotides arising from a previous cloning procedure [SEQ ID NO:6], which is followed by SEOV M antigenome 5' noncoding region starting at position 2. The hantavirus M genes were cloned into either the NotI-BamHI site, or the NotI-BglII site of pWRG7077. G1/G2, open reading frame encoding the G1 and G2 glycoproteins; CMV IE intron A, cytomegalovirus immediate-early promoter followed by intron A sequence; KANr, kanamycin resistance gene; BGH poly A, bovine growth hormone polyadenylation signal. (B) Alterations in the extraneous sequence affect SEOV G1 expression. COS cells were transfected with pWRG/SEO-M (SEO-M) (sequence in this column corresponds to SEQ ID NO:6), or a plasmid with the indicated alteration: extraneous sequence removed (0); extraneous sequence restored (1–24) (sequence in this column corresponds to SEQ ID NO:6); extraneous sequence reversed (24–1) (sequence in this column corresponds to SEQ ID NO:6 reserved); 3' half of extraneous sequence removed (1–12) (sequence in this column corresponds to nucleotides 1–12 of SEQ ID NO:6); 5' half of extraneous sequence removed (13–24) (sequence in this column corresponds to nucleotides 13–24 of SEQ ID NO:6); substitution of AG with CC at position 9,10 of extraneous sequence (1–24* (sequence in this column corresponds to SEQ ID NO:6 with CC to AG substitution at position 9, 10 of sequence). Immunoprecipitations were performed using polyclonal rabbit anti-SEOV antibody containing G1- and G2 specific antibodies (1), or a pool of G2-specific monoclonal antibodies (3). The sequence between the NotI site of the vector and position 2 of the SEOV M gene nontranslated region are shown. A, indicates extraneous sequence is deleted. The underlined GGATCTGC (nucleotides 1–8 of SEQ ID NO:6) is the minimal unaltered sequence associated with efficient expression of G1. (C) Efficient G1 expression is restored if nucleotides 1–8 of the extraneous sequence, GGATCTGC (nucleotides 1–8 of SEQ ID NO:6), are included between the NotI site and the SEOV M noncoding region. COS cells were transfected with pWRG/SEO-M (SEO-M), or a plasmid with the extraneous sequence removed (0); extraneous sequence restored (1–24) (SEQ ID NO:6); or a shortened version of the extraneous sequence (1–8) (nucleotides 1–8 of SEQ ID NO:6). Immunoprecipitations were performed using polyclonal rabbit anti-SEOV antibody containing G1- and G2 specific antibodies (1), a G1-specific MAb pool (2), or a G2-specific MAb-11E10 (3) (D) Deletion of the extraneous sequence affects HTNV G1 expression. COS cells were transfected with the HTNV M gene DNA vaccine plasmid, pWRG/HTN-M(x)(HTN-M) (sequence in this column corresponds to SEQ ID NO:6), or a plasmid with the indicated alteration: extraneous sequence removed (0); extraneous sequence restored (1–24) (sequence in this column corresponds to SEQ ID NO:6). Immunoprecipitations were performed using anti-HTNV mouse hyperimmune ascitic fluid containing G1- and G2-specific antibodies (1), G1-specific MAb pool (2), or a G2-specific MAb-11E10 (3). Molecular sizes (M) are shown at the left in kDa, and the position of G1 and G2 are shown at the right.

FIG. 10: Schematic of pWRG/HTNV-M(x) plasmid expressing G1 and G2. pWRG/HTN-M(x) employs the hCMV immediate early promoter and 5' noncoding sequences from exons 1 and 2 with the native intervening Intron A. The Hantaan virus M gene open reading frame (ORF) is preceded by the Hantaan virus M untranslated region (UTR) and followed by sequence from the Hantaan M gene 3'-UTR. Extraneous sequence that we have found is required for efficient G1 expression is between the Intron A and Hantaan virus 5' UTR. Transcription termination is facilitated by a bovine growth hormone polyadenylation site (BGH polyA). The plasmid backbone is pUC19 and a kanamycin resistance gene (KanR) confers antibiotic resistance.

Figure 11:
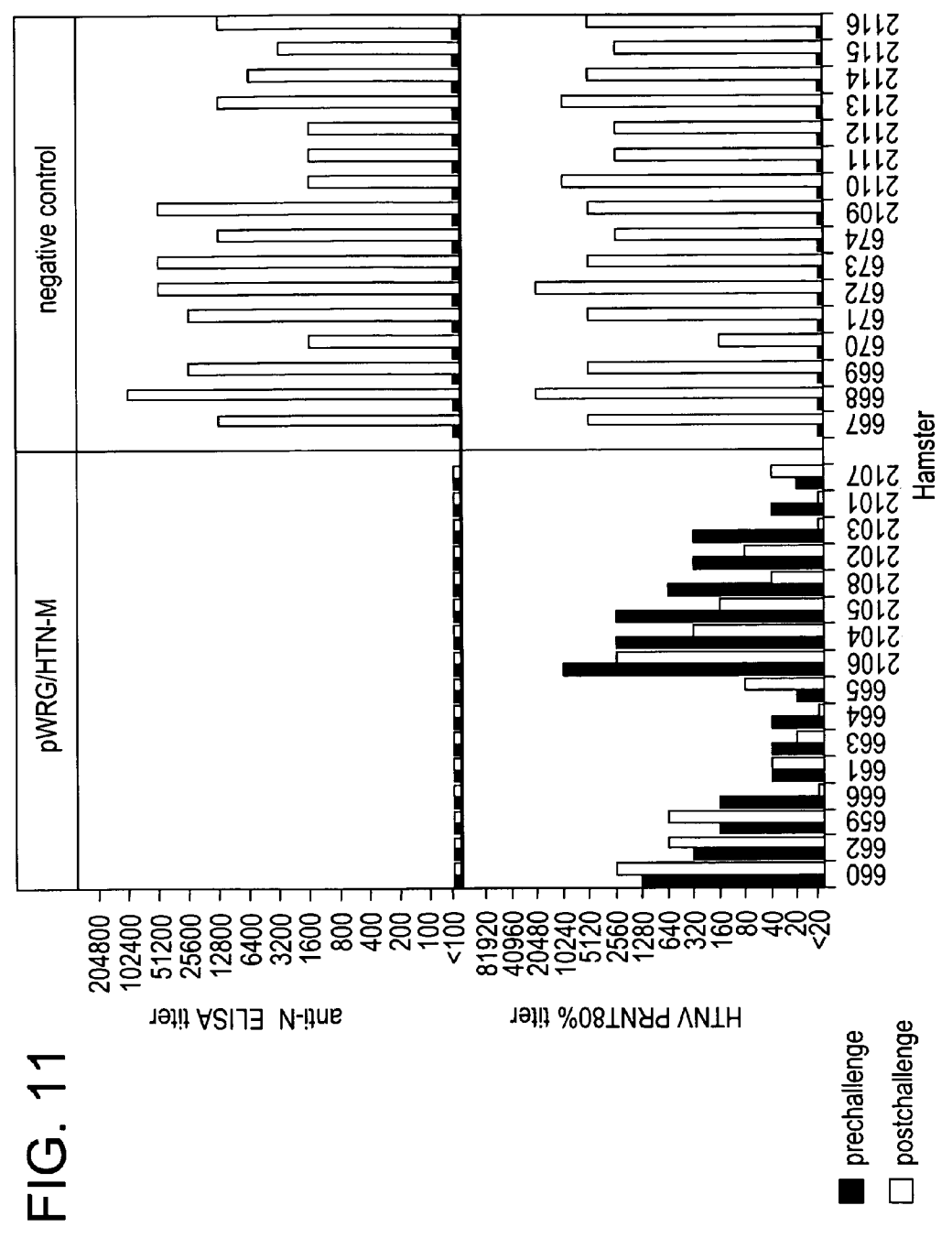

FIG. 11: DNA vaccination with plasmid expressing HTNV G1 and G2 protects against HTNV infection. The results of two independent experiments are combined in this figure. In the first experiment, one group of hamsters (659–666) was vaccinated with pWRG/HTN-M, and a second negative control group (667–674) was vaccinated with the vector plasmid, pWRG7077. In the second experiment one group of hamsters (2101–2108) was vaccinated with pWRG/HTN-M(x) and a second negative control group (2109–2116) remained unvaccinated. Three weeks after the final vaccination, prechallenge serum samples were obtained and the hamsters were challenged with HTNV. Postchallenge serum samples were obtained 28 days after challenge. The pre- and postchallenge serum samples were tested for N-specific antibodies by anti-N ELISA, and neutralizing antibodies by PRNT. The pre- and postchallenge, end-point antibody titer for each hamster is shown. For each experiment, the prechallenge homotypic $PRNT_{80\%}$ titers were sorted from highest to lowest, left to right.

FIGS. 12A, 12B, 12C, 12D, and 12E: Cross-protection. Hamsters were vaccinated with the indicated plasmid (pWRG/SEO-M, pWRG/HTN-M(x) containing the extraneous sequence, or a negative control), and then challenged with the indicated virus. The negative control hamsters in panels A, B, and C were vaccinated with a pWRG7077-based plasmid; and the negative control hamsters in panels D and E remained unvaccinated. Pre- and postchallenge serum samples were tested for anti-N antibodies by anti-N ELISA, and neutralizing antibodies by PRNT. $PRNT_{80\%}$ titers for homotypic virus, and $PRNT_{50\%}$ titers for heterotypic virus, were determined. The prechallenge and postchallenge end-point antibody titers for each hamster are shown. Prechallenge homotypic $PRNT_{80\%}$ titers (sorted from highest to lowest, left to right) are shown as lines with symbols. The identification code for each hamster is shown on the x-axis. The HTNV PRNT, and anti-N ELISA data for hamsters 943, 944, 945, and 948 was published previously (Kamrud et al., 1999, Virology, 263, 209–219).

Figure 13:
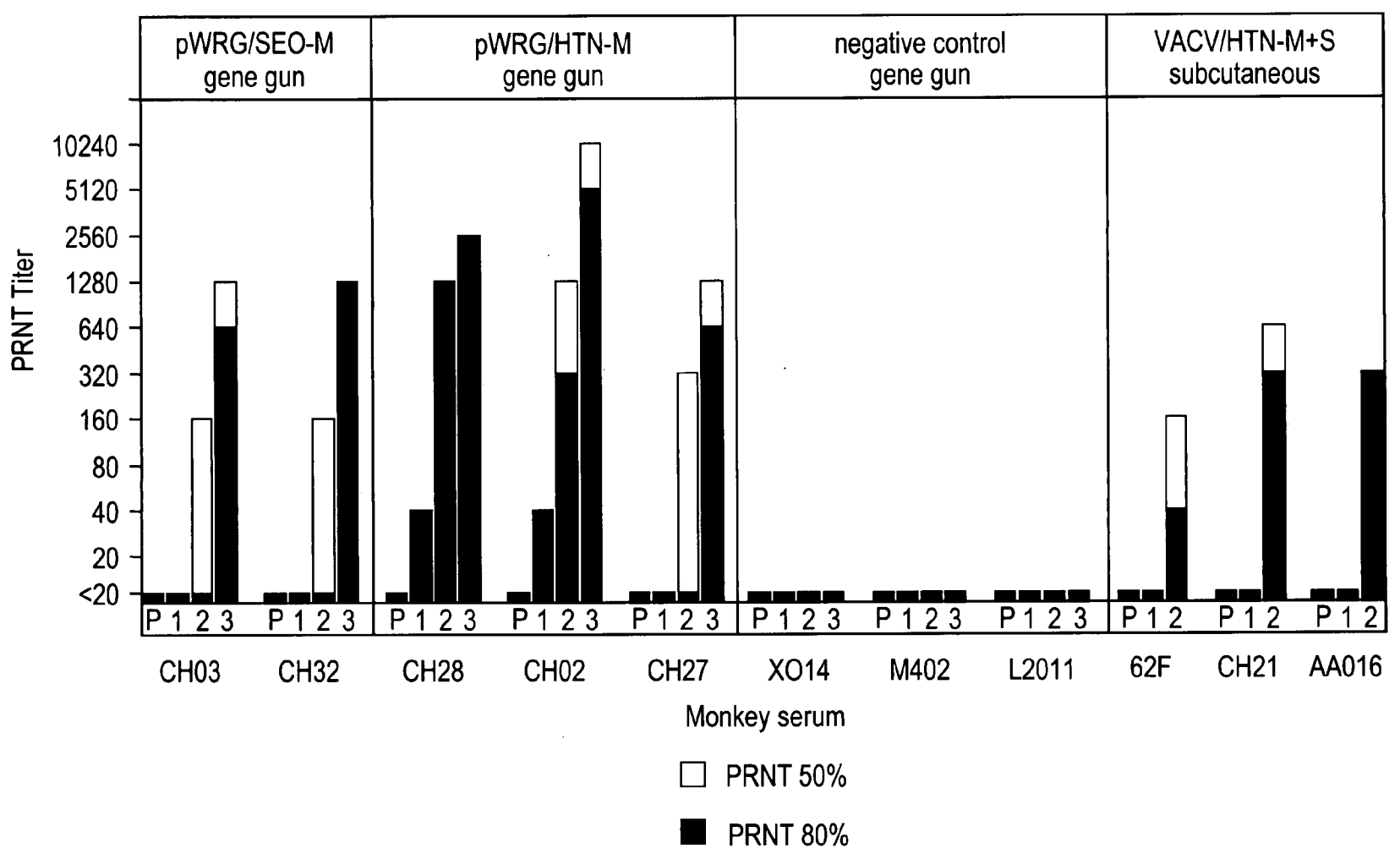

FIG. 13: DNA vaccination with plasmid expressing SEOV or HTNV G1 and G2 elicits high-titer neutralizing antibody responses in rhesus monkeys. Rhesus monkeys were vaccinated with either pWRG/SEO-M(x), pWRG/HTN-M(x), or rVV/HTN-M+S by the indicated route as described in Methods. Serum samples were obtained before vaccination (P), and then 3 weeks after the first (1), second (2) and third vaccination (3). Serum was also collected 2 months (a) 4 months (b), and 6 months (c) after the final vaccination. PRNT titer represents the reciprocal serum dilution that neutralized virus plaque number 80% or 50%. The identification code for each monkey is shown below its respective plot.

Figure 14:
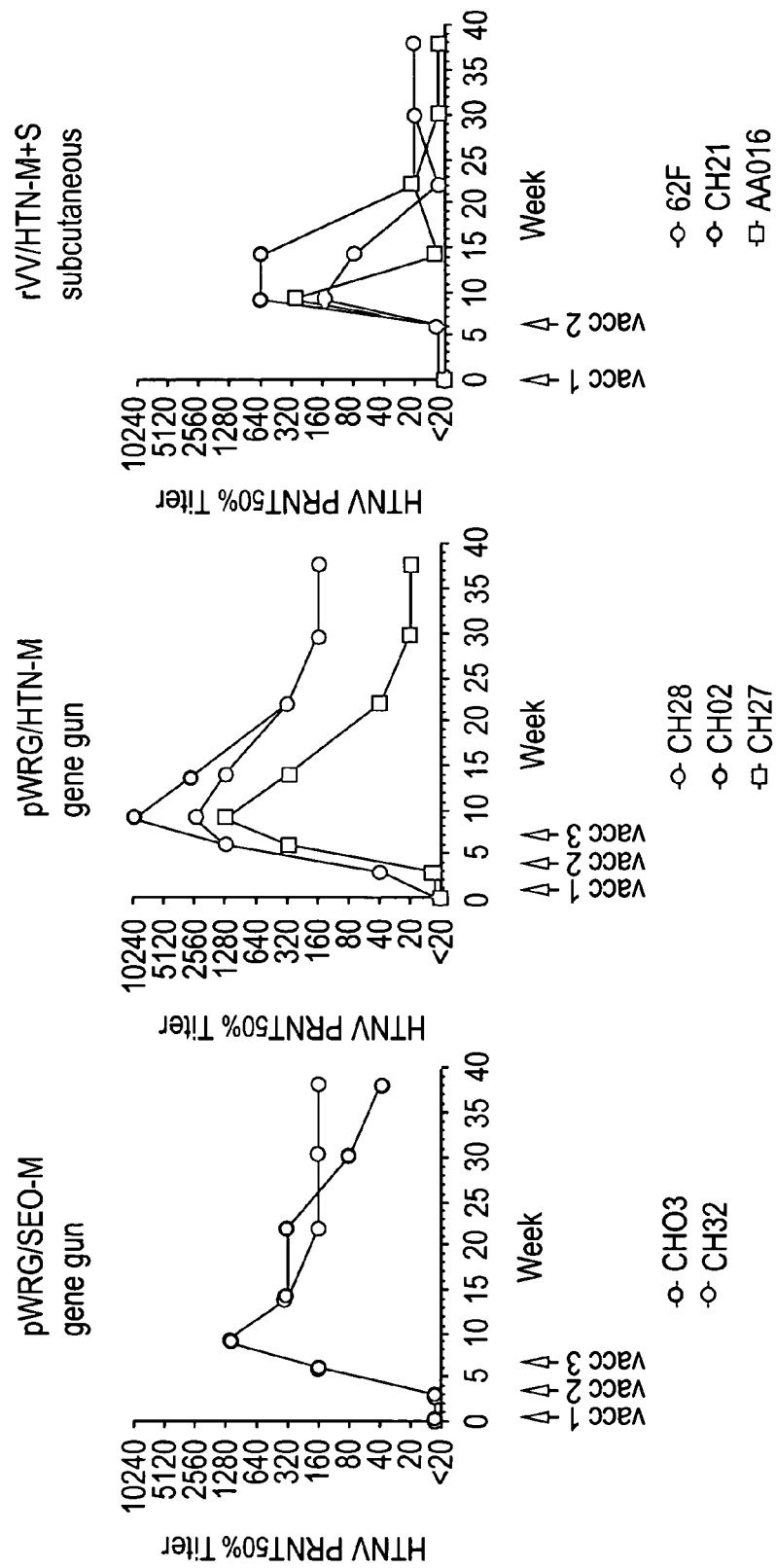

FIG. 14: Duration of Neutralizing antibody response in monkeys. Neutralizing antibodies elicited by DNA vaccination are still detected in rhesus monkeys 8 months after the final vaccination. Rhesus monkeys vaccinated with the indicated vaccine were bled 3 weeks after each vaccination and then at 2, 4, 6, and 8 months after the final vaccination (weeks 14, 22, 30, and 38, respectively). The homologous neutralizing antibody response for the indicated week after the first vaccination (week 0) was evaluated by PRNT. Each line represents an individual monkey. The week 9 data are also presented in FIG. 13.

Figure 15:
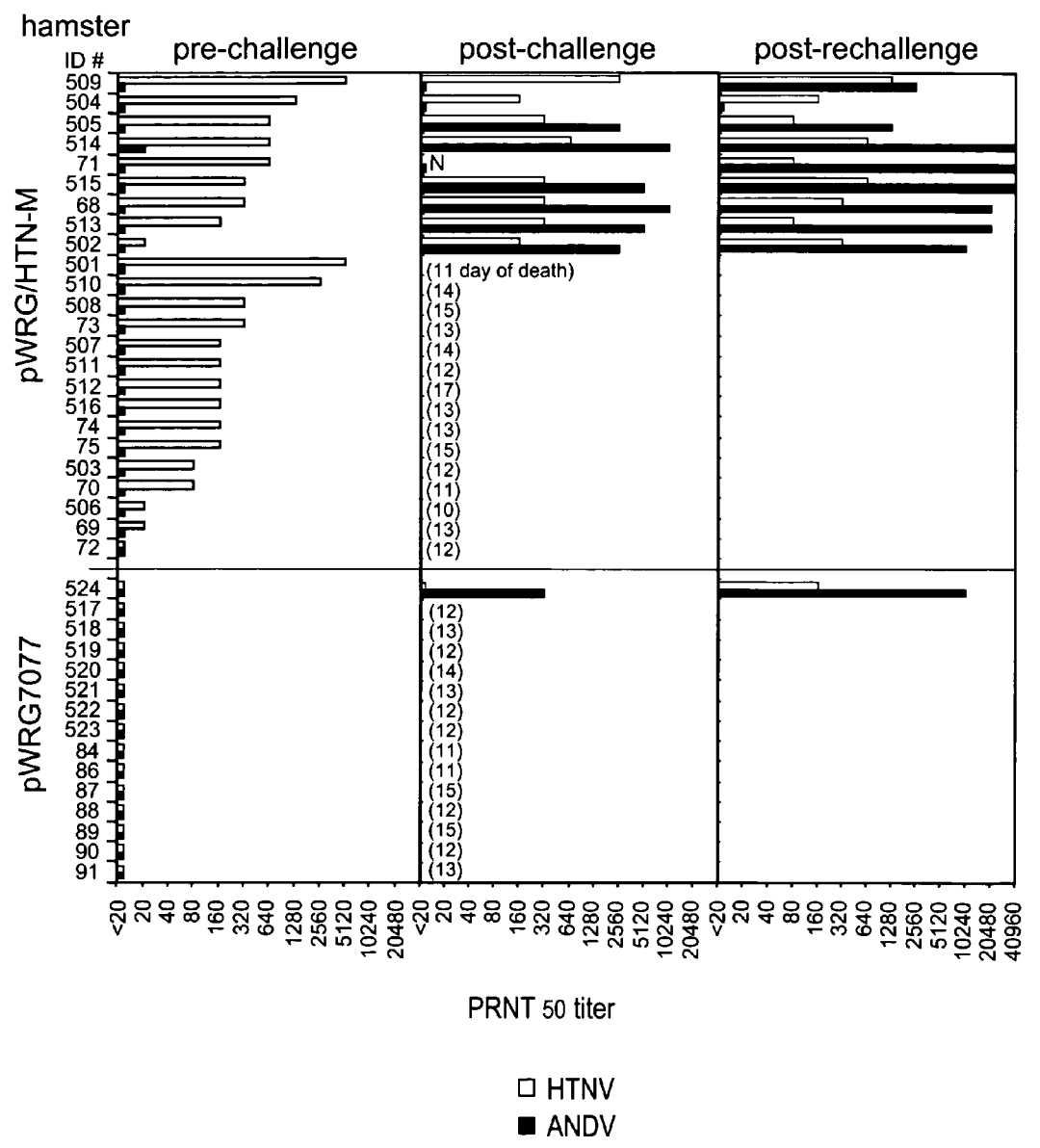

FIG. 15: Evaluation of HFRS DNA vaccine in hamster/ANDV lethal disease model. Hamsters were vaccinated with pWRG/HTN-M(x) or negative control plasmid pWRG7077 and then challenged with ANDV. For animals that succumbed, the day-of-death is shown in parentheses. Animals that survived the first challenge were rechallenged with ANDV. Serum drawn on the day of challenge (prechallenge), 4–6 weeks after challenge (postchallenge), and 28–48 days after a second challenge (post-rechallenge) was tested for HTNV- and ANDV-specific NAbs by PRNT. Bars represent PRNT titers. Hamster identification numbers (ID#) 68–91 and 501–523 represent two independent experiments; N, not done.

FIG. 16: Schematic of pWRG/AND-M plasmid. pWRG/AND-M employs the hCMV immediate early promoter and 5' noncoding sequences from exons 1 and 2 with the native intervening Intron A. The Andes virus M gene open reading frame (ORF) is preceded by the Andes virus M untranslated region (UTR) and followed by sequence from the Andes M gene 3'-UTR. Extraneous sequence that we have found is required for efficient G1 expression is between the Intron A and Andes virus 5'-UTR. Transcription termination is facilitated by a bovine growth hormone polyadenylation site (BGH polyA). The plasmid backbone is pUC19 and a kanamycin resistance gene (KanR) confers antibiotic resistance.

Figures 17A, 17B, 17C:
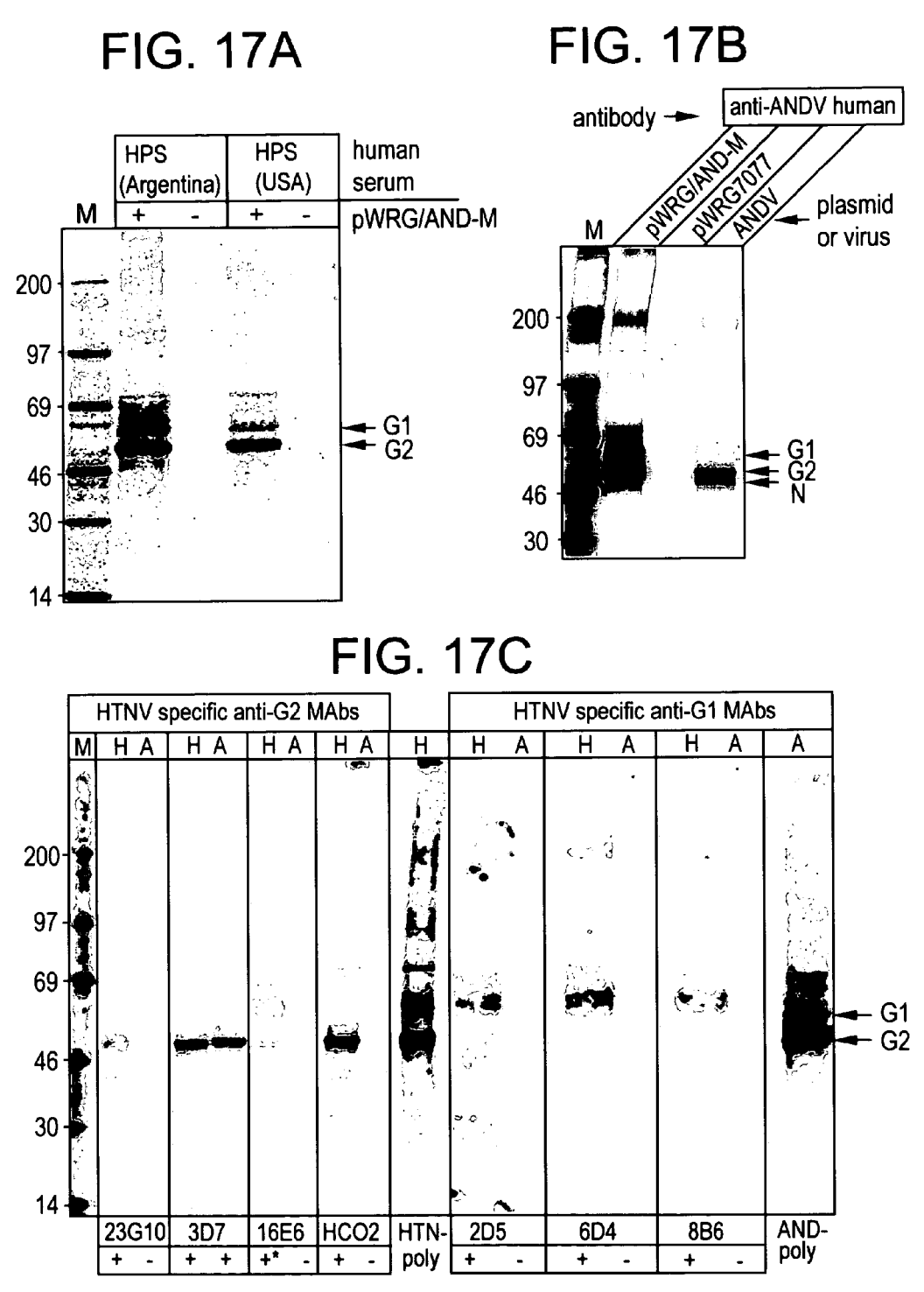

FIGS. 17A, 17B, and 17C: Expression from pWRG/AND-M. A) HPS convalescent serum from Argentina or the U.S. were used to immunoprecipitate radio-labeled proteins from COS cells transfected with pWRG/AND-M (+), or empty vector plasmid pWRG7077 (−). B) HPS convalescent serum from Argentina (anti-ANDV human) was used to immunoprecipitate proteins from COS cells transfected with pWRG/AND-M, pWRG7077, or Vero E6 cells infected with ANDV. C) The indicated HTNV specific MAbs, HTNV-specific mouse hyperimmune ascitic fluid (HTN-poly), or HPS convalescent serum form Argentina (AND-poly) were used to immunoprecipitate proteins from COS cells transfected with pWRG/HTN-M(x) (H) or pWRG/AND-M (A). + indicates G1 or G2 were immunoprecipitated, − indicates no protein was immunoprecipitated, and * indicates both G1 and G2 were immunoprecipitated. Molecular size marker (M) sizes in kDa are shown at the left and the position of G1, G2, and N are shown at the right.

Figure 18A:
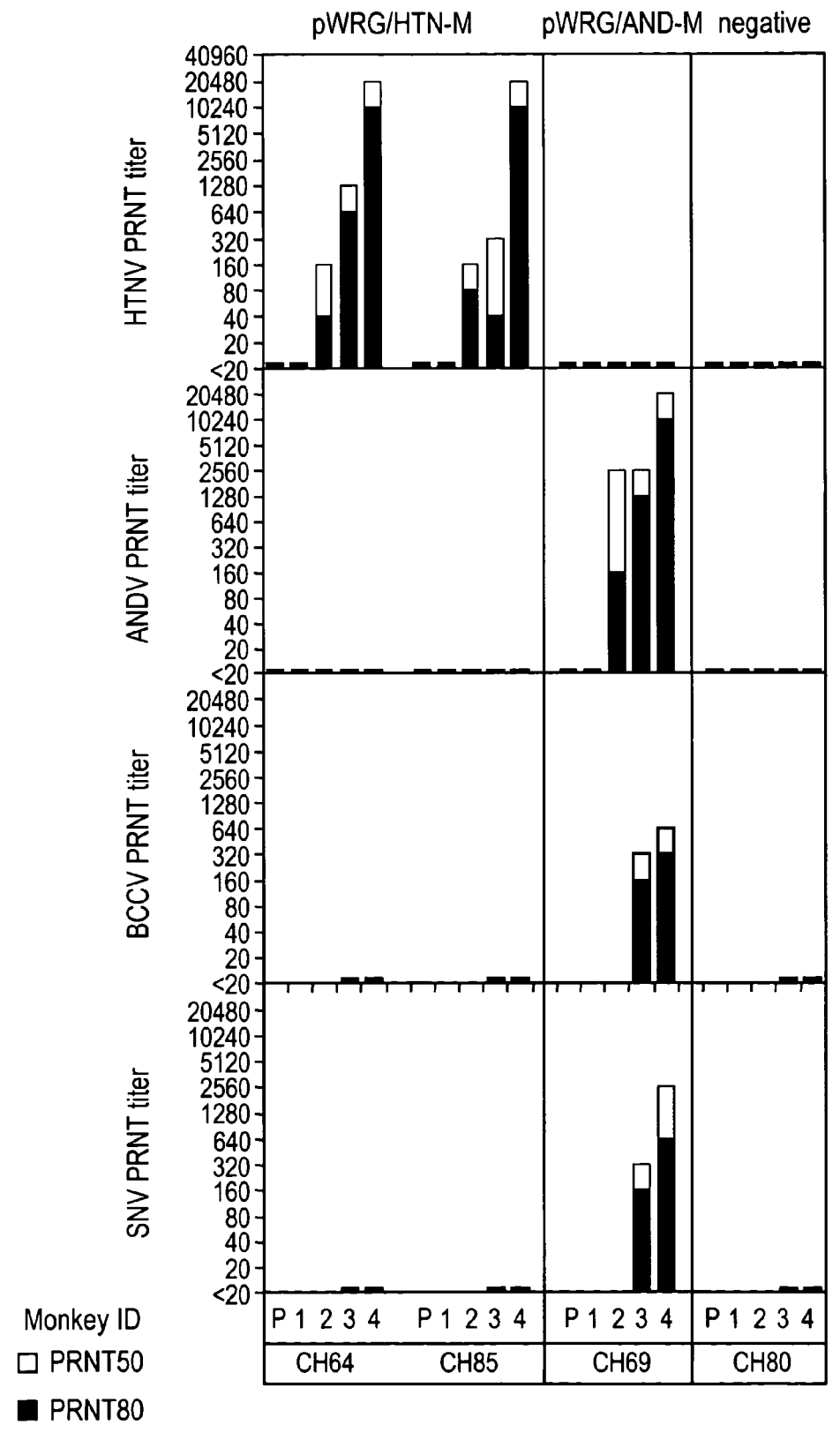
Figure 18B:
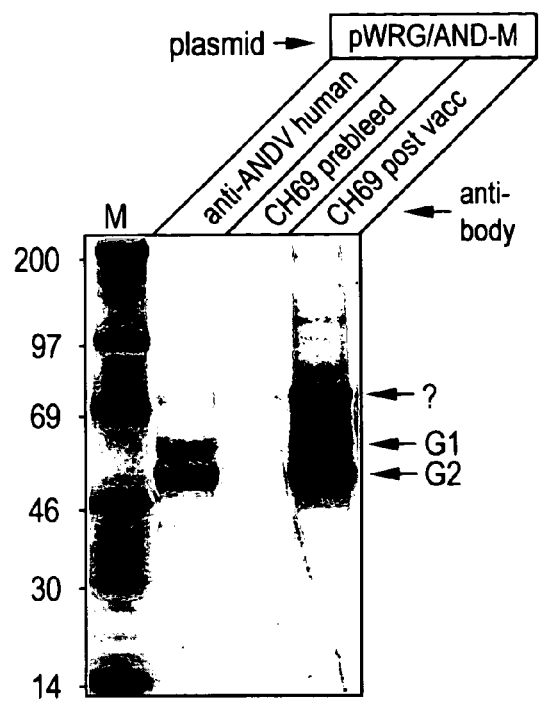
Figure 18C:
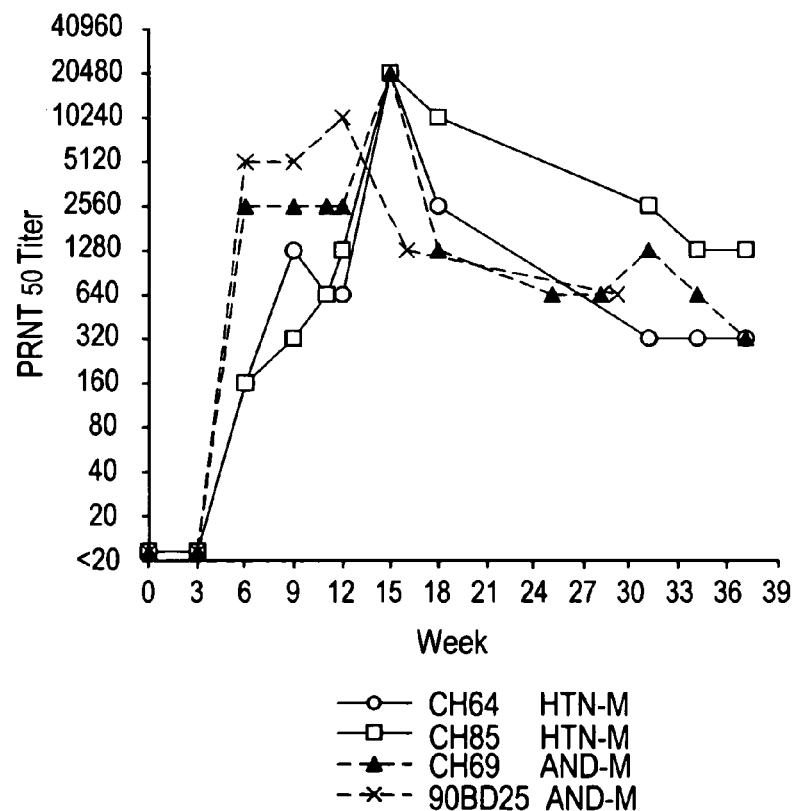

FIGS. 18A, 18B, and 18C: Immunogenicity of hantavirus DNA vaccines in nonhuman primates. A) Rhesus macaques were vaccinated with pWRG/HTN-M(x), pWRG/AND-M, or a negative control plasmid. Serum was collected before the first vaccination (P), and 3 weeks after the first, second, third, and fourth vaccination, 1, 2, 3, 4, respectively. HTNV-, ANDV-, BCCV-, and SNV-specific PRNT were performed and the endpoint 50% and 80% titers were determined. B) Serum from monkey CH69 collected before (prebleed) and after (postvaccination) four vaccinations with pWRG/AND-M was tested by RIPA for G1- and G2-specific antibodies using radio-labeled lysates from cells transfected with pWRG/AND-M. Human HPS-patient convalescent serum (anti-ANDV human) was used as a positive control for anti-ANDV antibodies. Molecular size marker (M) sizes in kDa are shown at the left and the position of G1, G2, and a ~70 kDa protein (identity unknown) are shown at the right. C) The NAb responses in monkeys vaccinated with either pWRG/HTN-M(x) or pWRG/AND-M were determined after each vaccination and then at the indicated weeks after the first vaccination (week 0). CH64, CH85, and CH69 were vaccinated on week 0, 3, 6, and 12; and monkey 90BD25 was vaccinated on week 0, 3, 6, and 9. NAb titers to HTNV (solid line) or ANDV (dashed line) were determined by PRNT.

Figure 19:
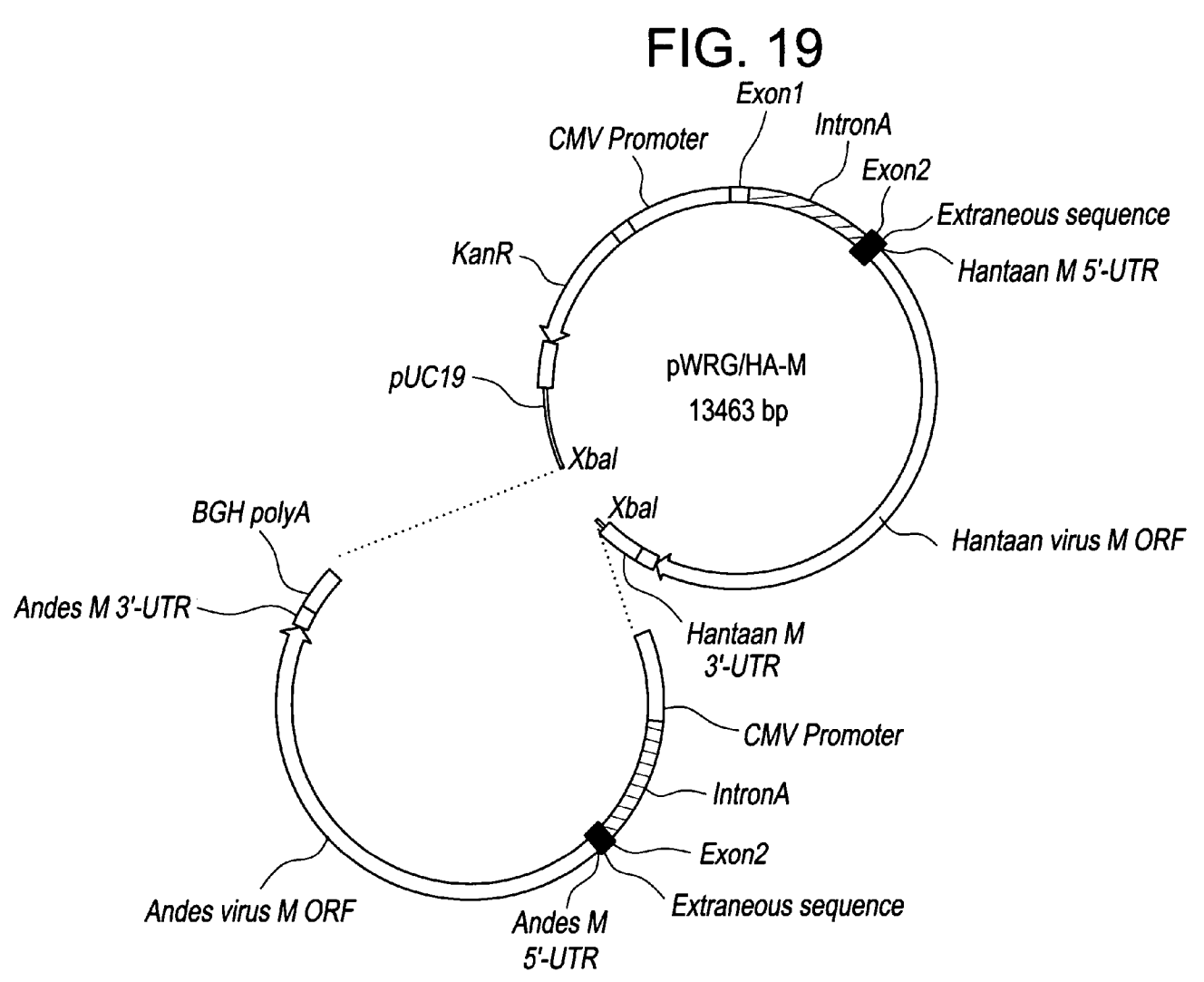

FIG. 19: Schematic of pWRG/HA-M plasmid. pWRG/HA-M was constructed by PCR amplifying a region from pWRG/AND-M and inserting it into the XbaI site of pWRG/HTN-M(x). The region amplified (using primers that created XbaI sites) included the CMV promoter, Intron A, Exon 2, extraneous sequence, Andes M 5'-UTR, Andes virus M ORF, Andes 3'-UTR and BGH poly A. See previous figures for other abbreviations

DETAILED DESCRIPTION

In this application is described a composition and method for the vaccination of individuals against hantavirus. The method comprises delivery of a DNA encoding a hantavirus antigen to cells of an individual such that the antigen is expressed in the cell and an immune response is induced in the individual.

DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

In order to achieve the immune response sought, a DNA vaccine construct capable of causing transfected cells of the vaccinated individual to express one or more major viral antigenic determinant is necessary. This can be done by identifying regions of the viral genome which code for viral glycoproteins or capsid components, and joining such coding sequences to promoters capable of expressing the sequences in cells of the vaccinee. Alternatively, the viral genome itself, or parts of the genome, can be used.

In one embodiment, the present invention relates to a DNA or cDNA segment which encodes an antigen from a hantavirus. By hantavirus is meant any of the Hemmorhagic fever with renal syndrome (HFRS) hantavirus such as Hantaan virus (HTNV), Dobrava-Belgrade virus (DOBV), Puumala virus (PUUV), and Seoul virus (SEOV), as well as hantavirus pulmonary syndrome (HPS) hantaviruses such as Sin Nombre virus (SNV), Black Creek Canal virus (BCCV), Bayou virus (BAYV), New York virus (NYV), Andes virus (ANDV), Laguna Negra virus (LNV), and any other hantavirus known to cause disease in humans.

More specifically, a hantavirus genome M segment encoding two envelope glycoproteins (G1 and G2) (SEQ ID NO:1), and a hantavirus genome S segment encoding nucleocapsid protein (SEQ ID NO:2) were deduced from the SEOV, strain SR-11 (Kitamura, T. et al. 1983, *Jpn. J. Med. Sci. Biol.* 36, 17–25) viral genome (Arikawa, J. et al. 1990, *Virology* 176, 114–125). The M segment (specified in SEQ ID NO:1), deposited in GeneBank accession no. M34882, corresponds to Seoul (SR-11) M gene from nucleotide 2 to 3602. The S segment (SEQ ID NO:2), having Genebank accession no. M34881, corresponds to Seoul (SR-11) S gene from nucleotide 2 to 1699.

The Hantaan hantavirus (HTNV) M segment encoding G1/G2, published Hantaan M sequence accession number M14627, corresponds to Hantaan (strain 76–118) nucleotides 2 to 3565. The Andes M segment encoding G1/G2, deposited in GeneBank accession number AF291703, corresponds to Andes strain Chile-9717869 extending from 2 to 3671.

DNA or polynucleotide sequences to which the invention also relates include fragments of the M or S gene segment from other Hantaviruses containing protective epitopes or antigenic determinants. Such epitopes, which may be conformational, may include sequences from G1 and/or G2 since monoclonal antibodies to both G1 and G2 have been shown to neutralize virus and protect rodents in passive protection experiments. Additionally, the amino terminus of N is highly immunogenic and others have shown that other methods of vaccination with the amino terminal region can confer protection (Lundvist, 1996, supra; Ulrich, 1998, supra).

The derived sequence is not necessarily physically derived from the nucleotide sequence itself, but may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction (PCR) assays for the detection of Hantavirus.

RT-PCR cloning of the M and S genome segments of SEOV, strain SR-11, was described previously (Arikawa et al., 1990, Virology 176, 114–125). A DNA fragment containing Seoul (SR-11) M gene from nucleotide 2 to 3602 was excised from YMIS/SR 11-M (Arikawa, 1990, supra) using Bgl II and Bam HI. This fragment was ligated into the Bam HI site of pWRG7077 resulting in pWRG/SEO-M (SEQ ID NO:3). pWRG/SEO-M contains additional nucleotides derived from cloning vector baculovirus transfer vector YMIS.

A DNA fragment containing Seoul (SR-11) S gene from nucleotide 2 to 1699 was excised from pBSKS+/SR11-S (Arikawa, 1990, supra) using EcoRI. This fragment was subjected to Klenow to blunt the restriction sites and then ligated into Klenow-blunted Not I site of pWRG7077 (provided by Powderject, Inc., Madison, Wis.) resulting in pWRG/SEO-S (SEQ ID NO:4). pWRG/SEO-S contains additional nucleotides derived from cloning vector pBSKS+.

Figure 9A:
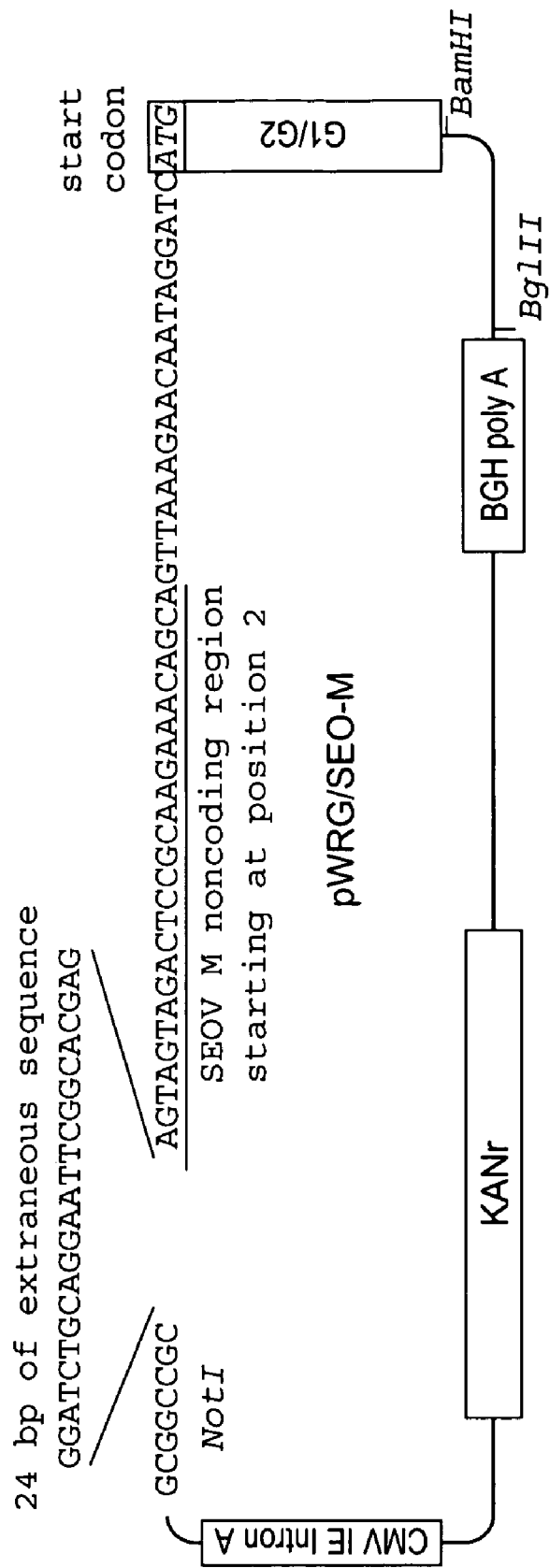
Figure 9B:
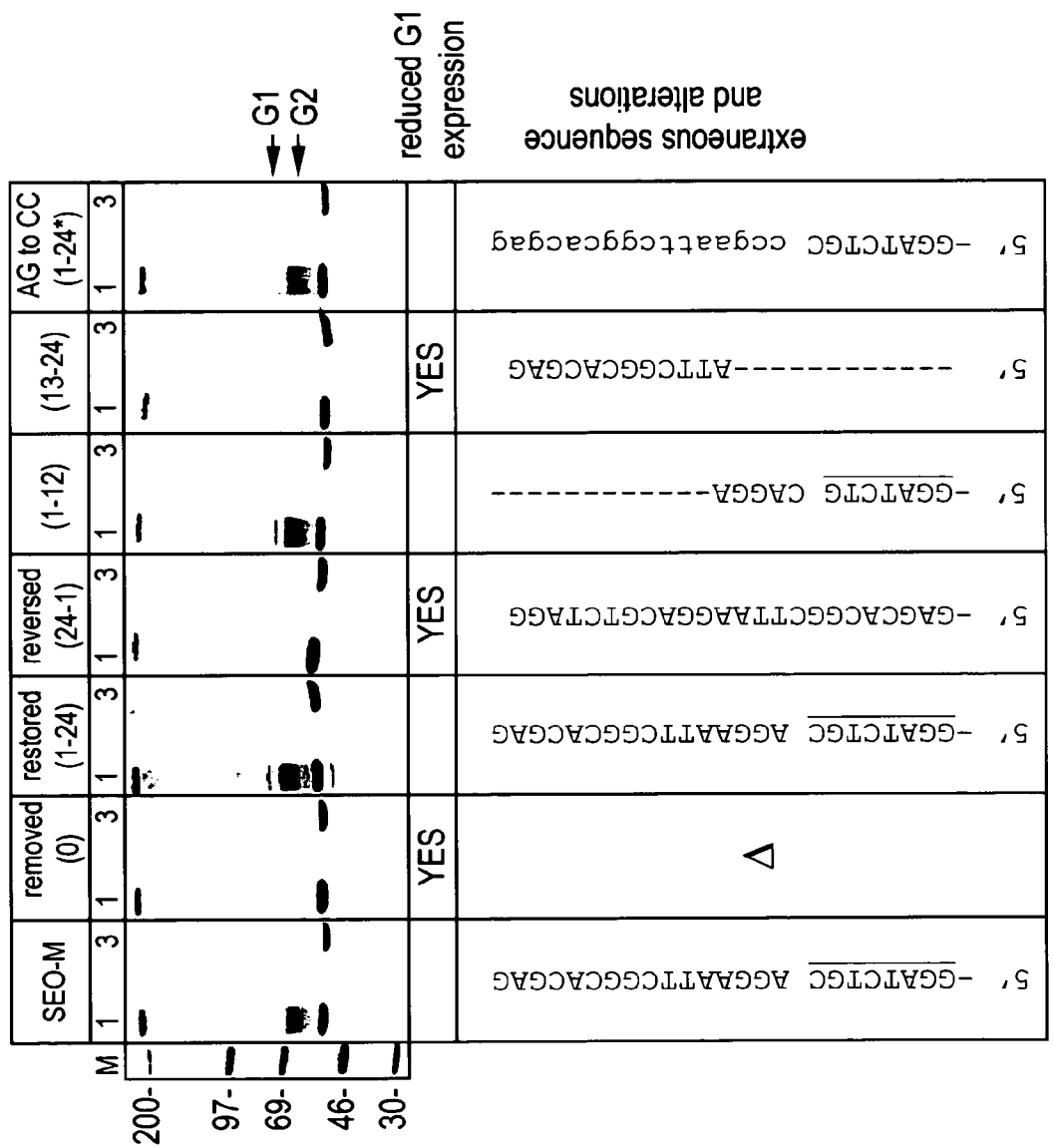
Figure 9D:
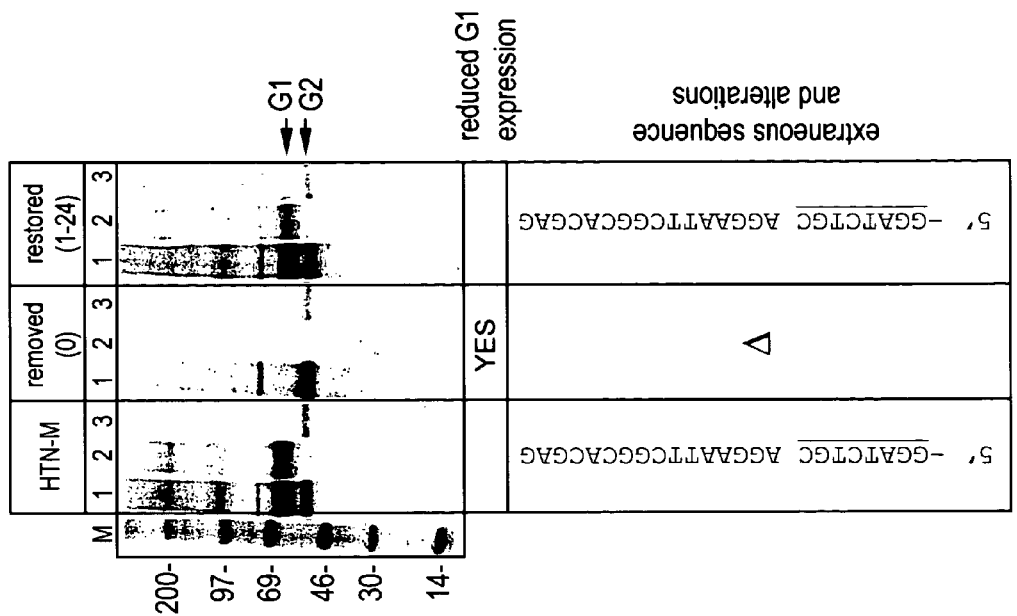
Figure 9C:
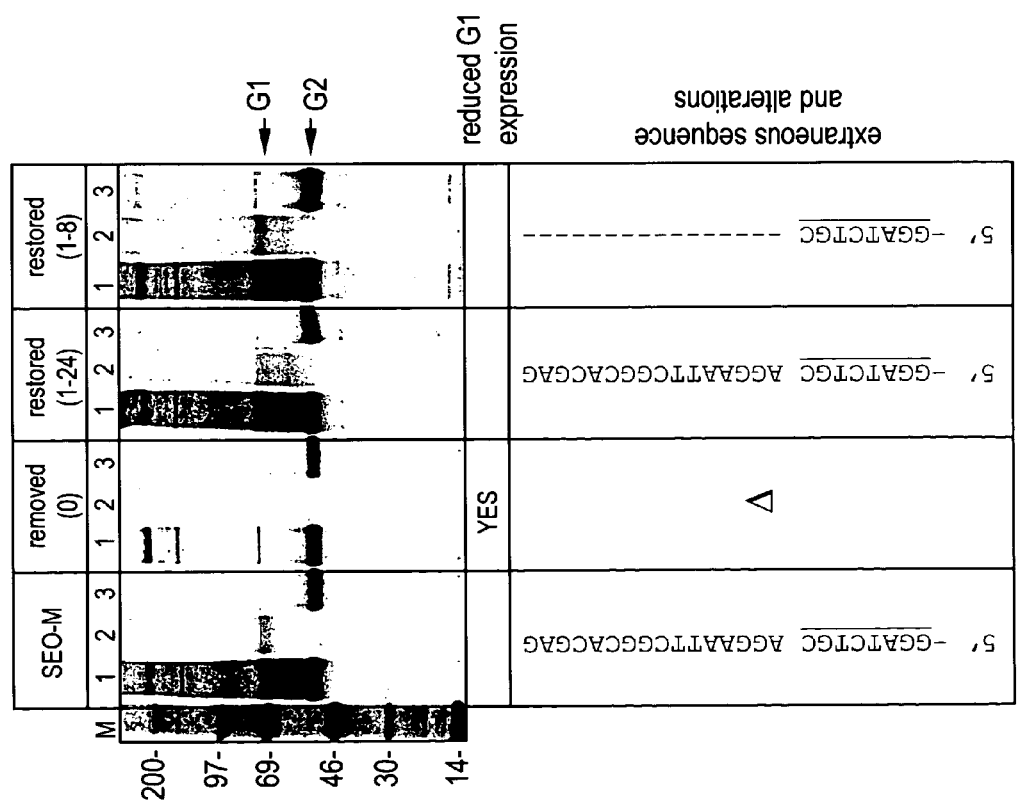

The HTNV M DNA vaccine plasmid, pWRG/HTN-M(x) (SEQ ID NO:7), was constructed essentially as follows. First, DNA encoding the HTNV G1/G2 was cut from pTZ19RHTNMm (Schmaljohn et al., 1989, In: Genetics and pathogenicity of negative strand viruses, D. Kolokofsky and B. Mahy, Eds., pp. 58–66. Elsevier Press, Amsterdam) as a BglII fragment and ligated into BamHI-cut pWRG7077 vector. This plasmid expressed G2 but not G1. We solved this problem after discovering that the SEOV M plasmid pWRG/SEO-M, failed to efficiently express G1 if a 24 base pair (bp) sequence of extraneous DNA (SEQ ID NO:6), found between the vector Not I cloning site and the SEOV M noncoding region (FIG. 9A), was removed. This extraneous DNA originated from procedures used during earlier cloning and subcloning of the SEOV gene. The SEOV M construct with the 24 bp sequence removed failed to express G1, but did express G2 (FIG. 9B). Expression of G2 was restored if the 24 bp sequence was engineered back into the construct in the forward but not reverse orientation (FIG. 9B). This result indicated that the nucleotide sequence, not nucleotide number, affected G1 expression. To map the sequence that allowed efficient G1 expression, we made constructs which included either nucleotides 1–12 or 13–24 of the extraneous sequence. G1 was expressed when nucleotides 1–12 but not 13–24 was present in the plasmid (FIG. 9B). We noted that nucleotides 4–10 of the DNA (TCTG-CAG) were identical to the last seven nucleotides of intron A (i.e., splice acceptor site)(Stenberg et al., 1984, J. Virol. 49, 190–199). Mutating the putative splice acceptor dinucleotide AG to CC did not influence the expression of G1, suggesting that, if this region is involved in splicing, it is not dependent on maintaining the exact sequence of the intron A splice site (FIG. 9B). We made a construct containing nucleotides 1–8 of the extraneous DNA and found this was sufficient to restore efficient expression of G1 (FIG. 9C). Thus, we determined that the sequence GGATCTGC, located between the NotI cloning site and the 5' noncoding region of the SEOV M gene, was required for efficient expression of G1 from pWRG7077-based DNA vaccines.

Based on the SEOV M findings, we postulated that including the extraneous sequence upstream of the HTNV M gene might allow us to solve our inability to express both HTNV G1 and G2 from a DNA vaccine plasmid. We constructed a plasmid that included the extraneous sequence upstream of the HTNV M gene and, in doing so, obtained a clone that expressed both G1 and G2, pWRG/HTN-M (x) (FIG. 9D and FIG. 10). When the extraneous sequence was removed, G1 was not expressed, and when it was restored, G1 was efficiently expressed (FIG. 9D). These data confirmed that the extraneous sequence was not only required for successful expression of SEOV G1, but also of HTNV G1. This sequence had no influence on expression of G2 from either SEOV or HTNV (FIG. 9). The mechanism by which the extraneous sequence affects G1 expression but not G2 expression remains unknown.

To construct the ANDV M gene-based DNA vaccine plasmid, pWRG/AND-M (SEQ ID NO:8), viral RNA was isolated from ANDV-infected Vero E6 and reverse transcribed. Forward and reverse primers based on the published SNV and PUUV sequences, respectively, were included in the reverse transcription reaction. The forward primer included a Not I restriction site (underlined) and 24 nucleotides upstream of the M gene noncoding region that we previously found were important for expressing G1 in pWRG/HTN-M as described above. cDNA was purified and used as template in a PCR reaction. The PCR product was cut with NotI and BamHI and then ligated into NotI-BglII-cut pWRG7077 vector to produce pWRG/AND-M. The ANDV M gene sequence was unknown, so we sequenced the M gene, and vector/insert junctions. The full-length M gene of ANDV, strain Chile-9717869, was RT-PCR cloned into pWRG7077 to yield pWRG/AND-M. We sequenced the entire M gene open reading frame. The sequence of our cloned M gene was almost identical to the published M gene sequence of ANDV, GeneBank accession number AF291703, which is not surprising because the viral isolates were from the same rodent specimen (Meisner et al., 2002, Virus Res. 89, 131–143). There were two adenine to guanine nucleotide changes. The change at position 1504 was silent and the change at position 1840 resulted in a threonine to alanine substitution at amino acid 597.

A construct comprising both the Hantaan M gene and the Andes M gene was prepared. The Hantaan M gene and the Andes M gene were cloned into pWRG7077 to produce pWRG/HA-M (SEQ ID NO:9, FIG. 19). Each M gene was flanked by a cytomegalovirus promoter and intron A (CMV intron A) and a bovine growth hormone poly adenylation site. The entire Hantaan virus and Andes virus M gene open reading frames as well as most of the 5' and 3' noncoding sequences are included in the construct. In addition, the 24 bp sequence positioned between each hantavirus M sequence and its respective CMV intron A sequence. As discussed above, we have found, for unknown reasons, this 24 bp sequence (or a portion thereof) is required for expression of G1 glycoprotein. When pWRG/HA-M is introduced into mammalian cells, the Hantaan virus and Andes virus M genes are expressed. The expression products consist of the Hantaan virus G1 and G2 glycoproteins and the Andes virus G1 and G2 glycoproteins.

It is understood in the art that certain changes to the nucleotide sequence employed in a genetic construct have little or no bearing on the proteins encoded by the construct, for example due to the degeneracy of the genetic code. Such changes result either from silent point mutations or point mutations that encode different amino acids that do not appreciably alter the behavior of the encoded protein. It is also understood that portions of the coding region can be eliminated without affecting the ability of the construct to achieve the desired effect, namely induction of a protective immune response against hantavirus. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the M and S segments of hantavirus are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 *Molecular Cloning: A Laboratory Manual* or *DNA Cloning,* Vol. I and II (D. N. Glover, ed., 1985) for general cloning methods.

Therefore, in another embodiment, the present invention relates to a recombinant DNA molecule that includes a vector and a DNA sequence as described above. The vector can take the form of a plasmid such as pCRII (Invitrogen) or pJW4303 (Konishi, E. et al., 1992, *Virology* 188:714), or any expression vector such as viral vectors e.g. adenovirus or Venezuelan equine encephalitis virus and others known in the art. Preferably, a promoter sequence operable in the target cell is operably linked to the DNA sequence. Several such promoters are known for mammalian systems which may be joined 5', or upstream, of the coding sequence for the encoded protein to be expressed. A suitable promoter is the human cytomegalovirus immediate early promoter. A downstream transcriptional terminator, or polyadenylation sequence, such as the polyA addition sequence of the bovine growth hormone gene, may also be added 3' to the protein coding sequence.

A suitable construct for use in the method of the present invention is pWRG7077 (4326 bp)(PowderJect Vaccines, Inc., Madison, Wis.), FIG. 1. pWRG7077 includes a human cytomegalovirus (hCMV) immediate early promoter (IE) and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the hantavirus M or S DNA can be cloned. Also provided on pWRG7077 is a gene that confers bacterial host-cell resistance to kanamycin. Any of the fragments that encode hantavirus G1 and/or G2 or nucleocapsid peptides can be cloned into one of the cloning sites in pWRG7077, using methods known to the art.

In a further embodiment, the present invention relates to host cells stably transformed or transfected with the above-described recombinant DNA constructs. The host cell can be prokaryotic such as *Bacillus* or *E. coli,* or eukaryotic such a *Saccharomyces* or *Pichia,* or mammalian cells or insect cells. The vector containing the hantavirus sequence is expressed in the bacteria and the expressed product used for diagnostic procedures or as a vaccine. Please see e.g., Maniatis et al., 1985 *Molecular Cloning: A Laboratory Manual* or *DNA Cloning,* Vol. I and II (D. N. Glover, ed., 1985) for general cloning methods. The DNA sequence can be present in the vector operably linked to a highly purified IgG molecule, an adjuvant, a carrier, or an agent for aid in purification of hantavirus proteins or peptides. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the hantavirus sequences are operably linked to a promoter which can be expressed in the transfected cell.

In this application we describe the elicitation of protective immunity to hantaviruses by DNA vaccines. The DNA can be delivered by injection into the tissue of the recipient, oral or pulmonary delivery and inoculation by particle bombardment (i.e., gene gun). Any of these methods can be used to deliver DNA as long as the DNA is expressed and the desired antigen is made in the cell. Two methods are exemplified in this application, both shown to be successful in eliciting a protective immune response in the vaccinee.

To deliver DNA vaccines by particle bombardment, we chose to use the PowderJect-XR™ gene gun device described in WO 95/19799, 27 Jul. 1995. Other instruments are available and known to people in the art. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, *DNA Cell. Biol.* 12: 791; Fynan, E. F. et al., 1993, *Proc. Natl. Acad. Sci. USA* 90: 11478; Haynes, J. R. et al., 1994, *AIDS Res. Hum. Retroviruses* 10: Suppl. 2:S43; Pertmer, T. M. et al., 1995, *Vaccine* 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, *Clin. Exp. Immunol.* 107 Suppl. 1:3; Labuda, M. et al., 1996, *Virology* 219:357; Rambukkana, A. et al., 1995, *Lab. Invest.* 73:521; Stingl, G., 1993, *Recent Results Cancer Res.* 128:45).

Candidate vaccines include particles having M genome segments, including G1 and/or G2, from one or more different HFRS-associated viruses such as Seoul virus, Hantaan virus, Pumuula virus, and Dobrava virus, as well as one or more HPS-associated virus such as Sin Nombre virus, Black Creek Canal virus, Bayou virus, New York virus, Andes virus, and Laguna Negra virus, or any combination thereof. The DNA segments from different viruses can be on different particles or on the same particle, whichever results in the desired immune response. In addition, the present invention relates to a vaccine comprising one or more DNAs from different hantaviruses. Such a vaccine is referred to as a multivalent vaccine. The vaccine is designed to protect against pathologies resulting from exposure to one or several hantaviruses. The vaccine can also be combined with reagents which increase the antigenicity of the vaccine, or reduce its side effects.

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 0.5 and 30 micrograms of DNA per milligram of gold bead spheres. A preferable ratio of DNA to gold is 0.5–5.0 ug of DNA per milligram of gold. A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resuspeded in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wis., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350–400 psi). The particles are entrained in the gas stream and are delivered with sufficient force toward the target tissue to enter the cells of the tissue. Further details are available in the published apparatus application.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The term transfected is used herein to refer to cells which have incorporated the delivered foreign DNA vaccine, whichever delivery technique is used.

It is herein disclosed that when inducing cellular, humoral, and protective immune repsonses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in sub-epidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it reduces the severity of the disease symptoms. It is preferred that the immunization method be at least 20% effective in preventing death in an immunized population after challenge with hantavirus. More preferably, the vaccination method is 50% or more effective, and most preferably 70–100% effective, in preventing death in an immunized population. The vaccination method is shown herein to be 100% effective in the hamster model for hantavirus. Hamsters have been used extensively as the laboratory model of choice for assessment of protective immune responses to hantaviruses. In contrast, unimmunized animals are uniformly infected by challenge with hantavirus. Our results indicate that vaccination with SEOV M genome segment protects against infection with Seoul virus Hantaan virus (HTNV), and Dobrava virus (DBOV). Vaccination with HTNV M genome segment protects against infection Hantaan virus, Seoul virus and Dobrava virus. Vaccination with ANDV M genome segment protects against infection with ANDV, Sin Nombre Virus and Black Creek Canal virus. Vaccination with ANDV-M/HTNV-M segments protects against infection with SEOV, HTNV, DBOV, ANDV, Sin Nombre, and Black Creek virus among other hantaviruses.

Generally, the DNA vaccine administered may be in an amount of about 1–8 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine for eliciting an immune response against one or more viruses, may be given in a single dose schedule, or preferably a multiple dose schedule in which a primary course of vaccination may be with 1–8 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In another embodiment, the present invention provides reagents useful for carrying out the present process. Such reagents comprise a DNA fragment containing M or S or both gene segments from one or more hantavirus, and a small, inert, dense particle. The DNA fragment, and dense particle are those described above.

Preferably, the DNA is frozen or lyophilized, and the small, inert, dense particle is in dry powder. If a coating solution is used, the dry ingredients for the coating solution may be premixed and premeasured and contained in a container such as a vial or sealed envelope.

The present invention also provides kits which are useful for carrying out the present invention. The present kits comprise a first container means containing the above-described frozen or lyophilized DNA. The kit also comprises a second container means which contains the coating solution or the premixed, premeasured dry components of the coating solution. The kit also comprises a third container means which contains the small, inert, dense particles in dry powder form or suspended in 100% ethanol. These container means can be made of glass, plastic or foil and can be a vial, bottle, pouch, tube, bag, etc. The kit may also contain written information, such as procedures for carrying out the present invention or analytical information, such as the amount of reagent (e.g. moles or mass of DNA) contained in the first container means. The written information may be on any of the first, second, and/or third container means, and/or a separate sheet included, along with the first, second, and third container means, in a fourth container means. The fourth container means may be, e.g. a box or a bag, and may contain the first, second, and third container means.

In another embodiment, the present invention relates to polyclonal antibodies from vaccinees receiving the DNA vaccines desribed above. The term "antibody" is art-recognized terminology and is intended to include molecules or active fragments of molecules that bind to known antigens. These active fragments can be derived from an antibody of the present invention by a number of techniques. For further description of general techniques for the isolation of active fragments of antibodies, see for example, Khaw, B. A. et al. *J. Nucl. Med.* 23:1011–1019 (1982). The term "antibody" also includes bispecific and chimeric antibodies.

The polyclonal antibodies described in the Examples below are characterized in that the antibody binds to the appropriate immunogen, i.e. G1 and G2, as measured by assays such as ELISA, immunoprecipitation, or immunofluorescence. Also, the antibodies must neutralize hantavirus as measured by plaque reduction neutralization test (PRNT). Any antibody retaining these characteristics is related to the present invention. The polyclonal antibody may be concentrated, irradiated, and tested for a capacity to neutralize Andes virus and Hantaan virus, among other hantaviruses of interest. Serum lots with sufficiently high neutralizing antibody titers, i.e., high enough to give a detectable response in the recipient after transfer can be pooled. The product can then be lyophilized for storage and reconstituted for use.

As described in greater detail in the examples, the present inventors have found that serum from a vaccinee immunized with a DNA vaccine comprising the M segment of a hantavirus, e.g. Hantaan or Andes, contains antibodies able to neutralize hantavirus and display in vitro and in vivo hantavirus neutralization properties. Significantly, the reactivity of the antibodies is applicable against a broad variety of different hantavirus, both HFRS hantavirus and HPS hantavirus.

Given these results, polyclonal antibodies according to the present invention are suitable both as therapeutic and prophylactic agents for treating or preventing hantavirus infection or disease in susceptible hantavirus-exposed subjects. Subjects include rodents such as mice or guinea pigs, birds or avian, and mammals, including humans.

In general, this will comprise administering a therapeutically or prophylactically effective amount of polyclonal antibodies of the present invention to a subject after possible exposure to hantavirus or to a subject exhibiting hantavirus symptoms. Any active form of the antibodies can be administered. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the antibodies does not result in clearance of the antibodies before virus can be controlled, and the induced immune response to the antibodies in the subject does not induce "serum sickness" in the subject.

Treatment of individuals having hantavirus infection may comprise the administration of a therapeutically effective amount of anti-hantavirus antibodies of the present invention. The antibodies can be provided in a kit as described below. In providing a patient with antibodies, or fragments thereof, capable of binding to hantavirus, or an antibody capable of protecting against hantavirus in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg–100 pg/kg, 100 pg/kg–500 pg/kg, 500 pg/kg–1 ng/kg, 1 ng/kg–100 ng/kg, 100 ng/kg–500 ng/kg, 500 ng/kg–1 ug/kg, 1 ug/kg–100 ug/kg, 100 ug/kg–500 ug/kg, 500 ug/kg–1 mg/kg, 1 mg/kg–50 mg/kg, 50 mg/kg–100 mg/kg, 100 mg/kg–500 mg/kg, 500 mg/kg–1 g/kg, 1 g/kg–5 g/kg, 5 g/kg–10 g/kg (body weight of recipient), although a lower or higher dosage may be administered.

The antibodies capable of protecting against hantavirus are intended to be provided to recipient subjects in an amount sufficient to effect a reduction in the hantavirus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention still further pertains to a method for detecting hantavirus in a sample suspected of containing hantavirus. The method includes contacting the sample with polyclonal antibodies of the present invention which bind hantavirus antigens, allowing the antibody to bind to the hantavirus antigen(s) to form an immunological complex, detecting the formation of the immunological complex and correlating the presence or absence of the immunological complex with the presence or absence of hantavirus antigen in the sample. The sample can be biological, environmental or a food sample.

The language "detecting the formation of the immunological complex" is intended to include discovery of the presence or absence of hantavirus antigen in a sample. The presence or absence of hantavirus antigen can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555–612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a hantavirus virus vaccinee and the polyclonal antibodies of the present invention, are allowed to compete for binding of the antigen. The amount of polyclonal antibody bound is then measured, and a determination is made as to whether the serum contains anti hantavirus antigen antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting hantavirus in a biological sample. The kit includes a container holding one or more polyclonal antibodies of the present invention which binds a hantavirus antigen and instructions for using the antibody for the purpose of binding to hantavirus antigen to form an immunological complex and detecting the formation of the immunological complex such that the presence or absence of the immunological complex correlates with presence or absence of hantavirus in the sample. Examples of containers include multiwell plates which allow simultaneous detection of hantavirus in multiple samples.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following materials and method were used in the examples below

Materials and Methods

Viruses, Cells, and Medium

HTNV, strain 76–118 (Lee, et al., 1978, J. Infect. Dis. 137, 298–308), ANDV strain Chile-9717869 (Hooper et al., 2001, Virology 289, 6–14), BCCV (Rollin et al., 1995, J. Med. Virol. 46, 35–39), and SNV strain CC107 (Schmaljohn et al., 1995, Virology 206, 963–972) were propagated in Vero E6 cells (Vero C1008; ATCC CRL 1586). Transient expression experiments were performed with COS cells (COS-7; ATTC CRL1651). Both cell types were maintained in Eagle's minimal essential medium with Earle's salts (EMEM) containing 10% fetal bovine serum (FBS), 10 mM HEPES pH 7.4, and antibiotics (penicillin [100 U/ml], streptomycin [100 µg/ml], and gentamicin sulfate [50 µg/ml]) (cEMEM) at 37° C. in a 5% $CO_2$ incubator.

HTNV G2-specific monoclonal antibodies (MAbs): MAb-23G10, MAb-11E10, MAb-3D7, MAb-16E6, and MAb-HC02; and HTNV G1-specific MAbs: MAb-2D5, MAb-6D4, MAb-8B6, MAb-3D5, and MAb-10F11 were described previously (Arikawa, et al., 1989, J. Gen. Virol. 70, 615–24, 24). MAb-HC02 and MAbE606 was provided by Dr. J. McCormick (Centers for Disease Control, Atlanta, Ga., Ruo et al., 1991, Arch. Virol. 119, 1–11).

Construction of SEOV M and S naked DNA plasmids. RT-PCR cloning of the M and S genome segments of SEOV, strain SR-11, was described previously (Arikawa et al., 1990, *Virology* 176, 114–125). The cDNA representing each genome segment was subcloned into the Not I or Bam HI site of a previously described naked DNA vector pWRG7077 (Schmaljohn et al., 1997, *J. Virol.* 64, 3162–3170). Plasmid DNA was purified using Qiagen maxiprep DNA purification kits according to the manufacturer's directions (Cat. no. 12163, Qiagen). The DNA we used for both intramuscular needle inoculation and epidermal gene gun inoculation was not prepared using endo-free qiagen DNA purification kits, and therefore, the DNA was not endotoxin-free (Qiagen plasmid kits yield ~9.3 endotoxin units per µg DNA [QIAGEN Plasmid Purification Handbook 01.97]). To control for possible immunostimulatory effects of endotoxin, our negative control plasmid DNA was prepared in precisely the same was as the vaccine candidates.

Construction of Hantavirus M gene DNA Vaccine Plasmids

Modified versions of pWRG/SEO-M were made as follows.

SEOV M DNA was amplified by polymerase chain reaction (PCR) from pWRG/SEO-M by using a forward primer [primer0, 5'-GCGCGCGGCCGCAGTAGTAGACTCCG-CAAGAAAC (SEQ ID NO:10)], and a reverse primer [BACK, 5'-GCGCGGATCCCGGGTACCGGGC-CCCCCTCG (SEQ ID NO:11)]. PCR product was cut with NotI and BamHI and then ligated into NotI-BamHI-cut pWRG7077 vector to create pWRG/SEO-M(0).

SEOV M DNA was amplified by PCR from pWRG/SEO-M(0) by using a forward primer [primer1–24, 5' GGC-CGCGGCCGCGGATCTGCAGGAATTCG-GCACGAGAGTAGTAGACTCCGCAAG AAACAGCA (SEQ ID NO:12], or [primer24–1, 5'-GGCCGCGGCCGC-GAGCACGGCTTAAGGACGTCTAGGAG-TAGTAGTCTCCGCAAG AAACAGCA (SEQ ID NO:13)], or [primer1–12, 5'-GGCCGCGGCCGCATTCGGCAC-GAGAGTAGTAGACTCCGCAAGAAACAGCA (SEQ ID NO:14], or [primer13–24, 5' GGCCGCGGCCGCGGATCT-GCAGGAAGTAGTAGACTCCGCAAGAAACAGCA (SEQ ID NO:15] or [primer1–24*, 5' GGCCGCGGC-CGCGGATCTGCCCGAATTCGGCAC-GAGAGTAGTAGACTCCGCAAG AAACAGCA (SEQ ID NO:16] or [primer1–8, 5'GGCCGCGGCCGCGGATCTG-CAGTAGTAGACTCCGCAAGAAACAGCA (SEQ ID NO:17] and the reverse primer BACK. PCR products were cut with NotI and BamHI and then ligated into NotI-BamHI-cut pWRG7077 vector to create, pWRG/SEO-M(1–24), pWRG/SEO(24–1), pWRG/SEO-M(1–12), pWRG/SEO-M(13–24), pWRG/SEO-M(1–24*), and pWRG/SEO-M(1–8), respectively.

To make pWRG/SEO-M(x), DNA encoding the SEOV G1/G2 proteins was amplified by PCR from pWRG/SEO-M by using primer1–24 and a reverse primer [SEOMX, 5'-GCGCGGATCCAGATTGGGAGATAGAAGAGAG (SEQ ID NO:18]. PCR product was cut with NotI and BamHI and then ligated into NotI-BglII-cut pWRG7077 vector. This clone was made to remove undesirable cloning artifact DNA (~100 nucleotides of the simian immunodeficiency virus nef gene) found between the BamHI and BglII sites of pWRG7077. Removing this sequence had no effect on expression of cloned genes (data not shown).

The HTNV M DNA vaccine plasmid, pWRG/HTN-M, was constructed essentially as follows. First, DNA encoding the HTNV G1/G2 was cut from pTZ19RHTNMm (Schmaljohn et al., 1989, supra) as a BglII fragment and ligated into BamHI-cut pWRG7077 vector. This plasmid expressed G2 but not G1 (data not shown). Next, the NotI-PshAI fragment of this plasmid, which contained the 5' end of the M gene, was excised and replaced with DNA amplified by PCR (from a puc18 plasmid containing a full-length HTNV M gene cloned by reverse transcriptase-PCR cloning from viral RNA), using primer1–24 (see above) and a reverse primer [M5B, 5'-TCAGGACTCCTGTCATGCAATAAGATCTC (SEQ ID NO:19]. The reverse primer included silent nucleotide changes in the HTNV M gene that created a BglII site used for diagnostic purposes. The PCR product was cut with NotI and PshAI and ligated into the NotI-PshAI-cut plasmid to create pWRG/HTN-M.

pWRG/HTN-M(x) was constructed by using primer1–24 and a reverse primer [HTNMX, 5'-GCGCGGATC-CGTTTGTGGTTAGAAAGCTAC (SEQ ID NO:20] to PCR amplify the HTNV M gene from pWRG/HTN-M. PCR product was cut with NotI and BamHI and ligated into the NotI-BglII-cut pWRG7077 vector. This clone was identical to pWRG/HTN-M; however, a portion of the 3' nontranslated region of the gene, and the vector sequence between NotI and BglII was removed.

pWRG/HTN-M(0) was constructed by using primer0 and reverse primer HTNMX to PCR amplify the HTNV M gene from pWRG/HTN-M(x). PCR product was cut with NotI and BamHI and ligated into the NotI-BamHI site of pWRG7077.

pWRG/HTN-M(1–24) was constructed by using primer1–24 and reverse primer HTNMX to PCR amplify the HTNV M gene from pWRG/HTN-M(O). PCR product was cut with NotI and BamHI and ligated into the NotI-BamHI site of pWRG7077.

Plasmid DNA was purified by using Qiagen maxiprep DNA purification kits according to the manufacturer's directions.

To construct the ANDV M gene-based DNA vaccine plasmid, pWRG/AND-M, viral RNA was isolated from ANDV-infected Vero E6 cells using TRIzol (Invitrogen, Carlsbad, Calif.) by standard methods. The RNA was reverse transcribed using Superscript II reverse transcriptase (Invitrogen) at 50° C. for 50 min, then inactivated by incubation at 70° C. 15 min. RNA was removed by digestion with RNaseH 37° C. for 20 min. Forward and reverse primers based on the published SNV and PUUV sequences, respectively, were included in the reverse transcription reaction: forward primer [SN-Fj, 5'-GGCCGCGGCCGC GGATCTGCAGGAATTCGGCACGAGAGTAGTAGAC TCCGCACG AAGAAGC (SEQ ID NO:21)] and reverse primer [PUUM-R, 5'-GCGCGGATCCTAGTAGTATGCT CCGCAGGAAC (SEQ ID NO:22)]. The forward primer included a Not I restriction site (underlined) and 24 nucleotides upstream of the M gene noncoding region that we previously found were important for expressing G1 in pWRG/HTN-M(x). The reverse primer included a BamH I restriction site (underlined). cDNA was purified by a PCR purification kit (Qiagen) and used as template in a PCR reaction. Primers SN-Fj and PUUM-R were included in the PCR reaction which included Platinum Taq High Fidelity DNA polymerase (Invitrogen): one 3-min cycle at 94° C. followed by 30 cycles of 94° C. 30 s, 68° C. 8 min. The PCR product was cut with NotI and BamHI and then ligated into NotI-BglII-cut pWRG7077 vector to produce pWRG/AND-M(1.1), hitherto referred to as pWRG/AND-M (SEQ ID NO:8). Plasmid DNA was purified using Qiagen maxiprep DNA purification kits according to the manufacturer's directions. At the time this plasmid was constructed, the ANDV M gene sequence was unknown, so we sequenced the M gene, and vector/insert junctions, using a primer walking technique and an ABI 3100 genetic analyzer.

Indirect Fluorescent Antibody Test (IFAT)

IFAT was a modification of a previously described procedure (Kamrud et al., 1995, *Exp. Parasitol.* 81, 394–403). COS cells grown on 15 mm glass cover slips in 12-well cell culture plates were transfected with 1 μg of plasmid DNA using Fugene6 (Boehringer Mannheim) as described by the manufacturer. Twenty-four hr posttransfection, cover slips were rinsed once with PBS (pH 7.4), fixed with acetone for 10 min at room temperature, and then reacted with anti-SEOV polyclonal antiserum (rabbit), or sera from vaccinated animals. Antibodies were diluted in PBS containing 3% fetal bovine serum (FBS) and then incubated on transfected cells for 30 min at 37° C. Cover slips were rinsed three times with PBS and incubated for 30 min at 37° C. with biotinylated donkey anti-rabbit followed by streptavidin conjugated fluorescein (Amersham), or fluorescein-labeled goat anti-hamster antibody (Kirkegaard & Perry Laboratories) diluted in PBS, 3% FBS. Evans blue (Fisher) was included in the secondary antibody solution as a counter stain. Cover slips were rinsed three times with PBS and once with deionized water and then were placed on a drop of fluorescence mounting medium (DAKO) on glass slides. Cells were observed with a Zeiss Axioplan fluorescence microscope.

For HTNV, Hamster sera were diluted 1:200 in PBS containing 3% FBS and then incubated on transfected cells for 1 h at 37° C. Cover slips were rinsed three times with PBS and incubated for 30 min at 37° C. with a fluorescein-labeled goat anti-hamster IgG antibody (Kirkegaard & Perry Laboratories). Hoechst stain (1 ug per ml) was included in the secondary antibody solution as a counter stain. Cover slips were rinsed three times with PBS, once with deionized water, and then placed on a drop of fluorescence mounting medium (DAKO) on glass slides. Cells were observed with a Nikon E600 fluorescence microscope.

Immunoprecipitation

COS cells grown in T-25 cell culture flasks were transfected with 5–8 μg of plasmid DNA with Fugene6 (Boehringer Mannheim). After 24 hr, expression products were radio-labeled with Promix ([$^{35}$S]-methionine and [$^{35}$S]-cysteine, Amersham) and immunoprecipitated as described previously (Schmaljohn et al., 1997, *Emerg. Infect. Dis.* 3, 95–104). Reduced samples were run on 4–12% Bis-Tris SDS PAGE gradient gels with 3-(N-morpholino) propane sulfonic acid (MOPS) running buffer (NuPage), at 200V constant voltage.

Vaccination with the Gene Gun

Cartridges for the gene gun were prepared as described previously (Eisenbraun et al., 1993, *DNA Cell. Biol.* 12, 791–797; Schmaljohn et al. 1997, supra). Briefly, ~1.5 μg of DNA was precipitated onto 0.5 mg of ~2 μm diameter gold beads (Degussa). DNA-coated gold beads were used to coat the inner surface of Tefzel tubing (McMaster-Carr). Cartridges were made by cutting the DNA-gold-coated Tefzel tubing into ~0.5-inch sections, each containing ~0.5 mg of gold, coated with ~0.75 μg of DNA (~50% of the precipitated DNA bound to the gold as determined by elution and fluorometric assay). To vaccinate animals, abdominal fur was removed with clippers and DNA-coated gold was administered to nonoverlapping sites on the abdominal epidermis by using the gene gun (Powderject-XR delivery device, Powderject Vaccines, Inc.) as described previously (Pertmer et al., 1995, *Vaccine* 13, 1427–1430). BALB/c mice (National Cancer Institute) and outbred Syrian hamsters (Charles River) were vaccinated with two or four cartridges, respectively, under 400 p.s.i. of helium pressure. This research was conducted in accordance with procedures described in the Guide for the Care and Use of Laboratory Animals (National Institute of Health, 1996). The facilities are fully accredited by the American Association for Accreditation of Laboratory Animal Care.

For HTNV, gene gun cartridges (~0.5 μg of plasmid DNA coated on 0.5 mg of gold) were prepared, and outbred golden Syrian hamsters were gene gun-vaccinated as described above. Hamsters were vaccinated three times at 3 week intervals. Rhesus macaques were vaccinated with the same cartridges and the same gene gun conditions used to vaccinate the hamsters; however, the monkeys received eight administrations per vaccination, rather than four.

Rhesus macaques were vaccinated with a recombinant vaccinia virus, rVV/HTN-M+S, by the method used to vaccinate humans in a Phase II clinical trial (McClain et al., 2000, supra). The vaccine ($3.4 \times 10^7$ PFU in a 0.5 ml of PBS) was injected subcutaneously into the right lateral upper arm with a 26G ⅜ inch needle. After 42 days, the monkeys received a identical boost vaccination on the left arm.

For ANDV, plasmid DNA was precipitated onto gold beads (3 μg of DNA per mg gold) and then the DNA-coated gold beads were coated on tubing. Gene gun cartridges consisting of ~0.75 μg of plasmid DNA coated on 0.5 mg of gold were prepared and stored at 4°C, desiccated, until use. Syrian hamsters were vaccinated with the Powderject XR1 particle-mediated epidermal delivery device (gene gun) (Powderject Vaccines, Inc., Madison, Wis.), four administrations per vaccination, at non-overlapping sites on the shaved abdominal epidermis using 400 p.s.i. of helium pressure. Rhesus macaques were vaccinated with the similar cartridges and the same gene gun conditions used to vaccinate the hamsters; however, the monkeys received eight administrations (four on abdomen and four over inguinal lymph nodes) per vaccination. Hamsters and monkeys were anesthetized during the non-painful gene gun procedure. The only visible effect was mild erythema at the sites of vaccination.

Vaccination by intramuscular needle inoculation. Plasmid DNA (25 μg) suspended in 50 μl of PBS (pH 7.4) was injected into the gastrocnemius muscle of anesthetized mice with a 28.5-gauge needle.

ELISA. To detect SEOV G1 and G2, ELISA plates (Costar) were coated with SEOV-infected Vero E6 cell lysates [⁻Co-irradiated (3 million rads) to inactivate virus] diluted in carbonate buffer (pH. 9.6) overnight at 4° C. Plates were blocked with PBS, 3% skim milk, 0.05% Tween-20 (blocking solution) for 1 hr at 37° C. and then washed once with PBS, 0.05% Tween-20 (wash solution). Mouse or hamster sera diluted in blocking solution were added to the wells, and plates were incubated as before. Plates were washed four times with wash solution and then incubated for 1 hr with horseradish peroxidase (HRP)-conjugated goat anti-mouse IgG (Cat. no. A-4416, Sigma) at a dilution of 1/1,000 or peroxidase-labeled goat anti-hamster antibody (Cat. no. 14-22-06, Kirkegaard & Perry Laboratories) diluted 1/2,000 in blocking solution. Plates were washed as before and then incubated for 10 min at room temperature with tetra-methylbenzidine substrate (TMB, Cat. no. 50-76-04, Kirkegaard & Perry Laboratories). The calorimetric reaction was stopped by adding Stop solution (Cat. no. 50-85-04, Kirkegaard & Perry Laboratories) and the optical density (O.D.), 450 nm, was determined. The method for detecting SEOV N-specific antibodies was adapted from a previously described technique (Elgh et al., 1997, *J. Clin. Microbiol.* 35, 1122–1130). Amino acids 1–117 of the nucleocapsid protein of SEOV (strain SR-11) were expressed as a histidine-tagged fusion protein by using the pRSET plasmid (Invitrogen) in *Escherichia coli* BL21 (DE3) (Novagen, Inc.) and purified by affinity chromatography on Ni-NTA columns (Qiagen). Antigen was diluted in carbonate buffer (pH 9.6), added to 96-well microtiter plates (Maxisorp; NUNC) (0.2 μg in 100 μl per well), and incubated overnight at 4° C. Plates were washed in deionized water and incubated with blocking solution for 30 min at room temperature. After plates were washed in deionized water, 100 μl of serum (diluted in blocking buffer containing *E. coli* antigen extract [0.6 mg/ml]) was added to duplicate wells. Plates were incubated at 37° C. for 1 h and again washed as before. Addition of HRP secondary antibody and calorimetric detection were added as described above for the SEOV G1-G2 ELISA. End-point titers were determined as the highest dilution with an O.D. greater than the mean O.D. value of serum samples from negative control plasmid (pWRG7077)-vaccinated animals plus three standard deviations. The SEOV N antigen was used to detect HTNV N-specific antibodies and the PUUV N was used to detect ANDV N-specific antibodies.

Plaque reduction neutralization tests (PRNT). Neutralization assays were performed essentially as previously described (Chu et al., 1995, *J. Virol.* 69, 6417–6423). Serum samples were diluted in cEMEM and then combined with an equal volume (111 μl) of cEMEM containing ~75 PFU of SEOV. This serum-virus mixture was incubated overnight at 4° C. and then 200 μl/well was added to 6 well plates containing Vero E6 monolayers 3–7 days old. After a 1-hr adsorption at 37° C., 3 ml of overlay medium (Earl's basal minimal essential medium (EBME), 10 mM HEPEs, 0.6% agarose [Sea Kem ME agarose], 8 mM L-glutamine, antibiotics) containing 10% FBS and 1× nonessential amino acid mixture (GIBCO BRL) was added to each well. Plates were incubated at 37° C. for 7 days and then stained by adding 2 ml/well of overlay medium containing 5% FBS and 5% neutral red solution (GIBCO BRL). Plaques were counted after 2 days at 37° C. Serum samples were heat inactivated (56° C., 30 min) before assay. In experiments where complement was used, serum and virus were incubated overnight in the presence of 5% guinea pig complement (Cat. no. ACL-4051, Accurate Chemical and Scientific Corporation). HTNV, SEOV, ANDV, and BCCV PRNT were stained with neutral red after 1 week and PUUV, DOBV, and SNV PRNT were stained after 9 days. Plaques were counted 2–3 days (37° C.) after staining.

Challenge with SEOV. Syrian hamsters were injected intramuscularly (caudal thigh) with a 25-gauge needle with $10^3$ PFU of SEOV diluted in 0.2 ml sterile PBS (pH 7.4). The $10^3$ PFU dose was based on previously pulished work that reported 100% infection of hamsters after this challenge dose and route (Schmaljohn et al., 1990, supra; Chu et al., 1995, supra). Twenty-eight days after challenge, the hamsters were anesthetized and exsanguinated by cardiac puncture. Postchallenge serum was evaluated for the presence of anti-SEOV antibody by IFAT, ELISA, and PRNT. A dramatic rise in postchallenge antibody titer to viral proteins other than the immunogens indicated that the hamster was infected with SEOV.

For HTNV and ANDV, pre- and postchallenge serum was evaluated for the presence of N-specific antibody by ELISA, and neutralizing antibody by PRNT. Detecting postchallenge N-specific antibody indicated that the hamster was infected with the challenge virus.

The challenge dose for HTNV was 2,000 PFU, which is ~1000 $LD_{50}$ (unpublished data). The challenge dose for ANDV was 2,000 PFU, which is 250 $LD_{50}$. Work involving ANDV-infected hamsters was performed in a biosafety level 4 (BSL-4) laboratory. Work involving HTNV-infected hamsters was performed while wearing a 3M-RACAL hood and TYVEK suit in a biosafety level 3 (BSL-3) laboratory. The effect of vaccine on survival outcome was assessed using a logistic regression model. Analysis was conducted using SAS Version 8.2 (SAS Institute Inc., SAS OnlineDoc, Version 8, Cary, N.C. 2000).

All animal research was conducted in accordance with procedures described in the Guide for the Care and Use of Laboratory Animals (National Institutes of Health, Bethesda, Md., 1996). The facilities are fully accredited by the American Association of Acccreditation of Laboratory Animal Care.

Cross protection assay. Groups of 4–5 hamsters were vaccinated with either pWRG/SEO M or negative control plasmid (pWRG7077). Vaccinations consisted of four gene gun administrations (~1.5 ug DNA per administration) three times at three week intervals. Three weeks after the final vaccination, prechallenge serum samples were obtained and the hamsters were challenged with 1,000 PFU of Hantaan virus, 1,000 PFU of Dobrava virus, or 1,000–2,000 PFU of Puumala virus. Twenty-eight days after challenge postchallenge serum samples were obtained. Pre and postchallenge serum samples were evaluated by anti-N ELISA to detect antibody to nucleocapsid, by a Hantaan, Dobrava, or Puumula plaque reduction neutralization test (PRNT) to detect the resective neutralizing antibodies depending on the challenge virus.

Antibody injections. Lyophilized human convalescent plasma from a human HPS patient was resuspended in water and recalcified before use by adding $CaCl_2$ to 0.1 M, incubation at 37° C. for 4 h, at 4° C. overnight, and at −20° C. for 1 h. The treated plasma was thawed, centrifuged at 10,000×G for 20 min and the supernatant was collected. Monkey serum from DNA-vaccinated monkeys and human serum (PEL-FREEZ Biologics, Rogers, Ariz.) were heat inactivated (56° C. 30 min). One ml of serum or plasma was injected intraperitoneally (i.P.) into hamsters using a 1-ml syringe with a 25-ga, ⅝-inch needle.

EXAMPLE 1

Transient Expression of Hantavirus Genes.

The cDNA representing the M (SEQ ID NO:1) or S (SEQ ID NO:2) gene segment of the SR-11 strain of SEOV was subcloned into the naked DNA expression vector pWRG7077 downstream of the cytomegalovirus immediate early promoter to yield pWRG/SEO-M (SEQ ID NO:3) and pWRG/SEO-S (SEQ ID NO:4), respectively (FIG. 1). To assess expression by the M and S constructs, these plasmids were transfected into COS cells and the expressed proteins were either immunostained or immunoprecipitated. The presence of stained cells in transfected monolayers incubated with anti-SEOV polyclonal sera indicated that SEOV reactive protein(s) were expressed from both pWRG/SEO-M and pWRG/SEO-S (FIG. 2A). Radiolabeled expression products were immunoprecipitated with anti-SEOV polyclonal antisera and analyzed by SDS-PAGE (FIG. 2B). Immunoprecipitated proteins had apparent molecular sizes expected for G1, G2, and N (80 kDa, 56 kDa, and 48 kDa)(Elliot et al. 1984, *J. Gen. Virol.* 65, 1285–1293; Schmaljohn et al. 1986, *Virology* 155, 633–643). Additional protein bands with apparent molecular masses of ~37 kDa and ~28 kDa were co-precipitated with N. These polypeptides were immunoprecipitated by a N amino-terminus-specific monoclonal antibody, and could be detected by Western blot, suggesting they represent truncated forms of N (data not shown).

EXAMPLE 2

Figure 3A:
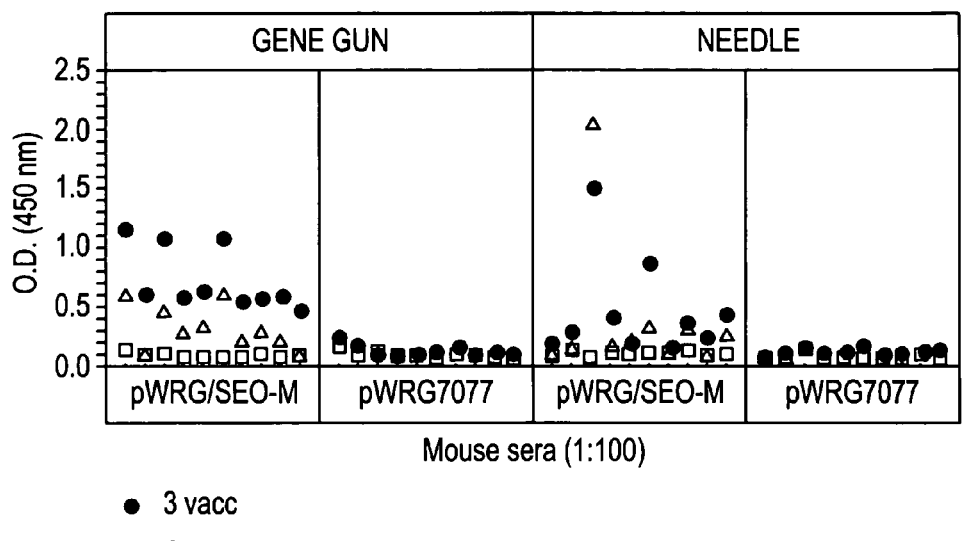
FIGS. 3A and 3B. Antibody responses (ELISA) of mice vaccinated with SEOV naked DNA by gene gun or intramuscular needle inoculation. The antibody responses to vaccination with pWRG/SEO-M (panel A) or pWRG/SEO-S (panel B) by gene gun or intramuscular needle inoculation were evaluated by ELISA. Mice vaccinated with negative control plasmid pWRG7077 were evaluated in both ELISAs. Prebleed sera and sera collected 4 weeks after the first vaccination (1 vacc), 4 weeks after the second vaccination (2 vacc), 3 weeks after the final vaccination (3 vacc) were all tested in a single assay. Symbols represent the average values of individual mice serum samples assayed in duplicate.
Figure 3B:
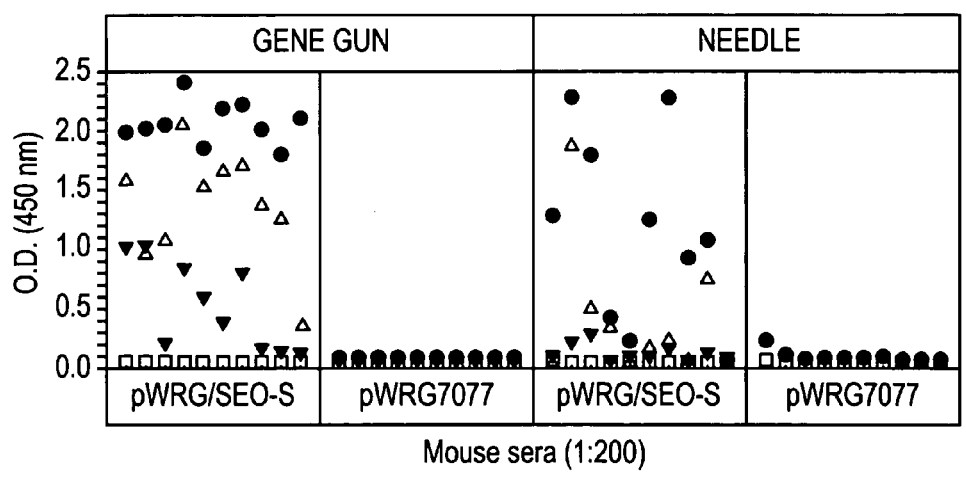

Vaccination of mice with pWRG/SEO-M or pWRG/SEO-S. To determine if either the M or S construct could elicit an antibody response in mice, groups of 10 6- to 8-week-old female BALB/c mice were vaccinated with pWRG/SEO-M, pWRG/SEO-S, or negative control DNA (pWRG7077) by two different routes: inoculation of the epidermis by gene gun, or inoculation of the gastrocnemius muscle by needle injection. Mice received a priming vaccination followed by two boosts at 4 week intervals. Blood samples collected before each vaccination and 3 weeks after the final boost were screened for a SEOV-specific antibody response by ELISA. Both the M and S constructs elicited a SEOV-specific antibody response by both routes of DNA administration (FIG. 3). Most mice vaccinated with SEOV S by gene gun exhibited specific antibodies after only one vaccination, and the antibody responses increased after subsequent vaccinations (FIG. 3B). To compare the relative antibody responses, end-point ELISA titers were determined for the final blood samples (Table 1). Gene gun vaccination resulted in higher seroconversion frequencies and geometric mean titers (GMT) than intramuscular vaccination with either construct.

TABLE 1

ELISA Titers in Mice Vaccinated with SEOV Naked DNA Vaccines

| Inoculated DNA | Vaccine route[a] | Positive/ total | End point titer range | GMT[b] |
|---|---|---|---|---|
| pWRG/SEO-M | g.g. | 9/10 | 200–1600 | 303 |
| pWRG/SEO-M | i.m. | 7/10 | 100–400 | 132 |
| pWRG/SEO-S | g.g. | 10/10 | 6400–12800 | 7352 |
| pWRG/SEO-S | i.m. | 9/10 | 800–6400 | 1213 |

Note. Mice were vaccinated three times at 4-week intervals. Titers were determined for sera collected three weeks after the final boost.
[a]g.g. indicates gene gun; i.m., intramuscular needle inoculation.
[b]Geometric mean titer of all animals in group.

Figure 4:
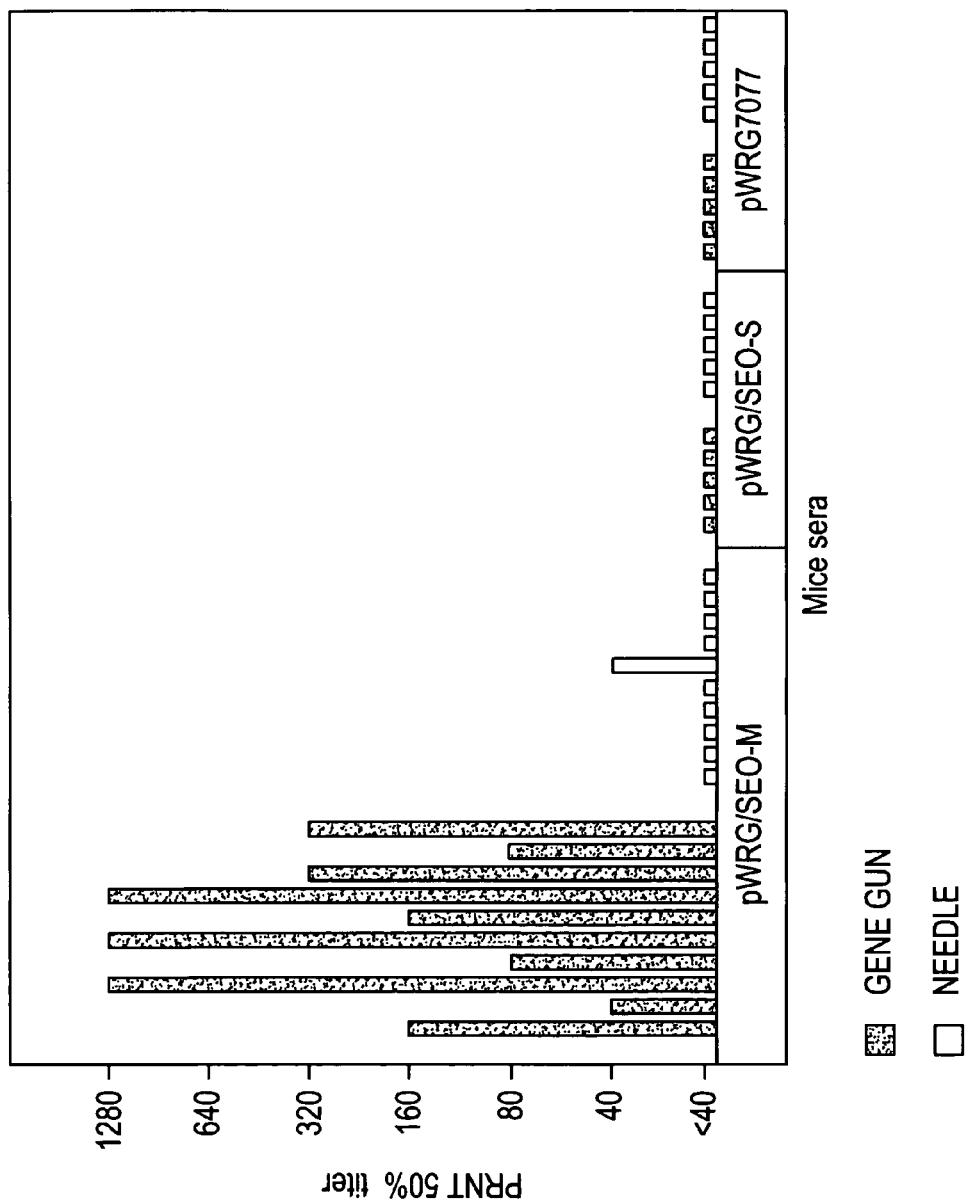
FIG. 4. Neutralizing antibody responses of mice vaccinated with SEOV naked DNA. PRNT were performed on mice sera collected 3 weeks after the third vaccination by either gene gun or intramuscular needle injection (needle). Bars represent sera from individual mice vaccinated with the indicated immunogen. Sera were heat inactivated (56° C., 30 min) and the assay was performed in the presence of 5% guinea pig complement. $PRNT_{50}$% titers are expressed as reciprocal of the highest serum dilution resulting in a 50% reduction in plaque number.
Figure 5:
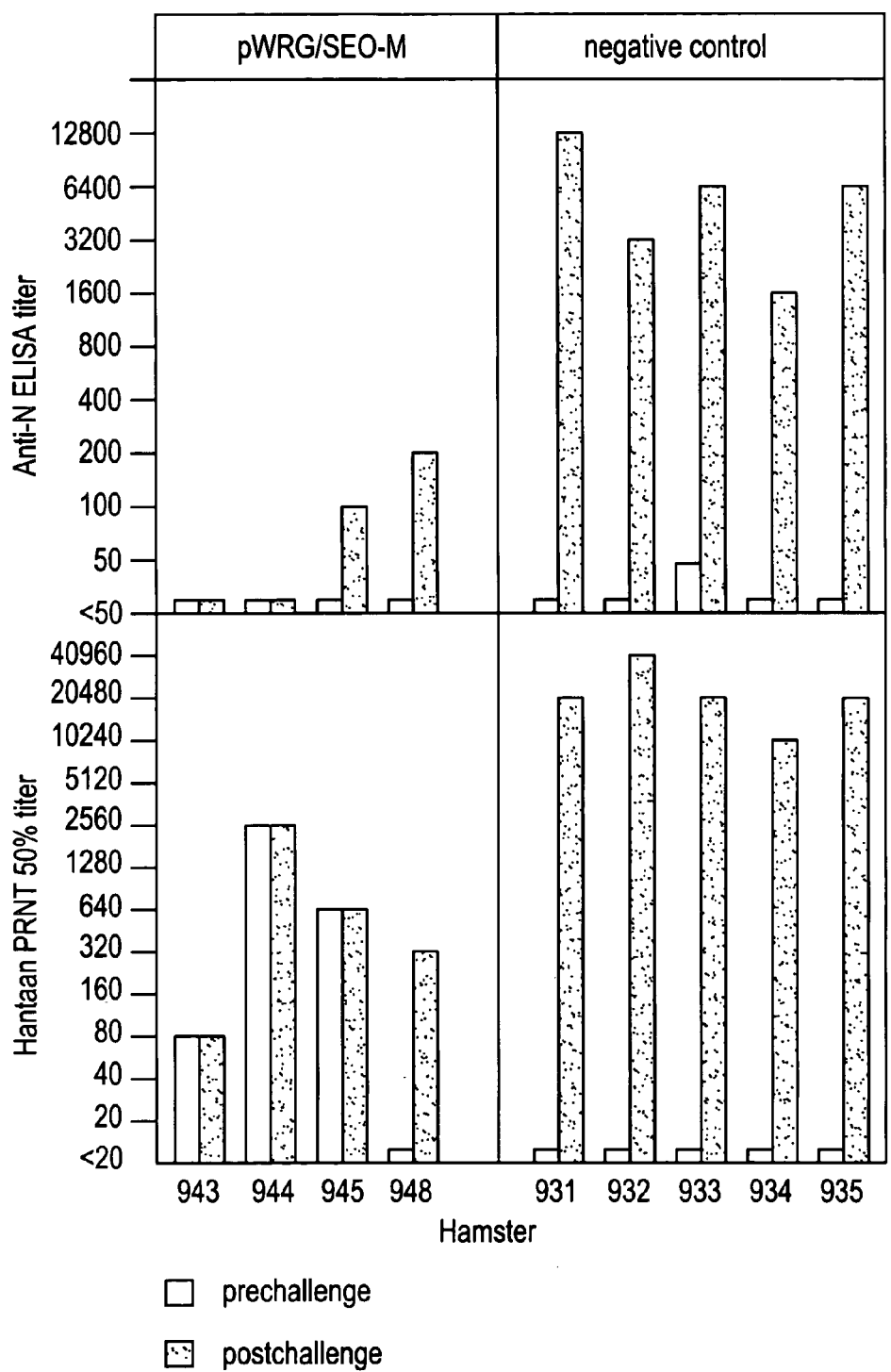
FIG. 5. Vaccination with pWRG/SEO-M cross-protects against infection with Hantaan virus. Groups of 4–5 hamsters were vaccinated with either pWRG/SEO-M or negative control plasmid (pWRG7077) as described in Methods below. Three weeks after the final vaccination, prechallenge serum samples were obtained and the hamsters were challenged with 1,000 PFU of Hantaan virus. Twenty-eight days after challenge postchallenge serum samles were obtained.

To determine if naked DNA vaccination elicited neutralizing antibodies, we performed plaque reduction neutralization tests (PRNT) on sera collected 3 weeks after the final boost. All (10/10) mice that were vaccinated with pWRG/SEO-M by gene gun exhibited $PRNT_{50\%}$ titers ranging from 40 to 1280 (FIG. 4). Only 1/10 mice vaccinated with pWRG/SEO-M by needle injection exhibited a detectable neutralizing antibody response ($PRNT_{50\%}$=40). Mice vaccinated with pWRG/SEO-S or pWRG7077 by either gene gun or needle inoculation did not develop neutralizing antibodies (FIG. 4).

EXAMPLE 3

Vaccination and challenge of hamsters. To study the protective efficacy of the naked DNA hantavirus vaccines, groups of five hamsters were vaccinated with either pWRG/SEO-M, pWRG/SEO-S, or negative control plasmid pWRG7077 by gene gun (a priming vaccination followed by two boosts at 4-week intervals) and then challenged with SEOV 6 weeks after the final boost. IFAT, ELISA, and PRNT were performed on serum samples taken before vaccination, on the day of challenge, and 4 weeks after challenge. Because there are no disease models for hantavirus in adult rodents, we evaluated whether or not our DNA vaccines could protect against infection rather than prevent disease.

IFAT and ELISA results demonstrated that before vaccination, none of the hamsters was positive for either SEOV G1-G2 or N protein (data not shown). After vaccination (prechallenge sera drawn on day of challenge), five of five hamsters vaccinated with pWRG/SEO-M developed anti-G1-G2 antibodies, and four of five hamsters vaccinated with the pWRG/SEO-S exhibited anti-N antibodies by IFAT (Table 2). The prechallenge ELISA results detected similar antibody responses except that only four of five pWRG/SEO-M vaccinated hamsters were positive in the anti-SEOV ELISA. The pWRG7077 vaccinated hamsters failed to develop both G1-G2- and N-specific antibodies by IFAT and ELISA before challenge.

After challenge, serum samples from hamsters previously vaccinated with pWRG/SEO-M remained negative for anti-nucleocapsid antibody by IFAT indicating the animals were not infected with SEOV. In contrast, postchallenge serum samples from pWRG/SEO-S and pWRG7077 vaccinated hamsters were positive for both G1-G2 and N antibodies, indicating that the animals were infected when challenged with SEOV. Postchallenge ELISA results were similar to the IFAT results; however, three of five of the pWRG/SEO-M vaccinated hamsters exhibited a weak anti-N response after challenge indicating that, although the IFAT were negative, the hamsters had developed antibodies to the challenge virus.

Before vaccination, none of the hamsters had SEOV neutralizing antibody titers (data not shown). After vaccination, all hamsters vaccinated with pWRG/SEO-M developed neutralizing antibodies with $PRNT_{80\%}$ titers ranging from 160 to 640 (Table 2). Neutralizing antibody was not detected in pWRG/SEO-S and pWRG7077 prechallenge sera from vaccinated hamsters. After SEOV challenge, neutralizing antibody titers of the pWRG/SEO-M immunized animals remained essentially the same as before challenge (plus or minus twofold). In contrast, the pWRG7077 and pWRG/SEO-S postchallenge neutralizing antibody titers increased significantly from <20 to between 1,280 and >81,920.

TABLE 2

Serological responses and protection of hamsters vaccinated with naked DNA vaccines.

| Vaccine[a] | Hamster | IFAT[b] anti-N pre | IFAT[b] anti-N post | IFAT[b] anti-G1-G2 pre | IFAT[b] anti-G1-G2 post | $PRNT_{50\%}$[c] pre | $PRNT_{50\%}$[c] post | Protection |
|---|---|---|---|---|---|---|---|---|
| pWRG/SEO-M | 1 | − | − | + | + | 320 (20) | 640 | yes |
|  | 2 | − | − | + | + | 320 (40) | 640 | yes |
|  | 3 | − | − | + | + | 320 (20) | 1280 | yes |
|  | 4 | − | − | + | + | 80 (<20) | 160 | yes |
|  | 5 | − | − | + | + | 640 (20) | 1280 | yes |
| PWRG/SEO-S | 1 | + | + | − | + | <20 (<20) | >640 | no |
|  | 2 | + | + | − | + | <20 (<20) | >640 | no |
|  | 3 | + | + | − | + | <20 (<20) | >640 | no |
|  | 4 | + | + | − | + | <20 (<20) | >640 | no |
|  | 5 | − | + | − | + | <20 (<20) | >640 | no |
| PWRG 7077 | 1 | − | + | − | + | <20 (<20) | >640 | no |
|  | 2 | − | + | − | + | <20 (<20) | >640 | no |
|  | 3 | − | + | − | + | <20 (<20) | >640 | no |
|  | 4 | − | + | − | + | <20 (<20) | >640 | no |
|  | 5 | − | + | − | + | <20 (<20) | >640 | no |

[a]Three vaccinations consisting of 4 gene gun cartridges (about 1.5 ug/cartridge) administered at 4 week intervals.
[b]Sera were screened at 1:200 in IFAT sing pWRG/SEO-S or pWRG/SEO-M trasnfected cells as target antigen for anti-n and anti-G1-G2, respectively.
− indicates no reactivity;
+ indicates reactivity.
[c]PRNT values are reciprocal serum dilutions reducing plaque number by 50%. Assays were performed in the presence of 5% guinea pig complement. Numbers in parenthesis are PRNT values of heated serum in the absence of complement.
pre, prechallenge serum samples from day of challenge;
post, poschallenge serum samples from 4 weeks post challenge.

During the course of this study, we observed that PRNT titers decreased dramatically if sera were heat-inactivated (56° C., 30 min). To test the possibility that the neutralizing activity was complement-enhanced, we performed PRNT assays in the presence of 5% guinea pig complement and found that adding complement increased the PRNT titers of heated serum 4- to 32-fold (Table 2). Complement alone had no effect on SEOV plaque number (data not shown).

EXAMPLE 4

Vaccination with pWRG/SEO-M Cross-Protects Against Infection with Hantaan Virus

Hamsters vaccinated with pWRG/SEO-M had no detectable anti-N antibody prior to challenge, and the postchallenge anti-N response was undetectable or very low (<=1:200) (FIG. 6). In contrast, hamsters vaccinated with the negative control plasmid exhibited a drammatic rise in anti-N antibody (~2 log increase over background). The PRNT indicated that vaccination with pWRG/SEO-M elicited detectable levels of cross neutralizing antibodies in 3 of 4 hamsters. The PRNT titers of these hamsters did not rise after challenge. In the one hamster with undetectable (<1:20) Hantaan neutralizing antibody, the PRNT titer did rise; however, the increase was at least 32-fold lower than that seen in the hamsters vaccinated with the negative control plasmid.

The low or absent increase in antibody titers to Hantaan structural proteins (as measured by ELISA and PRNT) after challenge with Hantaan virus indicates that vaccination with the Seoul virus M gene (pWRG/SEO-M) confers protection against infection with Hantaan virus.

EXAMPLE 5

Vaccination with pWRG/SEO-M Cross-Protects Against Infection with Dobrava Virus.

Hamsters vaccinated with pWRG/SEO-M had no detectable anti-N antibody prior to challenge, and the postchallenge anti-N response was undetectable. In contrast, all but one of the hamsters vaccinated with the negative control plasmid exhibited a drammatic rise in anti-N antibody (postchallenge anti-N titers of between 1:200 and 1:204,800). The PRNT indicated that vaccination with pWRG/SEO-M elicited low levels of cross neutralizing antibodies in 5 of 5 hamsters. The PRNT titers of these hamsters did not rise above 1:80 after challenge. In contrast, all but one hamster vaccinated with the negative control plasmid exhibited a high postchallenge PRNT (1:5120) indicating the hamsters were infected with Dobrava virus. It remains unclear why animal #182 was not infected.

The low or absent increase in antibody titers to Dobrava structural proteins (as measured by ELISA and PRNT) after challenge with Dobrava virus indicates that vaccination with the Seoul virus M gene (pWRG/SEO-M) confers protection against infection with Dobrava virus.

EXAMPLE 6

Vaccination with pWRG/SEO-M Fails to Cross-Protect Against Infection with Puumala Virus.

Hamsters vaccinated with pWRG/SEO-M had no detectable anti-N antibody prior to challenge. After challenge, all but one hamster had postchallenge anti-N response greater than or equal to 1:200 indicating the hamsters were infected with Puumala virus. The negative control hamsters had similar pre and postchallenge anti-N titers. The PRNT resulsts indicated that, although vaccination with pWRG/SEO-M elicited neutralizing antibodies against Seoul virus (empty circles), these antibodies did not cross-neutralizing Puumala virus, and failed to protect against infection. The postchallenge Puumala virus PRNT titers of the pWRG/SEO-M vaccinated and negative control vaccinated hamsters were all similar (greater than or equal to 1:160), eept one negative control hamster that was not infected. It remains unclear why negative control animal #220 was not infected.

The increase in antibody titers to Puumala virus structural proteins (as measured by ELISA and PRNT) after challenge with Puumala virus indicates that vaccination with the Seoul virus M gene (pWRG/SEO-M) fails to confers protection against infection with Puumala virus. It should be noted that the hamster with the highest prechallenge anti-Seoul virus PRNT titer was 1:640 (animal #209). It is possible that animals with higher prechallenge neutralizing antibody titers might be cross-protected against Puumala virus.

DISCUSSION

We report that naked DNA shows promise as a way to vaccinate against hantaviruses. Our results demonstrate that vaccination with cDNA representing either the SEOV M or S genome segment elicited antibody responses in BALB/c mice and Syrian hamsters. Hamsters vaccinated with DNA expressing the M segment, but not S segment, developed neutralizing antibodies and were protected against infection with SEOV.

In our initial immunogenicity experiments, gene gun vaccination of BALB/c mice resulted in higher seroconversion rates than intramuscular needle inoculation for both pWRG/SEO-M and pWRG/SEO-S, as measured by ELISA and PRNT. These preliminary data prompted us to focus on the gene gun rather than the intramuscular route of DNA delivery. However, because only one intramuscular DNA dose was tested (25 µg per animal), it is possible that the seroconversion rate and/or titers could be increased by adjusting parameters such as the amount of DNA injected, site of injection, or vaccination schedule. It is also possible that needle inoculation elicited a predominantly cell-mediated rather than humoral response to the DNA vaccination, as has been seen by others (Feltquate et al., 1997, *J. Immunol.* 158, 2278–2284; Robinson and Torres, 1997, *Semin. Immunol.* 9, 271–283; Gregoriadis, 1998, *Pharm. Res.* 15, 661–670).

Gene gun vaccination with pWRG/SEO-M protected all hamsters against infection with SEOV as measured by 1) undetectable, or barely detectable, postchallenge anti-N antibody response and, 2) PRNT titers that remained essentially unchanged after SEOV challenge. Although the IFAT results indicated that none of the pWRG/SEO-M vaccinated hamsters developed anti-N antibodies after challenge, the more sensitive anti-N ELISA revealed that three hamsters had a weak anti-N antibody response. Because the postchallenge anti-N ELISA GMT of these hamsters (GMT=50) was more than 50 times lower than the negative control pWRG7077 vaccinated hamsters (GMT>3,195), it is likely the anti-N antibodies represent an antibody response to either the input SEOV antigen (no replication), or to a limited infection (e.g., one round of replication). The PRNT data provided additional evidence that vaccination with pWRG/SEO-M, but not pWRG/SEO-S, protected hamsters from SEOV infection. Whereas the negative control pWRG7077-vaccinated hamsters' PRNT titers increased from <20 to between 10,280 and 81,920 after challenge, the pWRG/SEO-M-vaccinated hamster PRNT titers remained within twofold of prechallenge levels. Moreover, the postchallenge PRNT titers of the pWRG/SEO-M-vaccinated hamsters (GMT=368) remained well below the postchallenge PRNT titers of the pWRG7077-vaccinated hamsters (GMT>27,024). Hamsters vaccinated with pWRG/SEO-S were infected with SEOV after challenge. The pWRG/SEO-S-vaccinated hamsters' postchallenge PRNT titers increased from <20 to between 2,560 and 20,480. Although the postchallenge PRNT titers of the pWRG/SEO-S were high (GMT=5,885), it is noteworthy that these titers were approximately fivefold lower than the negative control (pWRG7077) postchallenge titers (GMT>27,024).

The absence of a neutralizing antibody response in mice and hamsters vaccinated with pWRG/SEO-S, with or without complement, is consistent with published data that monoclonal antibodies to G1 and G2, but not N, have neutralizing activity (Dantas et al., 1986, *Virology* 151, 379–384; Arikawa et al., 1989, *J. Gen. Virol.* 70, 615–624; Schmaljohn et al., 1990, *J. Virol.* 64, 3162–3170; Arikawa et al., 1992, *Arch. Virol.* 70, 615–624), and that vaccination with vaccinia recombinants expressing G1 and/or G2, but not N, elicit a neutralizing response (Pensiero et al., 1988, *J. Virol.* 62, 696–702; Schmaljohn et al. 1992, *Vaccine* 10, 10–13; Xu et al., 1992, *Am. J. Trop. Med. Hyg.* 47, 397–404; Chu et al., 1995, supra).

Failure of an anti-N immune response to protect against infection was unexpected because others found that vaccination with recombinant N expressed in insect cells, bacteria, or as chimeric HBV core particles, protect against infection (Schmaljohn et al., 1990, supra; Yoshimatsu et al., 1993, *Arch. Virol.* 130, 365–376; Lundkvist et al., 1996, *Virology* 216, 397–406; Ulrich et al., 1998, *Vaccine* 16, 272–280). Also, vaccination with recombinant vaccinia viruses expressing the SEOV S segment partially protected gerbils from SEOV infection (Xu et al. 1992, supra). Failure of naked DNA vaccination with the S segment to protect hamsters in our experiments may be related to a quantitative rather than qualitative deficiency. Although four of five hamsters vaccinated with pWRG/SEO-S developed a detectable antibody response by IFAT and ELISA, the titers were relatively low (ELISA titers less than or equal to 1:1,600). The reason for these low anti-N antibody titers in hamsters, but not mice, remains unclear. Fault cannot lie with the gene gun cartridges as the same lot was used to vaccinate both hamsters and mice on the same day; and the mouse seroconversion rate was 90%, with an ELISA GMT of over 7,000. Low antibody titers may reflect a poor overall immune response to vaccination with pWRG/SEO-S in hamsters or, alternatively, it is possible that epidermal administration of S DNA with the gene gun results in a predominantly cell-mediated, rather than humoral, response to N. Nevertheless, our findings demonstrate that there was a detectable anti-N immune response in four of five hamsters after naked DNA gene gun vaccination with pWRG/SEO-S, and that this response, whether humoral and/or cell-mediated, was insufficient to protect against SEOV infection. The fivefold difference in postchallenge PRNT titers of pWRG/SEO-S versus pWRG7077 vaccinated hamsters suggests pWRG/SEO-S vaccination may nonetheless limit SEOV infection.

We found that SEOV neutralizing activity elicited in mice and hamsters was reduced 4- to 32-fold if the sera was heat inactivated (56° C., 30 min). This loss in neutralizing activity could be completely reversed if guinea pig complement was included in the PRNT. These data are consistent with those of others who reported that hantavirus neutralizing activity in sera from humans, mice, and especially rats, was enhanced by complement (Takenaka et al., 1985, *Arch. Virol.* 84, 197–206; Asada et al., 1989, *J. Gen. Virol.* 70, 819–825). The observation that complement plays a major role in hantavirus neutralization is notable because PRNT titers are commonly used to assess the immunogenicity and predicted efficacy of hantavirus vaccines. Conditions that deplete or add complement, such as heat inactivation or addition of exogenous complement (e.g., as a purified protein fraction or as fresh animal sera), could alter PRNT titers and, therefore, could alter the assessment of candidate vaccines.

EXAMPLE 7

Expression of G1 and G2 from HTNV M DNA vaccine. cDNA representing the HTNV M genome segment was cloned into a cytomegalovirus (CMV) promoter-based expression plasmid, pWRG7077, to create pWRG/HTN-M. Radio-immunoprecipitation assay (RIPA) experiments using polyclonal and monoclonal antibodies (MAbs) indicated that both the G1 and G2 proteins were transiently expressed in cells transfected with pWRG/HTN-M (FIG. 8).

Earlier attempts to develop a functional HTNV M DNA vaccine were unsuccessful (i.e., G2 but not G1 was expressed)(unpublished data). We solved this problem after discovering that our SEOV M plasmid (pWRG/SEO-M) failed to efficiently express G1 if a 24 base pair (bp) sequence of extraneous DNA, found between the vector NotI cloning site and the SEOV M noncoding region (FIG. 9A), was removed. This extraneous DNA originated from procedures used during earlier cloning and subcloning of the SEOV M gene. The SEOV M construct with the 24 bp sequence removed failed to express G1, but did express G2 (FIG. 9B). Expression of G1 was restored if the 24 bp sequence was engineered back into the construct in the forward but not reverse orientation (FIG. 9B). This result indicated that the nucleotide sequence, not nucleotide number, affected G1 expression. To map the sequence that allowed efficient G1 expression, we made constructs which included either nucleotides 1–12 or 13–24 of the extraneous sequence. G1 was expressed when nucleotides 1–12 but not 13–24 was present in the plasmid (FIG. 9B). We noted that nucleotides 4–10 of the DNA (TCTGCAG) were identical to the last seven nucleotides of intron A (i.e., splice acceptor site)(Stenberg et al., 1984, supra). Mutating the putative splice acceptor dinucleotide AG to CC did not influence the expression of G1, suggesting that, if this region is involved in splicing, it is not dependent on maintaining the exact sequence of the intron A splice site (FIG. 9B). We made a construct containing nucleotides 1–8 of the extraneous DNA and found this was sufficient to restore efficient expression of G1 (FIG. 9C). Thus, we determined that the sequence GGATCTGC, located between the NotI cloning site and the 5' noncoding region of the SEOV M gene, was required for efficient expression of GI from pWRG7077-based DNA vaccines.

Based on the SEOV M findings, we postulated that including the extraneous sequence upstream of the HTNV M gene might allow us to solve our inability to express both HTNV G1 and G2 from a DNA vaccine plasmid. We constructed a plasmid that included the extraneous sequence upstream of the HTNV M gene and, in doing so, obtained a clone that expressed both G1 and G2, pWRG/HTN-M (FIG. 9D). When the extraneous sequence was removed, G1 was not expressed, and when it was restored, G1 was efficiently expressed (FIG. 9D). These data confirmed that the extraneous sequence was not only required for successful expression of SEOV G1, but also of HTNV G1. This sequence had no influence on expression of G2 from either SEOV or HTNV (FIG. 9). The mechanism by which the extraneous sequence affects G1 expression but not G2 expression remains unknown.

EXAMPLE 8

DNA Vaccination with pWRG/HTN-M Elicits Neutralizing Antibody and Protects Hamsters Against Infection with HTNV To determine if the HTNV M DNA vaccine plasmid was immunogenic, we used a gene gun to vaccinate hamsters with either pWRG/HTN-M (pWRG/HTN-M or pWRG/HTN-M(x), see Methods), or a negative control. Three weeks after the final vaccination, the hamsters were bled and sera were evaluated for neutralizing antibody by a plaque-reduction neutralization test (PRNT). In two separate experiments, all of the hamsters vaccinated with pWRG/HTN-M developed HTNV-neutralizing antibody responses (FIG. 11). Titers ($PRNT_{80}$%) ranged from 20–1280 with a geometric mean titer (GMT)=104 in the first experiment and 20–10240, GMT=493, in the second experiment. Negative control groups remained seronegative. Thus, gene gun vaccination with pWRG/HTN-M was immunogenic in hamsters.

To determine the protective efficacy of pWRG/HTN-M we used an infection model described previously (Hooper et al., 1999, supra). The model involves challenging vaccinated hamsters with virus, and after 4 weeks, using serological assays to detect evidence of infection. Specifically, if a challenged hamster developed antibodies to hantavirus N protein (which is not a component of the vaccine), then that hamster was considered to be infected. On the other hand, if a challenged hamster failed to develop a N-specific antibody response, then that hamster was not infected (i.e, protected against infection). A greater than fourfold increase in the neutralizing antibody response after challenge also served as a marker for evidence of infection.

Vaccinated hamsters were challenged with 2,000 plaque-forming units ($ID_{50}$ is approximately 2 plaque-forming units [PFU], unpublished data) of HTNV intramuscularly (i.m.). Four weeks after challenge, blood samples were collected and sera were tested for N-specific antibody by ELISA, and for neutralizing antibody by PRNT. The pre- and postchallenge anti-N titers and PRNT titers are shown in (FIG. 11). All of the hamsters that were vaccinated with pWRG/HTN-M were protected against infection as defined by an absence of a postchallenge N-specific antibody response. In addition, the pre- and postchallenge PRNT titers differed ≦ fourfold. In contrast, all of the negative control hamsters, whether they were vaccinated with pWRG7077 or remained unvaccinated, were infected as evidenced by the development of N-specific antibodies and neutralizing antibodies postchallenge. Thus, gene gun vaccination with pWRG/HTN-M (or pWRG/HTN-M(x)) protected against productive infection with HTNV, even when the prechallenge $PRNT_{80\%}$ titer was as low as 20.

EXAMPLE 9

DNA Vaccination with Either pWRG/SEO-M or pWRG/HTN-M Cross-Protects Against Challenge with Heterotypic Hantaviruses Having determined that our SEOV M and HTNV M gene-based DNA vaccines were capable of protecting hamsters against infection with homotypic virus, we wanted to determine if either of these vaccines could cross-protect against other HFRS-associated hantaviruses. We first measured the cross-neutralizing activities of sera from HFRS hantavirus-infected hamsters, and hamsters vaccinated with either the SEOV M or HTNV M vaccine (Table 3). We found that sera from SEOV-infected hamsters had a low level of HTNV neutralizing activity, and no detectable DOBV or PUUV neutralizing activity. Sera from HTNV- or DOBV-infected hamsters exhibited a low level of neutralizing antibody against SEOV, DOBV, and PUUV. Sera from PUUV-infected hamsters failed to neutralize HTNV or SEOV, and had a barely detectable DOBV-neutralizing activity. The sera from vaccinated hamsters exhibited greater levels of cross-neutralizing activity than sera from the infected hamsters. Vaccination with either pWRG/SEO-M or pWRG/HTN-M elicited an antibody response that cross-neutralized SEOV, HTNV, and DOBV, but not PUUV.

TABLE 3

Cross-neutralization activity in serum from infected, or DNA-vaccinated hamsters

| | PRNT | | | | | | | |
|---|---|---|---|---|---|---|---|---|
| | SEOV | | HTNV | | DOBV | | PUUV | |
| Serum source[a] | 80% | 50% | 80% | 50% | 80% | 50% | 80% | 50% |
| Infected[b] with SEOV | 640 | 5120 | * | 80 | * | * | * | * |
| Infected with HTNV | * | 160 | 1280 | 5120 | 40 | 320 | * | 20 |
| Infected with DOBV | 20 | 320 | 20 | 160 | 2560 | 10240 | * | 40 |
| Infected with PUUV | * | * | * | * | * | 20 | 5120 | 20480 |
| Vaccinated[c] with pWRG/SEO-M | 5120 | 10240 | 320 | 320 | 160 | 320 | * | * |
| Vaccinated with pWRG/HTN-M | 40 | 80 | 5120 | 5120 | 160 | 640 | * | * |

[a]Pool of serum from three to four hamsters with homotypic titer of at least 160. Serum was collected 4 weeks after infection, or 3 weeks after the final DNA vaccination.
[b]Hamsters injected i.m. with 2,000 PFU of the indicated virus.
[c]Hamsters gene gun-vaccinated three times at 3 week intervals with the indicated DNA vaccine plasmid.
[d]PRNT values are the reciprocal serum dilution that neutralizes the indicated virus plaque number by 80% or 50%. Homotypic titer are shown in bold.
* titer less than 20

Figure 12A:
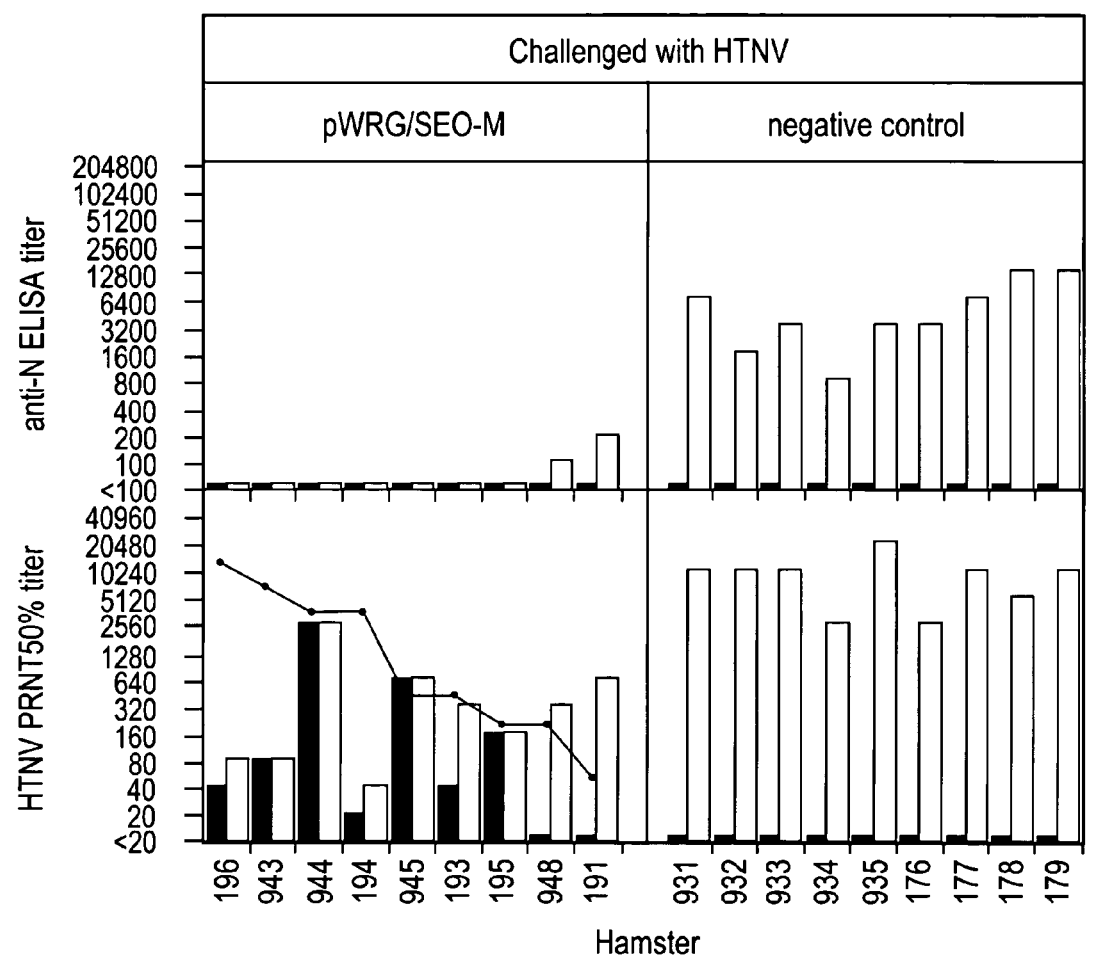
Figure 12B:
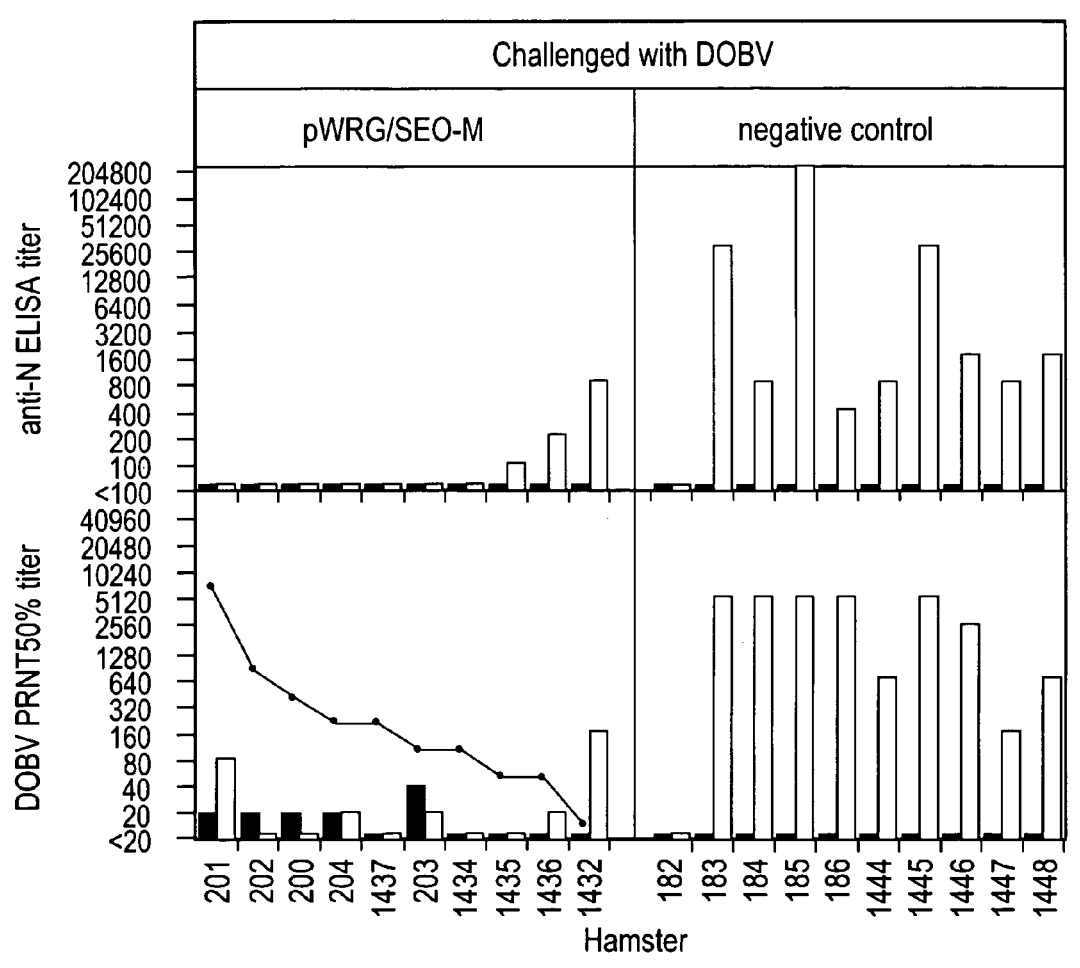
Figure 12C:
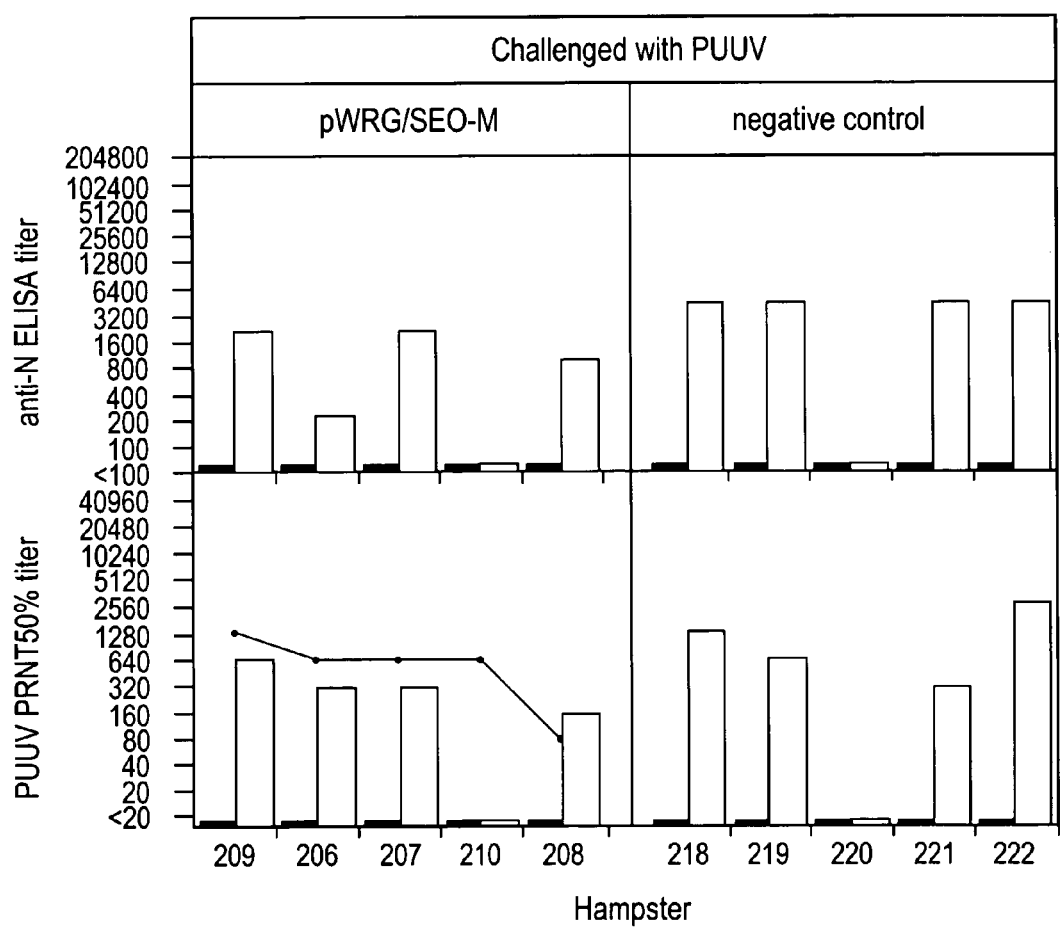

We previously demonstrated that the SEOV M DNA vaccine protected most hamsters not only from SEOV but also from challenge with HTNV (Kamrud et al., 1999, Virology 263, 209–219). To confirm those findings, and to further evaluate the capacity of the SEOV M vaccine to cross-protect against other hantaviruses, we tested pWRG/SEO-M for protective efficacy against HTNV, DOBV, and PUUV. The results of this study indicated that hamsters vaccinated with pWRG/SEO-M were protected against HTNV and DOBV but not PUUV as determined by the absence of anti-N antibody response after challenge (FIG. 12). A homotypic PRNT$_{80\%}$ titer >160 protected against HTNV, and a titer (80 protected against DOBV, but a titer as high as 1280 failed to protect against PUUV (FIGS. 12A, 12B and 12C). One vaccinated and one control hamster failed to respond to the PUUV challenge, probably because the PUUV challenge dose was 10 ID$_{50}$, whereas it was 1000 ID$_{50}$ for the other viruses (unpublished data).

Figure 12D:
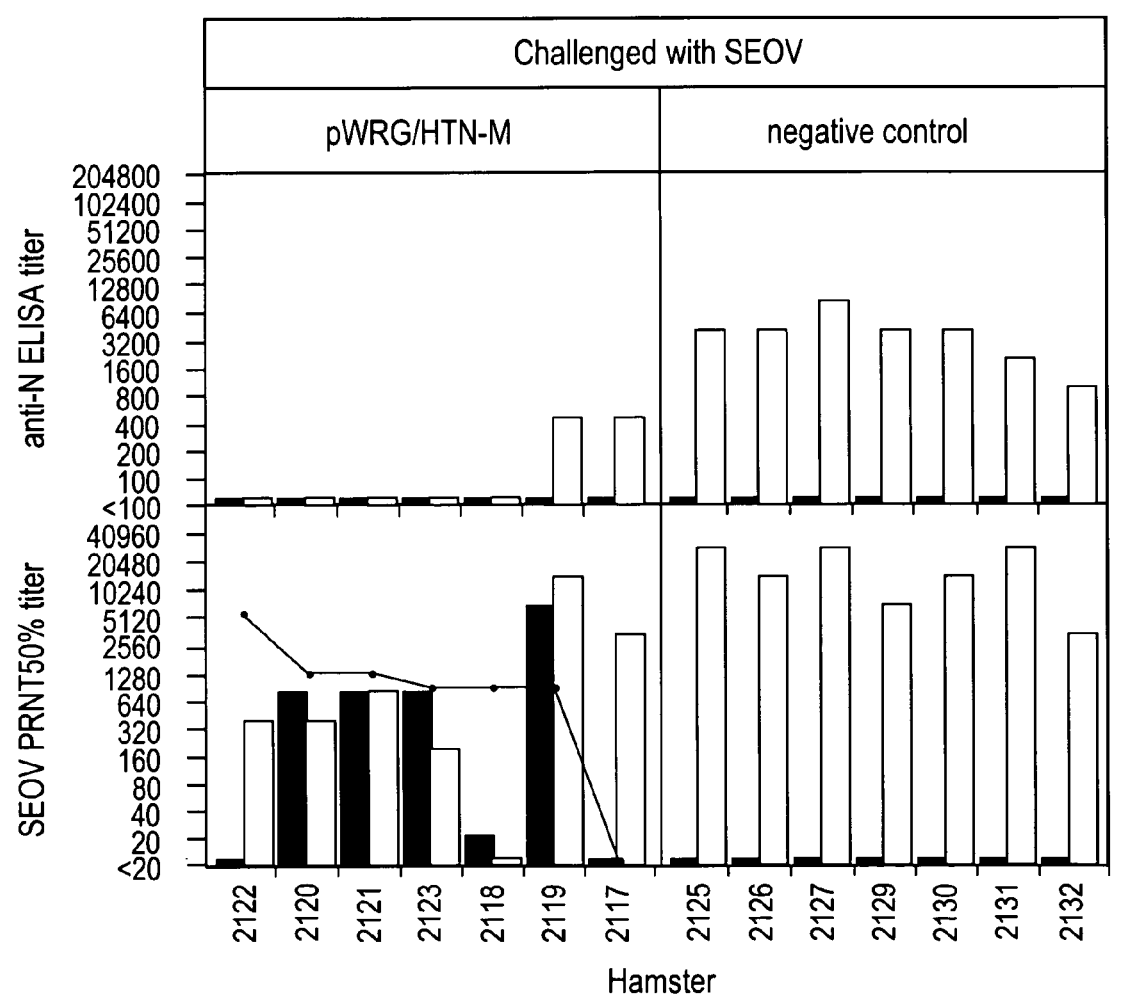
Figure 12E:
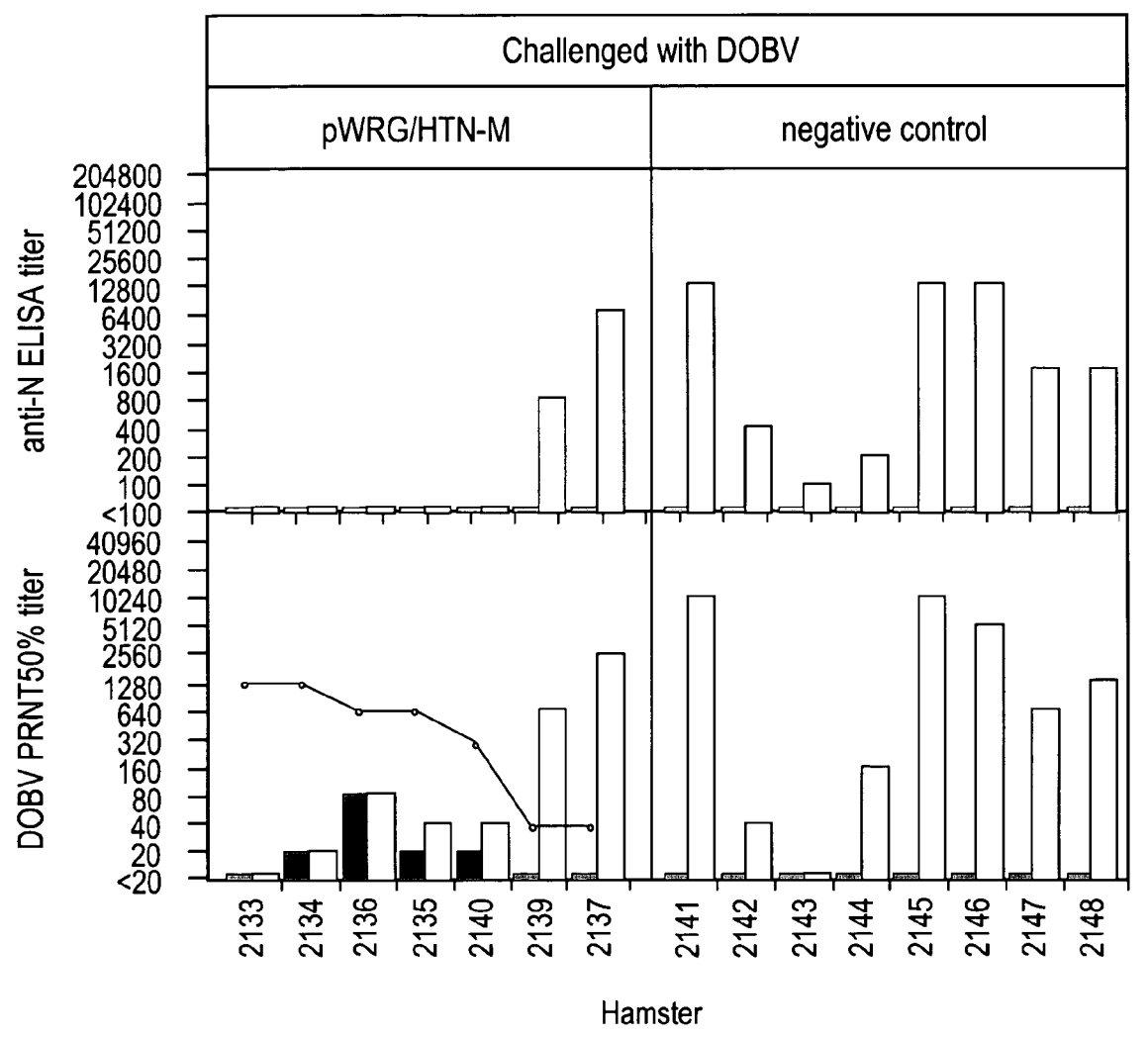

We tested the capacity of pWRG/HTN-M to cross-protect against SEOV or DOBV. The results indicated that vaccination with pWRG/HTN-M elicited cross-protective immunity against both SEOV and DOBV (FIGS. 12D and 12E). A homotypic PRNT$_{80\%}$ titer (640 was associated with protection of hamsters against SEOV, and a titer (320 protected against DOBV. We did not measure the capacity of vaccination with pWRG/HTN-M to protect against PUUV infection because of our findings that the SEOV DNA vaccine did not protect (FIG. 12C), and because a vaccinia-vectored HTNV vaccine did not protect hamsters against PUUV infection (Schmaljohn et al., 1995, Virology 206, 963–972). Together, these data indicated that DNA vaccination with either pWRG/SEO-M or pWRG/HTN-M cross-protected against three of the four HFRS-associated hantaviruses: SEOV, HTNV, and DOBV.

EXAMPLE 10

DNA Vaccination with pWRG/SEO-M or pWRG/HTN-M Elicits a High-Titer Neutralizing Antibody Response in Nonhuman Primates Our vaccination data with plasmids expressing the SEOV M gene (Hooper et al., 1999, supra) or HTNV M gene suggests that these vaccines might be efficacious in humans. As a further step toward clinical development of these vaccines, we tested their capacity to elicit antibody responses in nonhuman primates. Two rhesus macaques were vaccinated with the SEOV M DNA vaccine, and three rhesus macaques were vaccinated with the HTNV M DNA vaccine. As negative controls, three monkeys were vaccinated with pWRG7077 expressing irrelevant genes; and, as positive controls, three monkeys were vaccinated with a recombinant vaccinia virus expressing the HTNV M and S genes, rVV/HTN-M+S (Schmaljohn et al., 1992, Vaccine 10, 10–13). rVV/HTN-M+S was previously shown to elicit HTNV-specific immunity, including neutralizing antibodies, in hamsters (Chu et al., 1995, J. Virol. 69, 6417–6423) and to elicit neutralizing antibodies in humans (McClain et al., 2000, J. Med. Virol. 60, 77–85). The DNA vaccines were administered three times at three week intervals. The rVV/HTN-M+S vaccine was administered by the dose and schedule used in the human phase II trials (i.e., a primary subcutaneous vaccination followed by a boost at day 42).

Three weeks after the first vaccination, two of the three monkeys vaccinated with pWRG/HTN-M(x) demonstrated neutralizing antibodies (FIG. 13). Three weeks after the second gene gun vaccination, all of the monkeys vaccinated with either pWRG/SEO-M(x) or pWRG/HTN-M(x) demonstrated detectable levels of neutralizing antibody. Three weeks after the third vaccination, the neutralizing antibody titers in all of the monkeys vaccinated with pWRG/SEO-M(x) or pWRG/HTN-M(x) were impressively high. Negative control-vaccinated monkeys never developed neutralizing antibodies (data not shown). Monkeys vaccinated with rVV/HTN-M+S failed to develop a neutralizing antibody response after one vaccination, but did develop neutralizing antibodies after the 42-day boost. Three weeks after the final vaccination, the PRNT$_{80\%}$ GMT of the monkeys vaccinated with pWRG/SEO-M(x), pWRG/HTN M(x), or rVV/HTN-M+S, were 905, 2032, and 160, respectively. These data demonstrated, for the first time, that DNA vaccines expressing the hantavirus M gene products are immunogenic in nonhuman primates and elicit relatively high levels of neutralizing antibodies.

To evaluate the duration of immunity elicited by the DNA vaccine and the recombinant vaccinia virus vaccine, serum from vaccinated monkeys was collected 2, 4, and 6 months after the final vaccination, and tested for neutralizing activity. Two months after the final vaccination, the neutralizing antibody titers in sera from DNA-vaccinated hamsters dropped two- to fourfold (FIG. 14, Table 9 and 10). At 4 months postvaccination, monkeys vaccinated with pWRG/SEO-M(x) or pWRG/HTN-M(x) had PRNT$_{80\%}$ GMT=160 and 80, respectively. After 6 months, all of the monkeys vaccinated with pWRG/SEO-M(x) or pWRG/HTN-M(x) still had detectable levels of neutralizing antibody, PRNT$_{80\%}$ GMT=113 and 63, respectively. After 8 months one of the HTNV M DNA vaccinated monkeys (CH27) had a PRNT$_{80\%}$ titer <20, however there was still a detectable neutralizing antibody response, PRNT$_{50\%}$=20. In contrast, monkeys vaccinated with the positive control vaccine, rVV/HTN-M+S, exhibited little or no detectable neutralizing antibody 4 months after the final vaccination.

EXAMPLE 11

DNA Vaccination of Nonhuman Primates with pWRG/SEO-M or pWRG/HTN-M Vaccines Elicit Antibody that Cross-Neutralizes DOBV We tested the sera from the vaccinated monkeys for cross-neutralizing activity by PRNT (Table 4). All of the monkeys vaccinated with either pWRG/SEO-M(x) or pWRG/HTNV-M(x) had antibodies that cross-neutralized DOBV. rVV/HTN-M+S vaccinated monkeys also had DOBV-cross neutralizing antibodies, albeit at lower titer. Surprisingly, monkeys vaccinated with pWRG/SEO-M(x) had little or no HTNV-neutralizing antibody; and monkeys vaccinated with pWRG/HTN-M(x) had little or no SEOV-neutralizing antibody. Only one monkey (monkey CH32), which was DNA vaccinated with pWRG/SEO-M(x), demonstrated a detectable level of PUUV neutralizing antibody.

HTNV G1 and G2 were also transiently expressed from a plasmid containing HTNV gene controlled by a T7 promoter using the vaccinia virus/T7 RNA polymerase expression system (Kamrud and Schmaljohn, 1994, Virus Res. 31, 109–121). Problems in glycoprotein expression, however, arose when the HTNV M gene was cloned into plasmids utilizing a CMV promoter. In most cases, G2 but not G1 was expressed as measured by RIPA (data not shown). For example, pcHTN-M, a plasmid used in a recent pseudotype study (Ma et al., 1999, Virus Res. 64, 23–32) was thought to express both G1 and G2; however, subsequent RIPA results performed in our laboratory indicate that only G2 was expressed correctly (unpublished data). It is possible that G1 is expressed but incorrectly processed (e.g., incorrectly folded, secreted from the cell, targeted to the nucleus, or targeted for degradation), or partially expressed (e.g., truncated).

We found that including a short sequence of extraneous DNA upstream of the SEOV or HTNV M gene allowed G1 expression from the DNA vaccine vector pWRG7077. In pWRG7077, the CMV promoter is followed by intron A. Intron A includes elements that function to increase levels of expression of the cloned gene (Chapman et al. 1991, Nucl. Acids. Res. 19, 3979–3986). After transcription, the intron A sequence is excised from the RNA and the spliced transcript is transported from the nucleus to the cytoplasm where it is expressed. We suspected that, if the splicing of intron A was aberrant and somehow resulted in disruption of the G1 sequence, then this might account for the observed defect in G1 expression, despite normal levels of G2 expression. The extraneous sequence, which was located between the intron A and hantavirus M gene, we hypothesized, might somehow prevent the hypothetical abberrant splicing and allow normal

TABLE 4

Cross-neutralization activity in serum from vaccinated monkeys

| | | PRNT[d] | | | | | | | |
|---|---|---|---|---|---|---|---|---|---|
| | | SEOV | | HTNV | | DOBV | | PUUV | |
| Serum source[a] | Monkey[e] | 80% | 50% | 80% | 50% | 80% | 50% | 80% | 50% |
| Vaccinated[b] with pWRG/SEO-M (x) | CH03 | 640 | 1280 | * | * | 40 | 160 | * | * |
| | CH32 | 1280 | 1280 | * | 80 | 320 | 640 | * | 40 |
| Vaccinated[b] with pWRG/HTN-M(x) | CH28 | * | * | 2560 | 2560 | * | 320 | * | * |
| | CH02 | * | * | 5120 | 10240 | 160 | 320 | * | * |
| | CH27 | * | 20 | 640 | 1280 | 80 | 320 | * | * |
| Vaccinated[c] with rVV/HTN-M + S | 62F | * | * | 40 | 160 | * | 80 | * | * |
| | CH21 | * | * | 320 | 640 | * | 160 | * | * |
| | AA016 | * | * | 320 | 320 | * | 20 | * | * |

[a]Monkey serum collected 3 weeks after the final vaccination.
[b]Monkeys gene gun-vaccinated three times at 3 week intervals with the indicated DNA vaccine plasmid.
[c]Monkeys s.c. injected with recombinant vaccinia virus vaccine two times at 42-day interval.
[d]PRNT values are the reciprocal serum dilution that neutralizes the indicated virus plaque number by 80% or 50%. Homotypic titer are shown in bold.
* titer less than 20

DISCUSSION

Transient expression of a cloned HTNV V gene was first accomplished by using recombinant vaccinia virus and baculovirus systems (Pensiero et al. 1988, J. Virol. 62, 696–702; Schmaljohn et al., 1989, supra). Both G1 and G2 proteins were expressed and appeared to be biochemically and antigenically identical to the authentic viral proteins.

expression of G1 and G2. This hypothesis was bolstered when we noticed that a seven nucleotide sequence within the extraneous sequence was identical to the intron A splice acceptor site TCTGCAG (Stenberg et al., 1984, supra). However, mutation of the putative splice acceptor in the extraneous sequence had no effect on G1 expression (FIG. 9B). This does not rule out the possibility that some other splicing event influences G1 expression from the pWRG7077 plasmid. Further experimentation will be required to elucidate how a short run of nucleotides, GGATCTG, positioned upstream of the cloned SEOV and HTNV M gene is capable of affecting the expression of G1 but not G2. Regardless of the mechanism, this finding allowed us to develop a candidate DNA vaccine against HTNV.

Our previous results with the SEOV M DNA vaccine, coupled with the results reported here demonstrating immunogenicity and protective efficacy of the HTNV M DNA vaccine, make a strong case for the use of the full-length M gene in DNA vaccines against other hantaviruses. It remains unclear whether or not G1 alone, G2 alone, or fragments of the glycoproteins can elicit neutralizing antibody and protect against infection. Vaccination with recombinant baculovirus-infected cell lysates containing G1 or G2 alone, and recombinant vaccinia viruses expressing G1 or G2 alone, failed to elicit neutralizing antibody, and exhibited incomplete protection in a hamster infection model (Schmaljohn et al., 1990, J. Virol. 64, 3162–3170). These data suggest that a full-length M gene capable of expressing G1 and G2 may be required for protective immunity. In contrast, Bharadwai et al. reported low levels of neutralizing antibody after i.m. needle injection of mice with DNA vaccine plasmids containing short (~166 amino acid) sections of the M gene of Sin Nombre virus (SNV), a HPS-associated hantavirus (Bharadwai et al., 1999, Vaccine 17, 2836–2843). This finding suggests that to elicit a neutralizing antibody response, it not only doesn't require a full-length M gene, but also occurs when only subunits of G1 or G2 are expressed. Presently, we are performing experiments designed to test the capacity of DNA vaccines that express HTNV G1 alone, G2 alone, or a combination of G1 and G2 (expressed from different plasmids) to elicit neutralizing antibody and protect hamsters from infection.

There are at least 10 hantaviruses known to cause either HFRS or HPS, so information on cross-neutralization and cross-protection among hantaviruses is important for the rational design of cross-protective vaccines. Investigators have evaluated the capacity of serum from various species (including humans) infected with hantaviruses to cross-neutralize other hantaviruses (Chu et al., 1995, supra; Niklasson et al., 1991, Am. J. Trop. Med. Hyg. 45, 660–665; Lee et al., 1985, J. Clin. Microbiol. 22, 940–944; Lundkvist et al. 1997, J. Med. Virol. 53, 51–59). Different species, and different individuals within a species, appear to exhibit differing levels of cross-neutralizing antibody. In general, data from these experiments indicate that serum from HTNV-, SEOV-, or DOBV-infected individuals share cross-neutralizing antibodies, albeit with about a fourfold difference in titer among the serotypes. Whereas, serum from PUUV-infected individuals exhibit little or no SEOV-, HTNV-, or DOBV-cross-neutralizing antibodies. Our data obtained with sera from infected, or DNA-vaccinated, hamsters are consistent with earlier findings. We observed a greater level of cross-neutralizing antibody in the pooled sera from the DNA-vaccinated hamsters than the pooled sera from infected hamsters. This may reflect a qualitative difference between the antibodies elicited after DNA vaccination and the antibodies elicited by infection, or it may simply reflect a quantitative difference in antibody levels. It is noteworthy that high homotypic neutralizing antibody levels in vaccinated hamsters did not necessarily correlate with cross-neutralizing activity (FIG. 12).

The cross-neutralization tests with the hamster serum pools suggested that if neutralizing antibody could predict protective immunity, then vaccination with either pWRG/SEO-M or pWRG/HTN-M would protect against SEOV, HTNV, but not PUUV; and this we found, in general, to be true. Data in FIG. 12 indicate that the presence of cross-neutralizing antibodies correlated with a protective effect with a single exception. Hamster 2119 exhibited cross-neutralizing antibody, but was not protected by definition because there was a detectable anti-N response. However, the absence of detectable levels of cross-neutralizing antibody didn't necessarily predict a lack of protection. Examples of the latter case can be found in FIG. 12, hamsters 1437, 1434, 2122, and 2133. It is possible that cross-neutralizing antibodies are present, but not detected due to limitations of the assay, or that non-neutralizing responses also are protective.

In this study, we demonstrated that vaccination with either pWRG/SEO-M or pWRG/HTN-M cross-protected against SEOV, HTNV, and DOBV. Other experimental hantavirus vaccines have the capacity to cross-protect. For example a vaccinia recombinant expressing the HTNV G1, G2, and N (rVV/HTN-M+S) cross-protected against infection with SEOV but not PUUV (Chu et al., 1995, J. Virol. 69, 6417–6423), and vaccinia recombinants expressing the SEOV G1 and G2, or N, cross-protected against HTNV (Xu et al., 1992, Am. J. Trop. Med. Hyg. 47, 397–404). Ours is the first report to demonstrate protection against DOBV.

The hantavirus M gene-based DNA vaccines not only elicited positive responses in rhesus macaques, but also elicited a level of neutralizing antibody that was relatively high. When we combined the serological data from the SEOV and HTNV M gene DNA thrice-vaccinated monkeys, the $PRNT_{80\%}$ GMT was 1470. This neutralizing antibody response was almost 10 times greater that elicited by the recombinant vaccinia virus vaccine, $PRNT_{80\%}$ GMT=160, $PRNT_{50\%}$ GMT=320. The rVV/HTN-M+S neutralizing antibody response was similar to the neutralizing antibody responses previously reported for humans, $PRNT_{50\%}$ GMT=160 (McClain et al., 2000, supr). Inactivated hantavirus vaccines administered to humans also routinely elicit neutralizing antibody titers of ~100 (Yu et al., 1999, In: Factors in the Emergence and Control of Rodent-borne Viral Diseases (Hantavirus and Arenal Diseases), J. F. Saluzzo and B. Dodet, Eds., pp. 157–161. Elsevier Press, Paris; Zhu et al. 1994, Chinese Med. J. 107, 167–170).

We found that the level of neutralizing antibody in the vaccinated monkeys dropped in the months after the final gene gun vaccination. Nevertheless, even after 6 months, neutralizing antibody could still be detected in all of the monkeys vaccinated with either pWRG/SEO-M(x) or pWRG/HTN-M(x). In comparison, monkeys vaccinated with rVV/HTN-M+S did not have detectable levels of neutralizing antibody after 4 months (FIG. 14).

In China, where several inactivated virus vaccines against hantaviruses have been developed and tested in humans, the PRNT assay is used to evaluate the potency of the vaccine (Zhu et al., 1994, supra, reviewed in Yu et al., 1999, supra). Most of the inactivated virus vaccines made in cell culture elicit neutralizing antibody in 90–100% of the vaccinees after three doses, GMT≦100. The seropositive rate drops to ~50% 6 months after the final boost, but can be restored by administering a booster vaccination. Although the hantavirus vaccines developed in Asia show promise in terms of efficacy, we have directed our efforts towards the development of recombinant hantavirus vaccines that avoid the safety concerns inherent to inactivated-virus vaccines. Moreover, we believe it might be possible to elicit a more robust neutralizing antibody response using a vaccine platform that entails expression of G1 and G2 within the cells of the vaccinee (e.g., DNA vaccine), rather than as exogenous proteins (e.g., beta-propiolactone-treated virions combined with adjuvant). The high neutralizing antibody response elicited in our DNA-vaccinated monkeys suggests that very high levels of neutralizing antibody are attainable by this vaccine approach.

EXAMPLE 12 pWRG/HTN-M(x) partially protects against a lethal ANDV challenge. We previously demonstrated that our HTNV M gene-based DNA vaccine, pWRG/HTN-M(x), could cross-protect against three of the four hantaviruses that cause HFRS. To determine if this vaccine could protect against the hantavirus that causes HPS, we vaccinated hamsters three times at 3-week intervals with pWRG/HTN-M(x) or a negative control plasmid and then challenged them with ANDV (250 $LD_{50}$, i.m.) 3 weeks after the last vaccination. Two independent experiments were performed and the combined results are shown in FIG. 15. The vaccine elicited HTNV NAb (50% neutralization geometric mean titers [GMT]=226; range <20–5120) in all but one hamster. ANDV cross-NAb was not detected, with one exception (#514, titer=20). After challenge, 15 of 24 hamsters vaccinated with pWRG/HTN-M(x) died and 14 of 15 negative controls died. The mean day-of-death was 13 for both groups. Thus, the protection against a lethal ANDV challenge afforded by vaccination with pWRG/HTN-M(x) was not statistically significant, but was suggestive (P=0.0569). Hamsters that survived challenge were re-challenged with ANDV to ensure they were exposed to virus. At least one animal (ID#504) had no antibody response after two successive challenges but was clearly protected from lethal disease.

EXAMPLE 13

ANDV M gene-based DNA vaccine expresses G1 and G2. Because the level of protection afforded by pWRG/HTN-M(x) in our experiments was only 38%, we endeavored to construct an ANDV M gene-based DNA vaccine. The full-length M gene of ANDV, strain Chile-9717869, was RT-PCR cloned into pWRG7077 to yield pWRG/AND-M (SEQ ID NO:8). We sequenced the entire M gene open reading frame. The sequence of our cloned M gene was almost identical to the published M gene sequence of ANDV, GeneBank accession number AF291703, which is not surprising because the viral isolates were from the same rodent specimen (Meissner et al., 2002, Virus Res. 89, 131–143). There were two adenine to guanine nucleotide changes. The change at position 1504 was silent and the change at position 1840 resulted in a threonine to alanine substitution at amino acid 597.

Expression of G1 and G2 in transfected COS cells was evaluated by RIPA. Serum pools from convalescent HPS patients immunoprecipitated polypeptides with the predicted size of G1 and G2 from pWRG/AND-M-transfected cells or ANDV-infected cells (FIGS. 17A–B). The sizes of the expression products were similar to the sizes of G1 and G2 of other hantaviruses; which range from 68–76 kDa for G1 and 52–58 kDa for G2 (Schmaljohn and Hooper, 2001, In: Fields Virology, 4th Edition, Lippincott, Williams, and Wilkins, Philadelphia, Pa., pp. 1581–1602). We presume that the ~46-kDa protein in the ANDV-infected cells but not the pWRG/AND-M transfected cells, was the ANDV nucleocapsid protein. To confirm that the polypeptides were G1 and G2, we screened a battery of HTNV G1- and G2-specific MAbs for capacity to immunoprecipitate the ANDV glycoproteins from cells transfected with pWRG/AND-M or pWRG/HTN-M(x). We were unable to identify HTNV G1-specific MAbs that cross-reacted with the ANDV G1 protein; MAb-2D5, MAb-6D4, MAb-8B6 (FIG. 17C), MAb-10F11, or MAb-3D5 (data not shown). HTNV G2-specific MAb-23G10, MAb-16E6, and MAb-HCO2 did not immunoprecipitate ANDV G2; however, HTNV G2-specific MAb-3D7 did immunoprecipitate ANDV G2 from the pWRG/AND-M transfected cells (FIG. 17C). By deduction, we concluded that the protein with mobility just under the 69-kDa marker that is precipitated by HPS patient sera but not the G2-specific MAb-3D7 is ANDV G1. The identity of the ~70-kDa protein remains unknown.

EXAMPLE 14 pWRG/AND-M DNA vaccine is neither immunogenic, nor protective in hamsters. To test the immunogenicity of pWRG/AND-M, we vaccinated 24 hamsters three times at 3-week intervals using a gene gun, collected serum samples, and tested them for NAb by PRNT. ANDV-specific NAb were not detected (data not shown). Hamsters vaccinated with pWRG/HTN-M(x) on the same days did develop HTNV-specific NAb with titers as high as 10240 (data not shown). To determine if vaccination with pWRG/AND-M elicited ANDV G1- or G2-specific non-neutralizing antibodies, we performed IFAT with cells transfected with pWRG/AND-M. No antibody against G1 or G2 was detected in representative sera from hamsters vaccinated with pWRG/AND-M, but antibody was detected in positive control samples that were sera from hamsters previously infected with ANDV (data not shown). We repeated the entire vaccination experiment on a second group of seven hamsters and, again, no NAb response was detected (data not shown). Because there was a possibility the vaccinations with pWRG/AND-M elicited a nonhumoral, but nevertheless protective, immune responses, we challenged eight hamsters from the first experiment and seven hamsters from the second experiment with a 250 $LD_{50}$ of ANDV. Twelve of the 14 hamsters vaccinated with pWRG/AND-M developed HPS and died. Six of eight unvaccinated hamsters developed HPS and died. The mean-day-of-death was between 12 and 13 for both vaccinated and unvaccinated groups. From these negative data, we concluded that pWRG/AND-M was not immunogenic in Syrian hamsters.

EXAMPLE 15 pWRG/AND-M elicits a high-titer NAb response in rhesus macaques. To determine if the lack of immunogenicity of pWRG/AND-M in hamsters was a species-specific phenomenon, we tested this plasmid in a rhesus macaque. The monkey, ID# CH69, was vaccinated by gene gun with pWRG/AND-M four times at 3-week intervals. As positive controls, two rhesus macaques were vaccinated with pWRG/HTN-M(x), which we previously showed to be immunogenic in nonhuman primates. Serum collected before each vaccination and then 3 weeks after the fourth vaccination was tested for the presence of HTNV and ANDV NAbs (FIGS. 18A,C). Monkey CH69 vaccinated with pWRG/AND-M and the positive control monkeys vaccinated with pWRG/HTN-M(x) developed NAb responses after the second vaccination and the NAb titers were extraordinarily high after the fourth vaccination (FIGS. 18A,C).

We tested serum from the vaccinated monkeys for a capacity to cross-neutralize other HPS-associated hantaviruses. Serum from the monkey vaccinated with pWRG/AND-M, but not PWRG/HTN-M(x) neutralized SNV and BCCV (FIG. 18A). Serum from monkeys vaccinated with pWRG/AND-M or pWRG/HTN-M(x) did not cross-neutralize HTNV or ANDV, respectively.

Pre- and postvaccination (6 weeks after the last vaccination), serum was collected from monkey CH69 and tested by RIPA for a capacity to immunoprecipitate the ANDV glycoproteins. The post- but not prevaccination serum immunoprecipitated proteins similar to those immunoprecipitated by human convalescent sera: a strong G2 band, a weak G1 band, and a ~70-kDa band of unknown identity (FIG. 18B).

To confirm that vaccination with pWRG/AND-M was immunogenic in rhesus macaques, we vaccinated a second animal four times at 3-week intervals. This monkey (ID# 90BD25) developed a PRNT$_{50}$ titer of 5120 after the second vaccination, and a titer of 10240 3 weeks after the fourth vaccination (FIG. 18C). Thus, the capacity of pWRG/AND-M to elicit high-titer NAb in nonhuman primates was reproducible.

To look at the duration of the NAb response in the monkeys vaccinated with the HPS or HFRS DNA vaccine, serum samples were periodically collected for approximately 6 months. The monkeys vaccinated with pWRG/AND-M still had PRNT$_{50}$ titers between 320 (monkey ID# 90BD25) and 2560 (monkey ID# CH69), 20 and 25 weeks after the last vaccine, respectively (FIG. 18C). The two positive control monkeys vaccinated with pWRG/HTN-M (x) still had homologous PRNT$_{50}$ titers (640 25 weeks after the last vaccination.

EXAMPLE 16

Dual construct protects against HTNV and ANDV infection. A construct comprising both the Hantaan M gene and the Andes M gene was prepared. The Hantaan M gene and the Andes M gene were cloned into pWRG7077 to produce pWRG/HA-M (SEQ ID NO:9). Each M gene was flanked by a cytomegalovirus promoter and intron A (CMV intron A) and a bovine growth hormone poly adenylation site. The entire Hantaan virus and Andes virus M gene open reading frames as well as most of the 5' and 3' noncoding sequences are included in the construct. In addition, the 24 bp sequence positioned between each hantavirus M sequence and its respective CMV intron A sequence. As discussed above, we have found, for unknown reasons, this 24 bp sequence (or a portion thereof) is required for expression of G1 glycoprotein.

When pWRG/HA-M was introduced into mammalian cells, the Hantaan virus and Andes virus M genes were expressed. The expression products consist of the Hantaan virus G1 and G2 glycoproteins and the Andes virus G1 and G2 glycoproteins.

The Hantaan/Andes dual-M gene hantavirus DNA vaccine, pWRG/HA-M, was tested for immunogenicity in rhesus macaques. The vaccine elicited an antibody response that neutralized Hantaan virus and Andes virus (see Table 8). In a single hamster experiment, we found that this plasmid was similar to the Andes virus plasmid, in that it did not elicit an antibody response in hamsters. However, the fact it elicits neutralizing antibodies in monkeys suggests it could elicit neutralizing antibodies in humans. This is the first DNA vaccine designed to protect against all hantaviruses, both HPRS-associated and HPS-associated, that cause severe disease.

EXAMPLE 17

Passive transfer of serum from a monkey vaccinated with pWRG/AND-M 1 day before challenge delays or prevents HPS in hamsters. Having successfully vaccinated rhesus macaques with a HPS DNA vaccine, we were interested in determining if the NAb response elicited by this vaccine could protect hamsters from a lethal ANDV infection. To test this, serum from a monkey vaccinated with pWRG/AND-M, or a monkey vaccinated with a negative control plasmid, was injected into groups of four hamsters. The next day the animals were challenged with ANDV (250 LD$_{50}$, i.m.) and observed daily for 4 weeks. All hamsters that received serum containing ANDV NAb survived and all hamsters that received negative control serum died between 10 and 13 days after challenge (Table 5). PRNT were performed on serum samples collected on the day of challenge (day 0) and collected from survivors on day 28. Hamsters that were injected with the protective monkey serum, which had an ANDV PRNT$_{50}$ titer of 20480, had PRNT$_{50}$ titers between 320 and 1280 at the time of challenge. Four weeks later, these hamsters had no detectable NAb and no nucleocapsid-specific antibody as measured by ELISA. Thus, these hamsters not only survived, but also the data suggest that they had sterile immunity to infection from the challenge.

In a second experiment, a different serum pool from a monkey vaccinated with pWRG/AND-M (ANDV PRNT$_{50}$ titer=640) was injected into four hamsters. As negative controls, four hamsters were injected with serum from a monkey vaccinated with a negative control plasmid. The hamsters were challenged with ANDV (250 LD$_{50}$, i.m.) and observed daily for 14 weeks. As expected, all of the hamsters injected with the negative control monkey serum developed HPS and died between days 10 and 14 (Table 5). Whereas in the first experiment all of the hamsters injected with the serum from the monkey vaccinated with pWRG/AND-M were sterilely protected, in the second experiment two of the hamsters died on day 23, and the other two hamsters died on day 40. Together, the aforementioned experiments indicate that passive transfer of serum from a monkey vaccinated with pWRG/AND-M on the day before challenge can sterilely protect hamsters from a lethal ANDV challenge, or significantly delay disease onset and death.

TABLE 5

Pre- and postchallenge passive transfer of sera from rhesus macaques vaccinated with pWRG/AND-M to hamsters

| Hamster ID# | Antibody Source[a] | Day[b] injected | PRNT titer[c] | Challenge virus[d] | Day of death[e] | Terminal bleed[f] | | % Protection | |
|---|---|---|---|---|---|---|---|---|---|
| | | | | | | PRNT titer[g] | ELISA titer[h] | From lethality | From infection[i] |
| 905 | AND-M | −1 | 320 | ANDV | — | <20 | <100 | 50 | 50 |
| 906 | | −1 | 640 | ANDV | — | <20 | <100 | | |
| 907 | | −1 | 320 | ANDV | — | <20 | <100 | | |
| 908 | | −1 | 1280 | ANDV | — | <20 | <100 | | |
| 105 | | −1 | 20 | ANDV | 23 | na | na | | |
| 106 | | −1 | 40 | ANDV | 23 | na | na | | |
| 107 | | −1 | 20 | ANDV | 40 | na | na | | |
| 108 | | −1 | 20 | ANDV | 40 | na | na | | |
| 901 | (−) | −1 | <20 | ANDV | 12 | na | na | 0 | 0 |
| 902 | | −1 | <20 | ANDV | 13 | na | na | | |
| 903 | | −1 | <20 | ANDV | 10 | na | na | | |
| 904 | | −1 | <20 | ANDV | 13 | na | na | | |
| 101 | | −1 | <20 | ANDV | 10 | na | na | | |

TABLE 5-continued

Pre- and postchallenge passive transfer of sera from rhesus macaques vaccinated with pWRG/AND-M to hamsters

| Hamster ID# | Antibody Source[a] | Day[b] injected | Day 0 PRNT titer[c] | Challenge virus[d] | Day of death[e] | Terminal bleed[f] PRNT titer[g] | ELISA titer[h] | % Protection From lethality | From infection[i] |
|---|---|---|---|---|---|---|---|---|---|
| 102 | | −1 | <20 | ANDV | 14 | na | na | | |
| 103 | | −1 | <20 | ANDV | 10 | na | na | | |
| 104 | | −1 | <20 | ANDV | 11 | na | na | | |
| 909 | AND-M | 3 | <20 | ANDV | — | <20 | <100 | 88 | 14 |
| 910 | | 3 | <20 | ANDV | — | <20 | 400 | | |
| 911 | | 3 | <20 | ANDV | — | 2560 | 12800 | | |
| 912 | | 3 | <20 | ANDV | — | 160 | 800 | | |
| 109 | | 3 | <20 | ANDV | — | >640 | 1600 | | |
| 110 | | 3 | <20 | ANDV | — | 640 | 6400 | | |
| 111 | | 3 | <20 | ANDV | 12 | na | na | | |
| 112 | | 3 | <20 | ANDV | — | >640 | 3200 | | |
| 113 | AND-M | 4 | <20 | ANDV | — | 160 | 400 | 100 | 0 |
| 114 | | 4 | <20 | ANDV | — | 640 | 400 | | |
| 115 | | 4 | <20 | ANDV | — | >640 | 12800 | | |
| 116 | | 4 | <20 | ANDV | — | 320 | 1600 | | |
| 117 | AND-M | 5 | <20 | ANDV | — | 320 | 1600 | 100 | 0 |
| 118 | | 5 | <20 | ANDV | — | >640 | 1600 | | |
| 119 | | 5 | <20 | ANDV | — | 640 | 800 | | |
| 120 | | 5 | <20 | ANDV | — | 160 | 400 | | |
| 121 | AND-M | 6 | <20 | ANDV | 11 | na | na | 38 | 0 |
| 122 | | 6 | <20 | ANDV | — | 40 | 800 | | |
| 123 | | 6 | <20 | ANDV | 13 | na | na | | |
| 124 | | 6 | <20 | ANDV | 12 | na | na | | |
| 913 | | 6 | <20 | ANDV | 11 | na | na | | |
| 914 | | 6 | <20 | ANDV | — | 1280 | 12800 | | |
| 915 | | 6 | <20 | ANDV | 10 | na | na | | |
| 916 | | 6 | <20 | ANDV | — | 1280 | 6400 | | |
| 917 | AND-M | 9 | <20 | ANDV | 11 | na | na | 25 | 0 |
| 918 | | 9 | <20 | ANDV | 13 | na | na | | |
| 919 | | 9 | <20 | ANDV | — | 10240 | 12800 | | |
| 920 | | 9 | <20 | ANDV | 11 | na | na | | |
| 921 | AND-M | −1 | 160 | PBS | — | <20 | <100 | 100 | 100 |
| 922 | | −1 | 640 | PBS | — | <20 | <100 | | |
| 923 | | −1 | <20 | PBS | — | <20 | <100 | | |
| 924 | | −1 | 160 | PBS | — | <20 | <100 | | |

[a]Serum from monkey vaccinated with pWRG/AND-M (AND-M) or negative control sera (−).
[b]Day antibody injected relative to challenge (Day 0).
[c]NAb titer in hamster serum at time of challenge.
[d]2000 PFU of ANDV (250 LD$_{50}$), or PBS was injected i.m. on day 0.
[e]—, animal survived.
[f]In exp 1 (ID# 909–924), terminal bleed on day 28. In exp 2 (ID# 109–124), terminal bleed on day 98.
[g]Reciprocal of highest dilution neutralizing 50% of the plaques; na, not applicable.
[h]Endpoint ELISA titer.
[i]Sterile immunity indicates no detectable antibody response to nucleocapsid.

TABLE 6

Passive transfer of sera from NHP vaccinated with pWRG/HTN-M(x) in a nonlethal infection model.

| Hamster ID# | Antibody source[a] | Day 0 PRNT titer[b] | Challenge virus[c] | Terminal bleed[f] PRNT titer[d] | ELISA titer[e] | % Sterile immunity[g] |
|---|---|---|---|---|---|---|
| 492 | HTN-M | 640 | HTNV | 20 | <100 | Y |
| 493 | | 1280 | HTNV | 80 | <100 | Y |
| 494 | | 640 | HTNV | 20 | <100 | Y |
| 495 | | 1280 | HTNV | 20 | 200 | N |
| 496 | | 640 | HTNV | <20 | <100 | Y |
| 497 | | 1280 | HTNV | 1280 | <100 | Y |
| 498 | | <20 | HTNV | 5120 | 12800 | N |
| 499 | | 640 | HTNV | ND | <100 | Y |
| 484 | (−) | <20 | HTNV | >640 | >12800 | N |
| 485 | | 20 | HTNV | >640 | >12800 | N |
| 486 | | <20 | HTNV | >640 | >12800 | N |
| 488 | | <20 | HTNV | >640 | >12800 | N |
| 489 | | <20 | HTNV | >640 | >12800 | N |
| 490 | | <20 | HTNV | >640 | 3200 | N |
| 491 | | <20 | HTNV | >640 | >12800 | N |
| 476 | none | <20 | HTNV | >640 | >12800 | N |
| 477 | | <20 | HTNV | >640 | >12800 | N |
| 478 | | <20 | HTNV | >640 | >12800 | N |
| 479 | | <20 | HTNV | >640 | >12800 | N |
| 480 | | <20 | HTNV | >640 | >12800 | N |
| 481 | | <20 | HTNV | >640 | >12800 | N |

TABLE 6-continued

Passive transfer of sera from NHP vaccinated with pWRG/HTN-M(x) in a nonlethal infection model.

| | | Day 0 | | Terminal bleed[f] | | |
|---|---|---|---|---|---|---|
| Hamster ID# | Antibody source[a] | PRNT titer[b] | Challenge virus[c] | PRNT titer[d] | ELISA titer[e] | % Sterile immunity[g] |
| 482 | | <20 | HTNV | >640 | >12800 | N |
| 483 | | <20 | HTNV | >640 | >12800 | N |

[a]HTN-M indicates serum from monkey vaccinated with pWRG/HTN-M (x); (−) indicates serum from negative control monkey vaccinated with irrelevant plasmid; none indicates no passive transfer.
[b]NAb titer (50%) in hamster serum at time of challenge.
[c]2000 PFU of HTNV (1000 LD$_{50}$) was injected i.m. on day 0.
[d]Reciprocal of highest dilution neutralizing 50% of the plaques; ND, not done.
[e]Endpoint ELISA titer.
[f]Terminal bleed was on day 35 after challenge.
[g]Sterile immunity indicates no detectable antibody response to nucleocapsid. Y and N, yes and no sterile immunity, respectively.

TABLE 7

Pre- and postchallenge passive transfer of plasma from a Chilean HPS patient to hamsters

| | | Day 0 | | | | Terminal bleed[f] | | % Protection | |
|---|---|---|---|---|---|---|---|---|---|
| Hamster ID# | Antibody Source[a] | Day[b] injected | PRNT titer[c] | Challenge virus[d] | Day of death[e] | PRNT titer[g] | ELISA titer[h] | From lethality | From infection[i] |
| 125 | Normal | −1 | <20 | ANDV | 12 | na | na | 0 | 0 |
| 126 | | | <20 | ANDV | 10 | na | na | | |
| 127 | | | <20 | ANDV | 11 | na | na | | |
| 128 | | | <20 | ANDV | 12 | na | na | | |
| 129 | HPS | −1 | 640 | ANDV | — | <20 | <100 | 50 | 50 |
| 130 | | | 1280 | ANDV | 57 | na | na | | |
| 131 | | | 640 | ANDV | 68 | na | na | | |
| 132 | | | 1280 | ANDV | — | <20 | <100 | | |
| 133 | HPS | 3 | <20 | ANDV | — | >640 | 3200 | 75 | 0 |
| 134 | | | <20 | ANDV | — | 160 | 800 | | |
| 135 | | | <20 | ANDV | — | 80 | 800 | | |
| 136 | | | <20 | ANDV | 12 | na | na | | |
| 137 | HPS | 4 | <20 | ANDV | 12 | na | na | 50 | 0 |
| 138 | | | <20 | ANDV | 15 | na | na | | |
| 139 | | | <20 | ANDV | — | 320 | 1600 | | |
| 140 | | | <20 | ANDV | — | 320 | 3200 | | |
| 141 | HPS | 5 | <20 | ANDV | — | >640 | 6400 | 50 | 0 |
| 142 | | | <20 | ANDV | — | 40 | <100 | | |
| 143 | | | <20 | ANDV | 11 | na | na | | |
| 144 | | | <20 | ANDV | 11 | na | na | | |
| 145 | HPS | −1 | 40 | None | — | <20 | <100 | 100 | 100 |
| 146 | | | 640 | None | — | <20 | <100 | | |
| 147 | | | 320 | None | — | <20 | <100 | | |

[a]HPS indicates plasma from a human HPS patient; normal indicates normal human serum.
[b]Day antibody injected (1 ml i.p.) relative to challenge (Day 0).
[c]NAb titer in hamster serum at time of challenge.
[d]2000 PFU of ANDV (250 LD$_{50}$) was injected i.m. (ANDV), or no treatment (None).
[e]—, animal lived.
[f]Terminal bleed on day 98.
[g]Reciprocal of highest dilution neutralizing 50% of the plaques; na, not applicable.
[i]Protection from infection (sterile immunity) indicates no detectable antibody response to nucleocapsid.

EXAMPLE 18

Passive transfer of serum from a monkey vaccinated with pWRG/AND-M to hamsters 4–5 days after ANDV challenge completely protects against lethal HPS. We tested serum from a monkey vaccinated with pWRG/AND-M for protective efficacy when administered to hamsters 3, 4, 5, 6, or 9 days after ANDV challenge (Table 5). Fifteen of the 16 hamsters that received antibody on days 3, 4, or 5 after challenge survived. However, if antibody was administered 6 days after challenge, only three of eight hamsters survived; and if antibody was administered 9 days after challenge only one of four hamsters survived. All but one of the survivors from the postexposure experiments (ID#909, day 3) were infected with ANDV, as measured by PRNT and nucleocapsid-specific ELISA. Unlike the pre-challenge passive transfer experiments described above, in the postchallenge passive transfer experiments, we did not observe any late deaths. Thus, immunoprophlaxis with serum from monkeys vaccinated with pWRG/AND-M, up to 5 days after a lethal challenge with ANDV, protected from 88–100% of the ANDV-challenged hamsters.

EXAMPLE 19

Passive transfer of sera from HTN-M DNA-vaccinated monkeys protects hamsters against HTNV infection. In earlier studies we demonstrated that vaccinating hamsters with pWRG/HTN-M(x) elicited NAbs and protected against infection; however, we never tested whether or not the antibodies elicited were, by themselves, were sufficient to protect. To address this question, groups of hamsters were either not injected, or were injected with a pool of sera from monkeys vaccinated four times with pWRG/HTN-M(x) (PRNT$_{50}$ titer=20480), or from a monkey vaccinated with a negative control plasmid. One day after passive transfer, the hamsters were bled and challenged with HTNV. Five weeks after challenge, the hamsters were terminally bled and serum from day 0 and day 35 were tested for HTNV NAbs by PRNT, and nucleocapsid-specific antibodies by ELISA (Table 6). All of the hamsters that were injected with the negative control serum or no serum were clearly infected as indicated by high PRNT and nucleocapsid-specific ELISA titers. In contrast, six of the eight hamsters injected with the serum from the monkeys vaccinated with pWRG/HTN-M (x) failed to develop detectable anti-nucleocapsid antibodies by ELISA. Hamster #495 had a low ELISA titer indicating a low level of infection. Although hamster #498 was in the group injected with immune serum, no NAb response was detected at the time of challenge, indicating antibody was not successfully transferred, which explains why this animal was not protected against HTNV infection. Thus, serum from nonhuman primates vaccinated with pWRG/HTN-M (x), administered 1 day before challenge, was sufficient to protect hamsters against infection with HTNV.

EXAMPLE 20

Passive transfer of plasma from human HPS patient. Having demonstrated that serum from monkeys vaccinated with ANDV M gene-based DNA vaccines could protect against a lethal ANDV challenge when administered pre- or postexposure, we investigated the capacity of human convalescent plasma from a Chilean HPS patient (human-HPS plasma) to protect in the ANDV/hamster lethal disease model. Human-HPS plasma, with an initial ANDV NAb PRNT$_{50}$ titer of 10240, was injected into different groups of hamsters on day −1, 3, 4, or 5. A control group was injected with normal human serum on day −1. On day 0, blood was collected from the hamsters and then the hamsters were challenged with ANDV (250 LD$_{50}$, i.m.). As a control for toxicity, three hamsters that were injected with the human-HPS plasma on day −1 were not challenged. Hamsters were monitored for 98 days, survivors were terminally bled, and PRNT and ELISA were performed on the day 0 and day 98 serum samples (Table 7). All of the hamsters receiving normal human sera died between 10 and 12 days after challenge. Two of the four hamsters that received human-HPS plasma on day −1 survived. The other two hamsters in the day −1 group developed HPS and died on days 57 and 68 after challenge. Seven of the 12 hamsters that received antibody on days 3, 4, or 5 after challenge survived. The hamsters that died in those groups did so between 11 and 15 days after challenge. The three hamsters in the toxicity control groups all remained healthy.

Serology results from the postchallenge sera indicate that the two hamsters that were injected with human-HPS plasma on day −1, and survived, were protected from infection (i.e., they did not produce anti-nucleocapsid antibodies)(Table 7). All but one of the hamsters that received the human-HPS plasma after challenge, and survived, were nevertheless infected because they all produced anti-nucleocapsid antibodies. Thus, human-HPS plasma protected at least half the challenged hamsters when administered on day −1, 3, 4, or 5. Hamsters receiving the plasma on day −1 were either protected from infection, or survived more than four times longer than the controls.

DISCUSSION

Presently, there are no vaccines, effective antiviral drugs, or immunologics to protect against or treat HPS. This is disconcerting because HPS afflicts previously healthy individuals in all age groups, disease progression is rapid, and the case-fatality is one of the highest for any acute viral disease known. Reports of person-to-person transmission of ANDV-associated HPS in southern Argentina and Chile make development of countermeasures against this highly lethal disease more urgent (Padula et al., 1998, Virology 241, 323–330; Toro et al., 1997, Emerg. Infect. Dis. 4, 687–694; Wells et al., 1997, Emerg. Infect. Dis. 3, 171–174). Here, we report the development of a candidate HPS DNA vaccine that elicits high-titer NAb in nonhuman primates. Moreover, we report that the antibodies elicited by this vaccine can protect hamsters from lethal HPS, even when administered 5 days after challenge.

This is the first study in which a hantavirus disease model in an adult laboratory animal has been used to evaluate the protective efficacy of a candidate vaccine, drug, or immunoprophylactic. Previous studies used hantavirus infection models involving mice, hamsters, or bank voles to evaluate vaccines and immunoprophylactics, or a suckling mouse neurologic-disease model to evaluate drugs (Hooper and Li, 2001, In: Hantaviruses, p. 171–191, Springer-Verlag, Berlin, Germany; Schmaljohn and Hooper, 2001, supra) Here, we used a recently described ANDV/hamster lethal disease model (Hooper et al., 2001, Virology 289, 6–14). We confirmed that ANDV causes lethal HPS in adult Syrian hamsters and determined that the challenge had a relatively consistent outcome. Of the 35 hamsters that were negative controls in the active vaccination or passive transfer experiments, 100% of the ANDV-challenged hamsters were infected and 91% developed fatal HPS (mean-day-of-death=12, range 10–15 days). Onset of symptoms (e.g., dyspnea) was rapid and death usually occurred within 24 h after onset.

In an earlier study, we demonstrated that previous infection with HTNV, SEOV, DOBV, PUUV, or SNV could protect hamsters against a lethal ANDV challenge (Hooper et al., 2001, supra). From this, we reasoned that it might be possible to use our HTNV M gene-based DNA vaccine, pWRG/HTN-M(x), to protect hamsters against ANDV challenge. We tested this possibility and found that pWRG/HTN-M(x) protected 9 of 24 hamsters from a lethal ANDV challenge. This level of protection was not statistically significant (P=0.0569) but did suggest that the vaccine was eliciting some immunity against ANDV. It is possible that the pWRG/HTN-M(x) vaccine would afford a higher level of protection against a challenge dose less than 250 LD$_{50}$, or against a different challenge route (e.g., aerosol or oral route). There was essentially no ANDV cross-neutralizing antibodies in either the serum of pWRG/HTN-M(x)-vaccinated hamsters (FIG. 14) or in the HTNV-infected hamsters that were protected in our earlier work (Hooper et al., 2001, supra). This suggests that the cross-protection we observed in previously infected hamsters was due to cell-mediated-immunity targeting both nucleocapsid and glycoproteins; whereas the partial cross-protection we observed in the pWRG/HTN-M(x)-vaccinated hamsters was likely due to cell-mediated-immunity targeting only the glycoproteins. It is theoretically possible that the product of the L genome segment could play a role in the protection observed in previously infected hamsters; however, there is presently no evidence that the viral polymerase elicits humoral- or cell-mediated-immunity. Cross-protection after infection with HTNV, but not after inoculation with the HTNV glycoproteins, suggests that vaccination with a plasmid(s) expressing both the HTNV nucleocapsid and glycoproteins might mimic HTNV infection and cross-protect against ANDV.

In an alternative approach to developing a HPS vaccine, we constructed a plasmid designed to specifically protect against viruses that cause HPS. The plasmid, pWRG/AND-M, contains the complete ANDV M gene open reading frame and expresses both the G1 and G2 glycoproteins in cell culture. To our knowledge, the BCCV M gene is the only other HPS-hantavirus complete M gene that has been successfully cloned and expressed (Ravkov et al., 1998, J. Virol. 72, 2865–2870). In that study the BCCV M gene was cloned into a Sindbis virus replicon system, SIN-rep5, and expression was detected in BHK21 cells by immunoprecipitation.

Vaccination with pWRG/AND-M elicited a potent NAb response in rhesus macaques. This is the first candidate HPS vaccine shown to unequivocally elicit a NAb response in any laboratory animal. Not only were NAbs produced in the monkeys, but also 1) NAbs were detected after only two vaccinations; 2) NAb titers were very high (i.e., titers as high as those found in HPS-patient convalescent serum); 3) the NAbs cross-neutralized at least two other HPS-associated hantaviruses, SNV and BCCV; and 4) NAbs were still detected 6 months after the last vaccination. The neutralization of SNV suggests that the pWRG/AND-M vaccine would protect against the major HPS-hantaviruses in South America and North America, ANDV and SNV, respectively. The neutralization of BCCV suggests that vaccination with pWRG/AND-M might protect against a wide range of HPS-associated hantaviruses (See Table 8). These data coupled with our HFRS DNA vaccine data indicate that a vaccine comprised of both pWRG/HTN-M(x) and pWRG/AND-M could conceivably protect against several major hantaviruses known to be highly lethal to humans.

TABLE 8

Immunogenicity of hantavirus M gene-based DNA vaccines in nonhuman primates: response after 1 through 4 vaccinations.

| Exp[a] | DNA vaccine plasmid | Monkey ID # | Titer 3 wks after vaccination[b] | | | |
|---|---|---|---|---|---|---|
| | | | vacc1 | vacc2 | vacc3 | vacc4 |
| I | pWRG/SEO-M(x) | CH03 | <20 | 160 | 1280 | na |
| I | " | CH32 | <20 | 160 | 1280 | na |
| I | pWRG/HTN-M(x) | CH28 | 40 | 1280 | 2560 | na |
| I | " | CH02 | 40 | 1280 | 10240 | na |
| I | " | CH27 | <20 | 320 | 1280 | na |
| II | " | CH64 | <20 | 160 | 1280 | 20480 |
| II | " | CH85 | <20 | 160 | 320 | 20480 |
| II | pWRG/AND-M | CH69 | <20 | 2560 | 2560 | 20480 |
| III | " | 90BD25 | <20 | 5120 | 5120 | 10240 |
| III | pWRG/HA-M[c] | CAA | HTN<20 | 160 | 80 | 320 |
| | | | AND<20 | <20 | <20 | 320 |
| | " | HJV | HTN<20 | 320 | 160 | >640 |
| | | | AND<20 | 40 | 80 | 640 |

[a]Three independent experiments were performed. Monkeys received 8 g.g. administrations per vacc.
[b]PRNT$_{50}$ titer against homotypic virus. For pWRG/HA-M, Hantaan (HTN) and Andes (AND) titers are given.
[c]pWRG/HA-M is a plasmid containing both the Andes virus and Hantaan virus M gene.

All monkey vaccinated with our Hantaan, Seoul, Andes, or Hantaan/Andes M gene-based DNA vaccines elicited neutralizing antibody levels that were still detectable after six months. Two of three monkeys vaccinated with pWRG/HTN-M(x) still had detectable levels of neutralizing antibodies two years after the last vaccination (Table 9). A summary of duration of immunity data is shown in Table 10.

TABLE 9

Immunogenicity of hantavirus M gene-based DNA vaccines in nonhuman primates: duration of immunity.

| Exp[a] | DNA vaccine plasmid | Monkey ID # | PRNT$_{50}$ Titer Months after final vaccination | | | | |
|---|---|---|---|---|---|---|---|
| | | | ~1 | ~6 | ~12 | ~18 | ~24 |
| I | pWRG/SEO-M(x) | CH03 | 1280 | 160 | 320 | nd | |
| I | | CH32 | 1280 | 320 | 40 | nd | |
| I | pWRG/HTN-M(x) | CH28 | 2560 | 320 | 80 | 160 | 80 |
| I | | CH02 | 10240 | 320 | 80 | 640 | 80 |
| I | | CH27 | 1280 | 40 | <20 | <20 | <20 |
| II | | CH64 | 20480 | 640 | nd | | |
| II | | CH85 | 20480 | 1280 | nd | | |
| II | pWRG/AND-M | CH69 | 20480 | 2560 | nd | | |
| III | | 90BD25 | 10240 | 320 | nd | | |

[a]Three independent exp. were performed. Monkeys received 8 g.g. administrations per vacc.
[b]PRNT$_{50}$ titer against homotypic virus.

TABLE 10

Immunogenicity of hantavirus M gene-based DNA vaccines in nonhuman primates: duration of immunity.

| DNA vaccine | Geometric Mean Titer[a] Months after final vaccination | | | | |
|---|---|---|---|---|---|
| | ~1 | ~6 | ~12 | ~18 | ~24 |
| pWRG/SEO-M(x) | 1280 | 226 | 113 | nd | nd |
| pWRG/HTN-M(x) | 6756 | 320 | 40 | 101 | 40 |
| pWRG/AND-M | 14482 | 269 | nd | nd | nd |
| all | 5530 | 373 | nd | nd | nd |

[a]PRNT$_{50}$ titer against homotypic virus

One of the more perplexing results we obtained during the course of this study was the failure of pWRG/AND-M to elicit a detectable immune response in hamsters. In two independent experiments, hamsters vaccinated three times with pWRG/AND-M failed to produce antibodies detectable by PRNT or IFAT, and were not protected against a lethal ANDV challenge. In contrast, rhesus macaques vaccinated as few as two times with pWRG/AND-M developed a detectable NAb response. Although unlikely, it is possible that the DNA vaccine was nonimmunogenic in hamsters for technical reasons. Before exploring the mechanism by which pWRG/AND-M might fail to generate an immune response in hamsters, and whether this phenomenon is related to the highly lethal nature of ANDV in Syrian hamsters, it would be prudent to evaluate the pWRG/AND-M vaccine in hamsters and nonhuman primates in a side-by-side experiment using the same vaccine lot and vaccination schedule in both species. For the current study, the important point is that pWRG/AND-M is highly immunogenic in nonhuman primates.

In previous studies we demonstrated that DNA vaccines expressing the glycoproteins of SEOV or HTNV elicited NAb in mice, hamsters, and nonhuman primates, and we demonstrated that the presence of NAb in vaccinated hamsters correlated with protection against infection (Hooper et al., 1999, Virology 255, 269–78; Kamrud et al., 1999, Virology 263, 209–219). Here, we demonstrate for the first time that the humoral response elicited by DNA vaccination with pWRG/HTN-M(x) is sufficient to protect against infection with HTNV. Specifically, we demonstrated that passive transfer of serum from a monkey vaccinated with pWRG/HTN-M(x) 1 day before challenge provided sterilizing protection in six of eight hamsters challenged with HTNV. The two hamsters that were not protected either had a limited infection (hamster #495) as determined by a very low postchallenge, anti-nucleocapsid titer; or did not receive a proper injection of serum (hamster #498) as determined by the absence of detectable NAb on the day of challenge. It is possible that a similar passive transfer assay could be used as part of a clinical study to evaluate sera from humans vaccinated with pWRG/HTN-M(x), and to predict efficacy of the vaccine.

Presently there is no treatment for individuals exposed, or potentially exposed, to HPS hantaviruses. Reports that high NAb titers in patients admitted to hospitals correlated with favorable clinical course suggested that NAbs might ameliorate disease, and therefore, immunotherapy could be a viable treatment option to persons exposed to HPS viruses (Bharadwaj et al., 2000, J. Infect. Dis. 182, 43–48). For HFRS-associated hantaviruses, passive transfer of infected-rat immune serum or mouse MAbs conferred protection against infection in hamsters or neurologic disease in newborn rats or suckling mice (Arikawa et al., 1989, J. Gen. Virol. 70, 615–24; Liang et al., 1996, Virology 217, 262–271; Schmaljohn et al., 1997, J. Virol. 71, 9563–9569; Zhang et al., 1989, Arch. Virol. 105, 235–246). For HPS hantaviruses, there have been no reports of the passive transfer of protective immunity. The discovery of the ANDV/hamster lethal disease model has allowed us, for the first time, to evaluate the capacity of antibodies to protect against a hantavirus disease that resembles the disease in humans. Using this model, we demonstrated that passive transfer of serum from a monkey vaccinated with pWRG/AND-M protected 100% of challenged hamsters from a lethal ANDV infection when administered on day 4 or 5 after exposure. This finding indicates that it should be possible to develop a product (e.g., polyclonal immunoglobulin from primates, including humans, vaccinated with pWRG/AND-M and/or pWRG/HTN-M(x), or MAbs that neutralize ANDV and/or HTNV) that could be used to treat laboratory workers exposed to hantaviruses, family members or other close contacts of HFRS or HPS patients, or medical personnel treating HPS cases, especially in South America where there is evidence of person-to-person transmission of HPS(Padula et al, 1998, Virology 241, 323–330; Toro et al., 1997, supra; Wells et al., 1997, Emerg. Infect. Dis. 3, 171–174).

HPS-patient convalescent plasma was essentially equivalent to the monkey serum when administered on day 3 postexposure (75% vs 88% protection) but only protected 50% of the hamsters when administered on day 4 or 5 postexposure. Due to low sample numbers, this difference could be an artifact. Alternatively, it is possible the human NAbs were cleared more rapidly than the rhesus macaque NAbs resulting in a lower effective NAb titer at the time of challenge. We have not evaluated the kinetics by which the monkey or human hantavirus-specific NAbs are cleared from hamsters.

Passive transfer of sera from monkeys vaccinated with pWRG/AND-M, or HPS-patient plasma, administered 1 day before challenge, either protected hamsters against a lethal ANDV challenge with sterile immunity, or delayed disease onset and death by two- to almost fourfold. In the experiments involving passive transfer of serum containing ANDV NAb (Table 5 and 7), the only hamsters that died late were those that were injected with serum 1 day before challenge. The six hamsters died on days 23, 23, 40, 40, 57, and 68 for a mean-day-of-death=42. This was a significant delay in death because the 12 hamsters that were injected with negative control serum (monkey or human) all died between days 10 and 14, mean-day-of-death=12. We surmise that the late deaths in the hamsters injected with antibody on day −1 were the result of clearance of the heterologous monkey or human ANDV-specific NAb, and subsequent virus amplification from virus introduced either "from without" (e.g., ANDV shed from hamsters in other cages in the same room) or "from within" (e.g., virus that escaped neutralization by the passively transferred antibody and infected a cell). We hypothesize that late deaths were not observed in hamsters that received serum postexposure because the challenged hamsters had mounted an active immune response to the challenge virus. This active immunity would normally be insufficient to protect the hamsters against ANDV; however, passively transferred immunity (i.e., NAbs in serum from a monkeys vaccinated with pWRG/AND-M) administered on day 3 thru 5 would tip the balance in favor of the hamster and allow survival (22 of 28 survived, see tables 6 and 7). The active immune response would persist and protect the hamster when, and if, the hamster was re-exposed to ANDV after clearance of the passive immunity. In support of this, all but one (#902, Table 5) of the 26 survivors that received passively transferred antibody on day 3, 4, 5, 6, or 9, were nevertheless infected, as indicated by a anti-nucleocapsid and/or NAb response detectable several weeks after challenge. Regardless of whether the late deaths can be attributed to re-exposure from "within" or from "without," these data suggest that a post-hantavirus-exposure prophylaxis treatment regimen might require repeated administrations, or both passive transfer of antibodies and active vaccination. A passive/active vaccination approach for postexposure prophylaxis is routinely used to prevent other viral diseases including hepatitis A, hepatitis B. and rabies (Centers for Disease Control, Atlanta, Ga., 1991, MMWR 40, 1–19, MMWR 48, 1–21, MMWR 48, 1–37).

Most of the hamsters that received the ANDV-specific NAb on day 6 or 9 died, indicating that immunoprophylaxis might become less effective as disease progresses. Others have reported that the small molecule drug ribavirin might have been ineffective for treating HPS because, for most patients, drug treatment was initiated after onset of clinical symptoms (Chapman et al, 1999, Antivir. Ther. 4, 211–219). The critical pathogenic juncture where damage caused by the infection is irreversible and prophylaxis is impossible has not been defined. Future studies characterizing the time course of HPS in the Andes/hamster lethal disease model will provide insights into the pathogenesis of HPS, and should allow us to formulate strategies for pre- and postexposure prophylaxis and therapy.

What is claimed is:

1. An isolated nucleic acid comprising SEQ ID NO: 6.

2. A DNA fragment which encodes a Hantaan hantavirus M gene segment and the sequence according to claim 1.

3. A DNA fragment which encodes a Seoul hantavirus M gene segment and the sequence according to claim 1.

4. A DNA fragment which encodes an Andes hantavirus M gene segment and the sequence according to claim 1.

5. A recombinant DNA construct comprising:
   (i) a vector,
   (ii) at least one hantavirus M gene nucleic acid fragment, and
   (iii) the isolated nucleic acid of claim 1.

6. The recombinant DNA construct of claim 5 wherein said construct is pWRG/SEO-M set forth in SEQ ID NO:3.

7. The recombinant DNA construct of claim 5 wherein said construct is pWRG/HTN-M(x) set forth in SEQ ID NO:7.

8. The recombinant DNA construct of claim 5 wherein said construct is pWRG/AND-M(x) set forth in SEQ ID NO:8.

9. The recombinant DNA construct of claim 5 wherein said construct comprises two said hantavirus M gene nucleic acid fragments.

10. The recombinant DNA construct of claim 9 wherein said construct is pWRG/HA-M set forth in SEQ NO:9.

11. A DNA fragment which encodes a hantavirus M gene segment encoding G1 and the nucleic acid sequence comprising SEQ ID NO:6.

* * * * *